(12) United States Patent
Hanon

(10) Patent No.: US 8,668,904 B2
(45) Date of Patent: *Mar. 11, 2014

(54) INFLUENZA COMPOSITION

(75) Inventor: Emmanuel Jules Hanon, Rixensart (BE)

(73) Assignee: Glaxosmithkline Biologicals S.A., Rixensart (BE)

( * ) Notice: Subject to any disclaimer, the term of this patent is extended or adjusted under 35 U.S.C. 154(b) by 86 days.

This patent is subject to a terminal disclaimer.

(21) Appl. No.: 12/746,397

(22) PCT Filed: Dec. 4, 2008

(86) PCT No.: PCT/EP2008/066815
§ 371 (c)(1),
(2), (4) Date: Jun. 4, 2010

(87) PCT Pub. No.: WO2009/071633
PCT Pub. Date: Jun. 11, 2009

(65) Prior Publication Data
US 2010/0260797 A1 Oct. 14, 2010

Related U.S. Application Data

(60) Provisional application No. 60/992,899, filed on Dec. 6, 2007, provisional application No. 61/055,569, filed on May 23, 2008.

(51) Int. Cl.
*A61K 39/145* (2006.01)
*A61K 38/00* (2006.01)

(52) U.S. Cl.
USPC ...................... 424/93.2; 424/209.1

(58) Field of Classification Search
None
See application file for complete search history.

(56) References Cited

FOREIGN PATENT DOCUMENTS

| WO | WO 95/17210 | 6/1995 |
|---|---|---|
| WO | WO 01/22992 | 4/2001 |
| WO | WO2006/100109 A1 * | 9/2006 |
| WO | WO 2006/100110 | 9/2006 |
| WO | WO 2007/052057 | 5/2007 |

OTHER PUBLICATIONS

Stephenson et al. Vaccine 2003, vol. 21, issue 15, pp. 1687-1693.*
Perrone et al. PLos Pathogens, Aug. 2008, vol. 4, issue 8, pp. 1-11.*
Illustrated Dictionary of Immunology 2nd Edition, by Julius M. Cruse et al. published in 2003 by CRC Press LLC, p. 460.*
Mossad. S. Cleveland Clinic Journal of Mediicnie, 2003, vol. 70, No. 9, pp. 801-806.*
Leroux-Roels, et al., "Antigen sparing and cross-reactive immunity with an adjuvanted rH5N1 prototype pandemic influenza vaccine: A randomised controlled trial", *The Lancet*, 370(9587):580-589 (2007).
Keitel, et al., "Preparing for a possible pandemic: Influenza A/H5N1 vaccine development", *Current Opinion in Pharmacology*, 7(5):484-490 (2007).
Chattaraj, et al., "Biodegradable microparticles of influenza viral vaccine: Comparison of the effects of routes of administration on the in vivo immune response in mice", *Journal of Controlled Release*, 58(2):223-232 (1999).
Satsuta, et al., "A Study on the spread of influenza", The Japan Medical Journal, 3158(357892):43-48, 1984 (English translation).

* cited by examiner

*Primary Examiner* — Bao Li
(74) *Attorney, Agent, or Firm* — Natalie A. Lissy; Gwynedd Warren

(57) ABSTRACT

The present invention relates to influenza vaccine formulations and accelerating primary vaccination regimes for immunizing against influenza disease, their use in medicine, in particular their use in promoting effective immune responses to various antigens, and to methods of preparation. In particular, the invention relates to two-doses accelerated pandemic or seasonal pandemic primary immunization regimes with influenza immunogenic compositions comprising an influenza virus or antigenic preparation thereof in combination with an oil-in-water emulsion adjuvant, and to accelerated immunization regimes.

28 Claims, 10 Drawing Sheets

FIG. 1 GMTs of H5N1 HI antibody titres against A/Vietnam/1194/2004 (H5N1) vaccine strain and against A/Indonesia/05/2005 (H5N1) strain

|  | HN[1x3.8] | HN[2x3.8] | HN[1x3.8A] | HN[2x3.8A] | HN[1x3.8] | HN[2x3.8] | HN[1x3.8A] | HN[2x3.8AD] |
|---|---|---|---|---|---|---|---|---|
| PRE | 5.2 | 5 | 5.1 | 5.1 | 9.7 | 8.8 | 11.3 | 10.2 |
| D21 | 5.3 | 5.6 | 6.9 | 8.6 | 16.8 | 20.8 | 50 | 69.4 |
| D42 | 6.1 | 6.3 | 13.7 | 24.4 | 22.7 | 25.3 | 126.8 | 237.3 |

(FLU A/IND/05 AB: first four columns; FLU A/VIET/04 AB: last four columns)

FIG. 2 Seroconversion rates for H5N1 HI antibody titer against H5N1 A/Vietnam /1194/2004 and A/Indonesia/05/2005 at D21 and D42

|  | HN[1x3.8] | HN[2x3.8] | HN[1x3.8A] | HN[2x3.8A] | HN[1x3.8] | HN[2x3.8] | HN[1x3.8A] | HN[2x3.8A] |
|---|---|---|---|---|---|---|---|---|
|  | FLU A/IND/05 AB | | | | FLU A/VIET/04 AB | | | |
| D21 | 1.9 | 2.3 | 3.3 | 9 | 14.8 | 18.2 | 45.4 | 52.4 |
| D42 | 3.7 | 4.5 | 23 | 40 | 22.2 | 22.7 | 72.4 | 88.3 |

FIG. 3 Seroprotection rates for H5N1 HI antibody titer against H5NI A/Vietnam /1194/2004 and A/Indonesia/05/2005 at D21 and D42 post-vaccination

| | HN[1x3.8] | HN[2x3.8] | HN[1x3.8A] | HN[2x3.8A] | HN[1x3.8] | HN[2x3.8] | HN[1x3.8A] | HN[2x3.8A] |
|---|---|---|---|---|---|---|---|---|
| | FLU A/IND/05 AB | | | | FLU A/VIET/04 AB | | | |
| PRE | 0 | 0 | 0 | 0 | 13 | 4.5 | 18.4 | 15.9 |
| D21 | 1.9 | 2.3 | 3.3 | 9 | 27.8 | 34.1 | 61.2 | 62.1 |
| D42 | 3.7 | 4.5 | 23 | 40.7 | 35.2 | 38.6 | 83.6 | 95.9 |

FIG. 4 Seroconversion factors for H5N1 HI antibody titer against H5NI A/Vietnam /1194/2004 and A/Indonesia/05/2005 at D21 and D42 post-vaccination

| | HN[1x3.8] | HN[2x3.8] | HN[1x3.8A] | HN[2x3.8A] | HN[1x3.8] | HN[2x3.8] | HN[1x3.8A] | HN[2x3.8A] |
|---|---|---|---|---|---|---|---|---|
| | FLU A/IND/05 AB | | | | FLU A/VIET/04 AB | | | |
| D21 | 1 | 1.1 | 1.4 | 1.7 | 1.7 | 2.4 | 4.4 | 6.8 |
| D42 | 1.2 | 1.3 | 2.7 | 4.8 | 2.3 | 2.9 | 11.2 | 23.2 |

FIG. 5 Seroconversion rates for H5N1 HI antibody titer against H5NI A/Vietnam /1194/2004 at D21 and D42, analysed by pre-vaccination sero-status

| | HN[1x3.8] neg | HN[1x3.8] pos | HN[2x3.8] neg | HN[2x3.8] pos | HN[1x3.8A] neg | HN[1x3.8A] pos | HN[2x3.8A] neg | HN[2x3.8A] pos |
|---|---|---|---|---|---|---|---|---|
| PI(D21) | 18.2 | 9.5 | 14.3 | 25 | 44.4 | 46.8 | 50.5 | 55.8 |
| PII(D42) | 21.2 | 23.8 | 17.9 | 31.3 | 73.3 | 71 | 94.6 | 76.9 |

FIG. 6 Seroprotection rates for H5N1 HI antibody titer against H5NI A/Vietnam /1194/2004 at D21 and D42, analysed by pre-vaccination sero-status

FLU A/VIET/04 AB

|  | HN[1x3.8] neg | HN[1x3.8] pos | HN[2x3.8] neg | HN[2x3.8] pos | HN[1x3.8 AD] neg | HN[1x3.8 AD] pos | HN[2x3.8 AD] neg | HN[2x3.8 AD] pos |
|---|---|---|---|---|---|---|---|---|
| PRE | 0 | 33.3 | 0 | 12.5 | 0 | 45.2 | 0 | 44.2 |
| PI(D21) | 18.2 | 42.9 | 14.3 | 68.8 | 44.4 | 85.5 | 50.5 | 82.7 |
| PII(D42) | 21.2 | 57.1 | 17.9 | 75 | 73.3 | 98.4 | 94.6 | 98.1 |

FIG. 7A   CMI response against H5N1 vaccine strain A/Vietnam/1194/2004
(Influenza-specific CD4 T-cells): CD4.ALL DOUBLES analysis
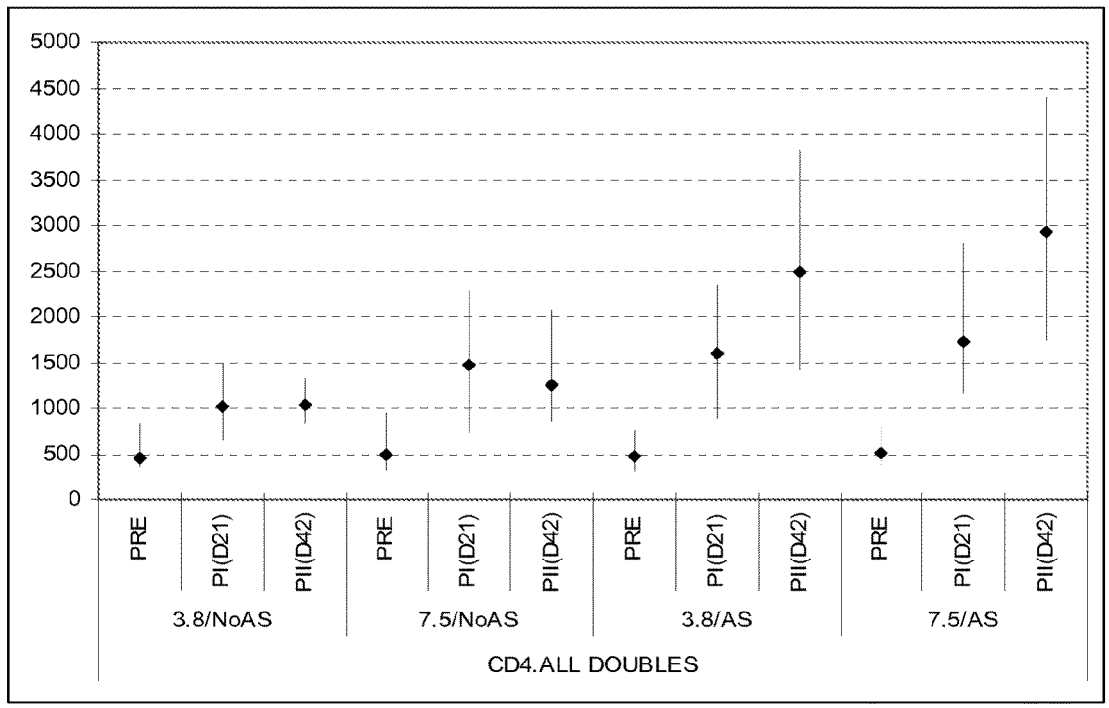
FIG. 7B   CMI response against H5N1 vaccine strain A/Vietnam/1194/2004
(Influenza-specific CD4 T-cells): CD4.CD40L analysis
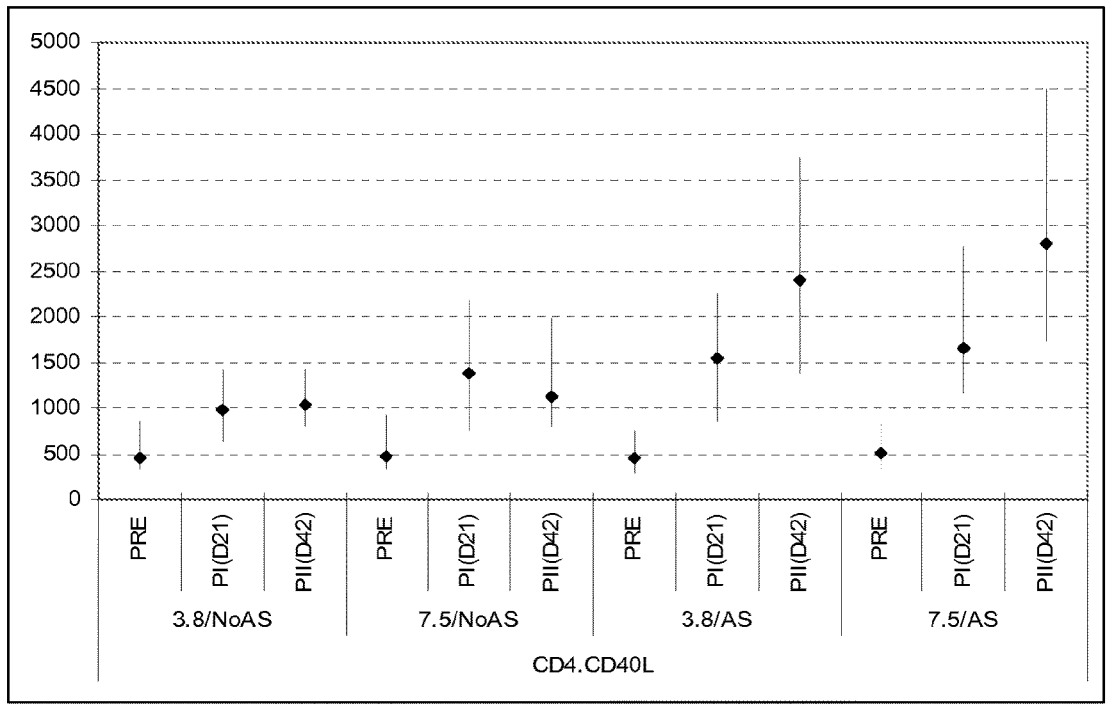

FIG. 7C   CMI response against H5N1 vaccine strain A/Vietnam/1194/2004
(Influenza-specific CD4 T-cells): C FIG. 7E  Cell-mediated immune response against H5N1 vaccine strain A/Vietnam/1194/2004 (Influenza-specific CD4 T-cells): CD4.TNFa analysis
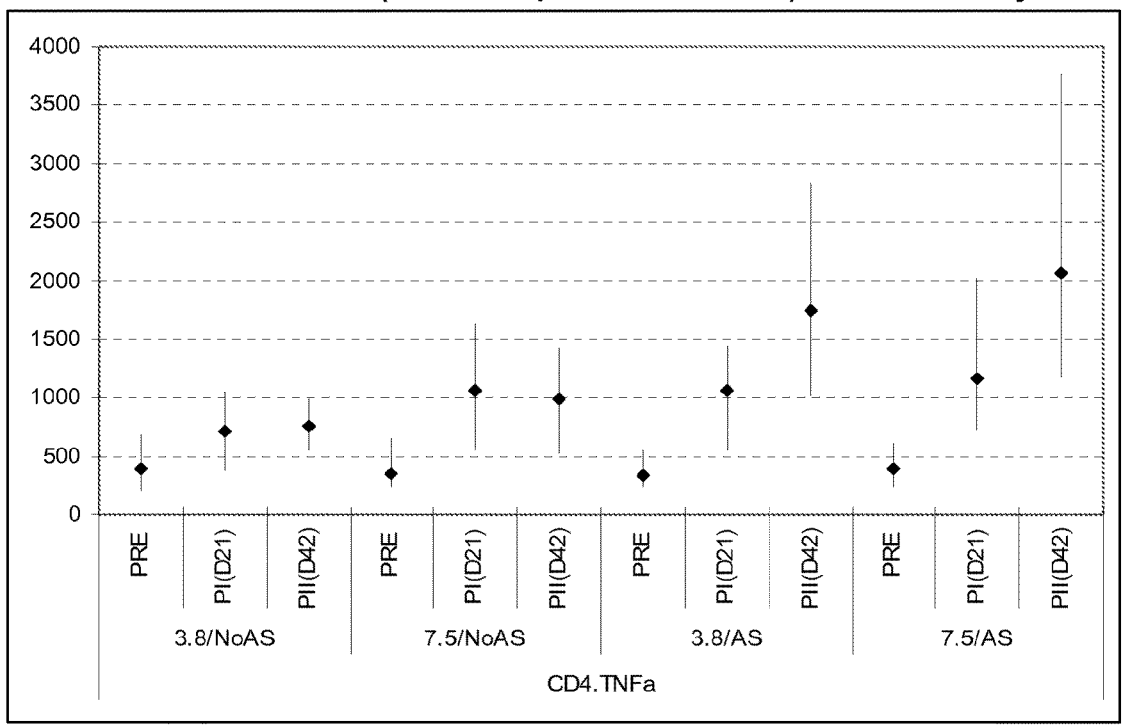
FIG. 8  HI response against A/Vietnam/1194/2004 in C57Bl/6 mice
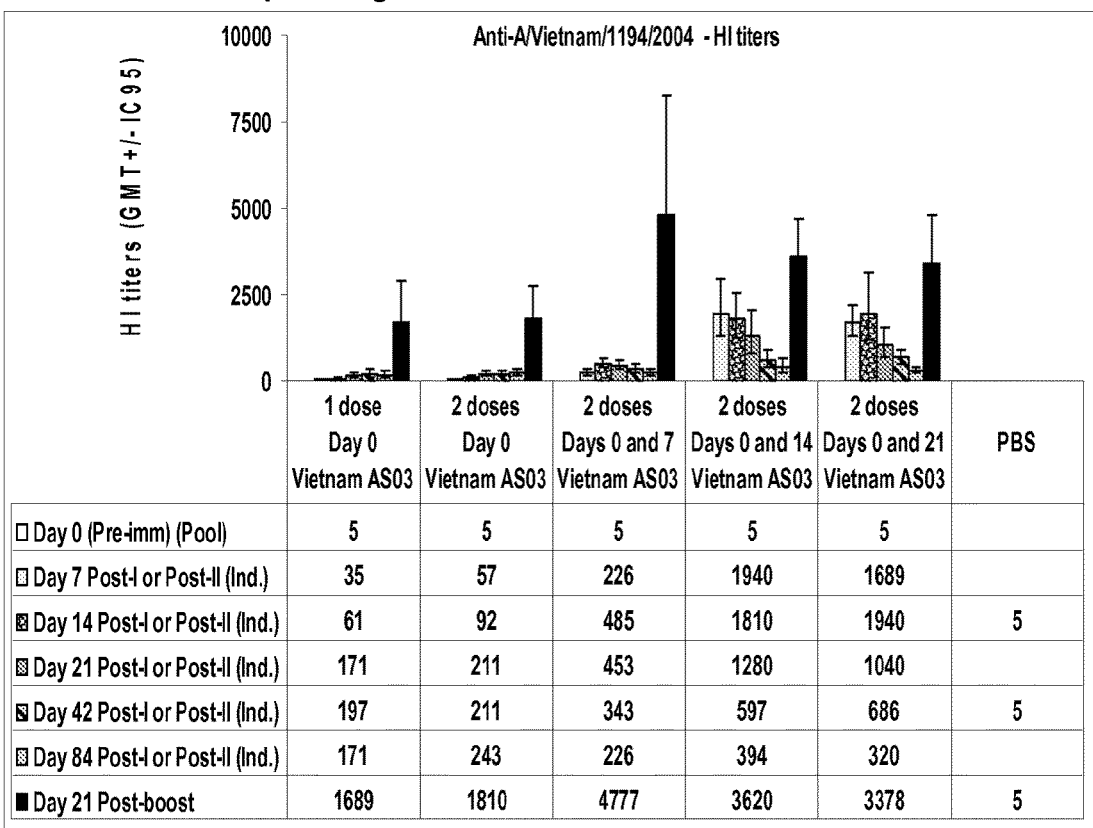

FIG. 9  Neutralizing antibody response against A/Vietnam/1194/2004 in C57Bl/6 mice
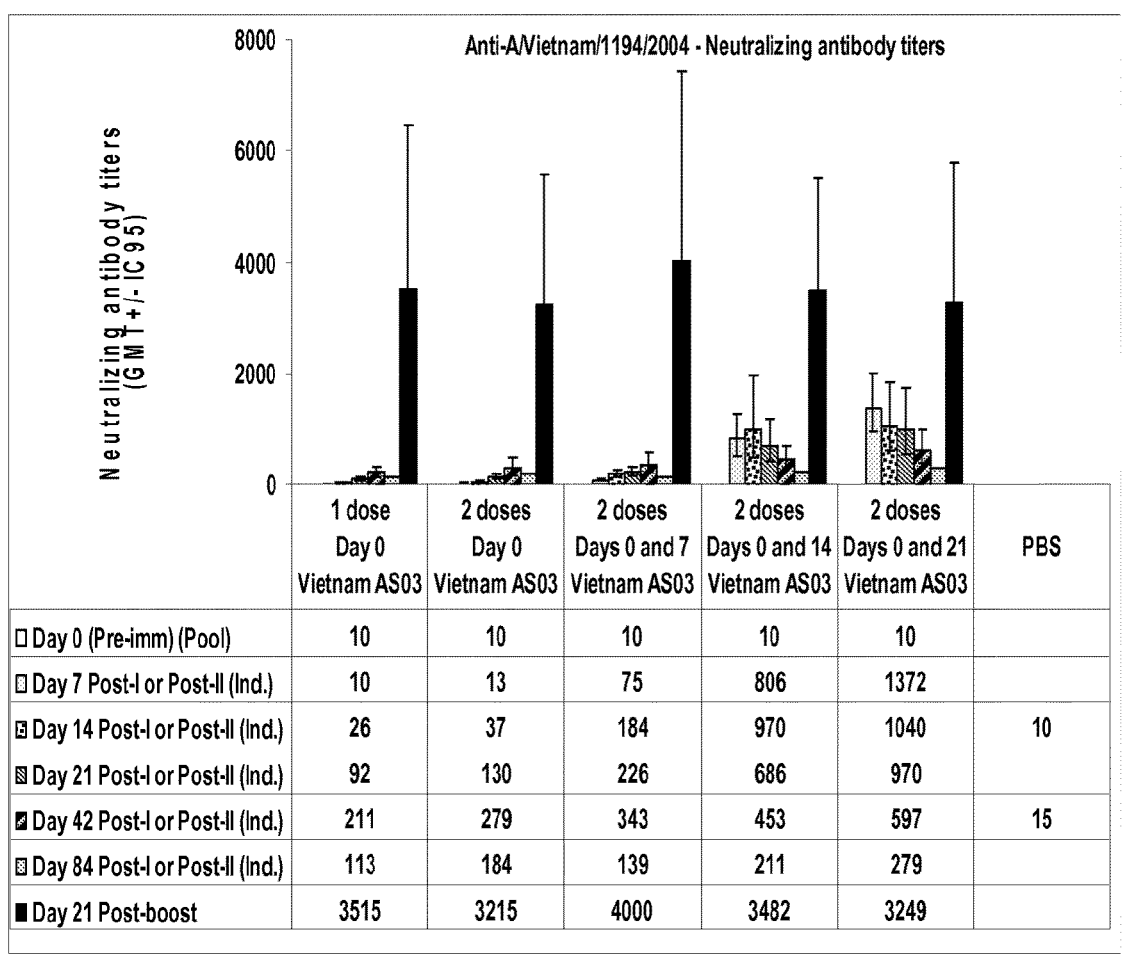

FIG. 10  HI response against A/Indonesia/05/2005 in C57Bl/6 mice
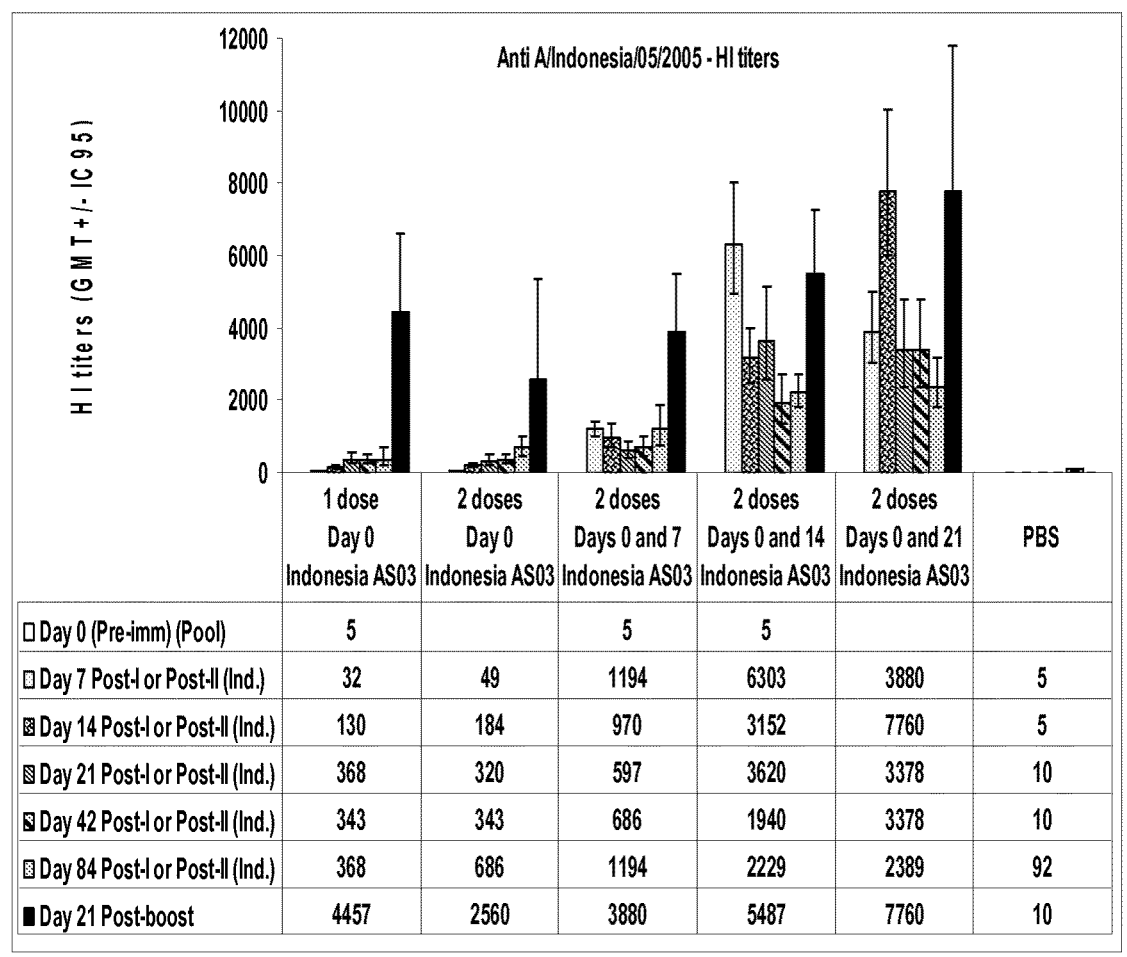

FIG. 11 Neutralizing antibody response against A/Indonesia/05/2005 in C57Bl/6 mice

| | 1 dose Day 0 Indonesia AS03 | 2 doses Day 0 Indonesia AS03 | 2 doses Days 0 and 7 Indonesia AS03 | 2 doses Days 0 and 14 Indonesia AS03 | 2 doses Days 0 and 21 Indonesia AS03 | PBS |
|---|---|---|---|---|---|---|
| Day 0 (Pre-imm) (Pool) | 20 | | 20 | 20 | | |
| Day 7 Post-I or Post-II (Ind.) | 37 | 40 | 557 | 7760 | 7760 | |
| Day 14 Post-I or Post-II (Ind.) | 98 | 139 | 1382 | 7760 | 9554 | 10 |
| Day 21 Post-I or Post-II (Ind.) | 299 | 485 | 1810 | 6303 | 19698 | |
| Day 42 Post-I or Post-II (Ind.) | 1249 | 1689 | 2765 | 8830 | 6964 | 40 |
| Day 84 Post-I or Post-II (Ind.) | 686 | 905 | 1338 | 3958 | 5436 | 10 |
| Day 21 Post-boost | 22627 | 16000 | 18379 | 21112 | 29857 | 250 |

INFLUENZA COMPOSITION

CROSS-REFERENCE TO RELATED APPLICATIONS

This application is a national stage under §371 of International Application No. PCT/EP2008/066815 filed 4 Dec. 2008. This application claims benefit of the earlier filing date of U.S. Provisional Applications No. 60/992,899 filed 6 Dec. 2007, and No. 61/055,569, filed on 23 May 2008, which applications are incorporated herein by reference in their entirety

COPYRIGHT NOTIFICATION PURSUANT TO 37 C.F.R. 6 1.71(E)

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

The present invention relates to influenza vaccine formulations and accelerating primary vaccination regimes for immunising against influenza disease, their use in medicine, in particular their use in promoting effective immune responses to various antigens, and to methods of preparation. In particular, the invention relates to two-doses accelerated pandemic or seasonal primary immunisation regimes with influenza immunogenic compositions, either unadjuvanted or in combination with an oil-in-water emulsion adjuvant, and to accelerated immunisation regimes.

BACKGROUND

Influenza is an acute, contagious respiratory disease caused by influenza viruses which is spread through respiratory droplet transmission. Uncomplicated influenza is characterized by the abrupt onset of constitutional and respiratory symptoms which usually resolve within a week. In certain persons, influenza can aggravate existing medical conditions and potentially lead to life-threatening complications. Influenza viruses are one of the most ubiquitous viruses present in the world, affecting both humans and livestock. Influenza also has a significant impact on the elderly and on the very young. Influenza results in an economic burden, morbidity and even mortality, which are significant.

Influenza viruses are enveloped negative-sense RNA viruses with a segmented genome belonging to the Orthomyxoviridae family. They are classified on the basis of their core proteins into three distinct types: A, B, and C [Cox N J, Fukuda K. Influenza. *Infect. Dis. Clin. North Am.* 1998; 12:27-38]. Influenza A viruses can infect a range of mammalian and avian species, whereas types B and C are essentially restricted to human beings. Influenza A and B viruses are mainly responsible for human disease with type A being the most pathogenic. The main antigenic determinants of influenza A and B viruses are two surface glycoproteins: neuraminidase (NA) and hemagglutinin (HA), both capable of eliciting immune response in human beings. HA is involved in receptor binding and membrane fusion. NA facilitates cleavage of virus progeny from infected cells, prevents viral aggregation, and aids movement through the mucosal respiratory-tract epithelium.

Virus strains are classified according to host species of origin, geographical site, year of isolation, serial number, and, for influenza A, by serological properties of HA and NA subtypes. Sixteen HA subtypes (H1-H16) and nine NA subtypes (N1-N9) have been identified for influenza A viruses [Webster R G et al. Evolution and ecology of influenza A viruses. *Microbiol. Rev.* 1992; 56:152-179; Fouchier R A et al. Characterization of a Novel Influenza A Virus Hemagglutinin Subtype (H16) Obtained from Black-Headed Gulls. *J. Virol.* 2005; 79:2814-2822). Viruses containing all HA and NA subtypes have been recovered from aquatic birds, but only three HA subtypes (H1, H2, and H3) and two NA subtypes (N1 and N2) have established stable lineages in the human population since 1918. Only one subtype of HA and one of NA are recognised for influenza B viruses.

Interpandemic influenza vaccines are currently mainly prepared from virus that is grown in fertile hens' eggs and are either inactivated or live attenuated influenza vaccine. Inactivated flu vaccines are composed of three possible forms of antigen preparation: inactivated whole virus, sub-virions where purified virus particles are disrupted with detergents or other reagents to solubilise the lipid envelope (so-called "split" vaccine) or purified HA and NA (subunit vaccine). These inactivated vaccines are currently given intramuscularly (i.m.), subcutaneously (s.c), or intranasally (i.n.). In accordance with World Health Organization (WHO) recommendations, seasonal influenza vaccines usually contain 45 μg of HA antigen from three co-circulating human strains (as measured by single radial immunodiffusion (SRD) (J. M. Wood et al.: An improved single radial immunodiffusion technique for the assay of influenza haemagglutinin antigen: adaptation for potency determination of inactivated whole virus and subunit vaccines. J. Biol. Stand. 5 (1977) 237-247; J. M. Wood et al., International collaborative study of single radial diffusion and immunoelectrophoresis techniques for the assay of haemagglutinin antigen of influenza virus. J. Biol. Stand. 9 (1981) 317-330)). They generally contain antigens derived from two influenza A virus strains and one influenza B strain (e.g. H1N1, H3N2 and B). A standard 0.5 ml injectable dose in most cases contains (at least) 15 μg of haemagglutinin antigen component from each strain.

Vaccination plays a critical role in controlling annual influenza epidemics. Furthermore, during a pandemics, antiviral drugs may not be sufficient or effective to cover the needs and the number of individuals at risk of influenza will be greater than in interpandemic periods, therefore the development of a suitable vaccine with the potential to be produced in large amounts and with efficient distribution and administration potential is essential. Therefore, in the event of pandemics, vaccination will be instrumental in the strategy to protect the human population from a newly emerging pandemic influenza strain. Therefore, rapid development of a pandemic vaccine is of particular urgency. Means to reduce the severity of the pandemics when it occurs are still needed. Prevention and control of the pandemics will largely depend on the rapid production and worldwide distribution of strain-specific pandemic vaccines.

Besides the need to develop effective candidate 'pandemic-like' vaccines or "pre-pandemic" vaccines, there is a crucial need to develop effective and appropriate vaccination strategies, in order to protect immunologically naïve people, and ultimately an immunologically naïve population, against influenza illness and fatality. In particular there is a need to develop appropriate vaccination strategies 1) to protect the workers involved in the production of a vaccine derived from a highly pathogenic avian virus, or 2) to rapidly protect vulnerable populations such as the pediatric or the elderly population against seasonal or pandemic influenza virus.

STATEMENT OF INVENTION

In one embodiment of the invention, it is provided for the use of an influenza virus or antigenic preparation thereof in the manufacture of an immunogenic composition for a two-dose primary vaccination of a human individual or population against influenza, wherein said composition is prepared for administration of the two primary doses at an interval of less than 14 days. In a related aspect, the invention provides for a two-dose primary immunogenic composition comprising an influenza virus or antigenic preparation thereof for promoting an immune response in a human individual or population against influenza, wherein said composition is prepared for administration of the two primary doses at an interval of less than 14 days. In another related aspect, the invention provides for a method of inducing a primary immune response against influenza virus in a human individual or population, said method comprising the administration of two primary doses, at an interval of less than 14 day, of an immunogenic composition comprising an influenza virus or antigenic preparation thereof.

In another embodiment, the invention provides for the use of an influenza virus or antigenic preparation thereof in the manufacture of a two-dose primary immunogenic composition as defined herein, for the reduction of the severity or the prevention of influenza infections caused by an influenza strain which is an antigenic variant of the strain present in the primary immunogenic composition. In a related aspect, the invention provides for a two-dose primary immunogenic composition comprising an influenza virus or antigenic preparation thereof as herein defined claimed, for use in the reduction of the severity or the prevention of influenza infections caused by an influenza strain which is an antigenic variant of the strain present in the primary immunogenic composition. In another related aspect, the invention provides for a method of reducing the severity or preventing of influenza infections caused by an influenza strain, wherein the primary composition is a two-dose primary immunogenic composition as defined herein, and wherein the influenza infection is caused by a drift-variant of the strain present in said primary immunogenic composition.

In still another embodiment, the invention provides for the use of an influenza virus or antigenic preparation thereof in the manufacture of an immunogenic composition for revaccination against influenza of humans or a human population previously immunised as herein defined. In a relates aspect, the invention provides for an immunogenic composition comprising an influenza virus or antigenic preparation thereof for revaccination against influenza of a human individual or population previously immunised as herein defined. In another related aspect, the invention provides for a method of revaccinating a human individual or population against influenza previously immunised as herein defined, said method comprising administering to said human or population an immunogenic composition comprising an influenza virus or antigenic preparation thereof.

In a further embodiment, the invention provides a kit comprising at least the following two components: (i) a first dose of influenza virus or antigenic preparation thereof optionally formulated with an adjuvant; and (ii) a first dose of influenza virus or antigenic preparation thereof optionally formulated with an adjuvant, wherein said two-doses are for administration within an interval of less than 14 days.

Throughout the document, will be interchangeably used: (a) the use of a influenza virus antigen or antigenic preparation thereof in the manufacture of a composition as herein defined for prevention of influenza infection or disease, (b) a method of treatment of humans using the claimed composition, and (c) a composition as herein defined for use in the prevention of influenza infection or disease, will be interchangeably used.

Other aspects and advantages of the present invention are described further in the following detailed description of preferred embodiments thereof.

BRIEF DESCRIPTION OF THE DRAWINGS

FIG. 1 illustrates the GMTs HI antibody titres against A/Vietnam/1194/2004 (H5N1) vaccine strain and against A/Indonesia/05/2005 (H5N1) strain in a human clinical trial.

FIG. 2 illustrates the seroconversion rates for H5N1 HI antibody titer against H5N1 A/Vietnam/1194/2004 and A/Indonesia/05/2005 at D21 and D42 in a human clinical trial.

FIG. 3 illustrates the seroprotection rates for the H5N1 HI antibody titer against H5N1 A/Vietnam/1194/2004 and A/Indonesia/05/2005 at D21 and D42 post-vaccination in a human clinical trial.

FIG. 4 illustrates the seroconversion factors for H5N1 HI antibody titer against H5N1 A/Vietnam/1194/2004 and A/Indonesia/05/2005 at D21 and D42 post-vaccination in a human clinical trial.

FIG. 5 illustrates the seroconversion rates for H5N1 HI antibody titer against H5NI A/Vietnam/1194/2004 at D21 and D42, analysed by pre-vaccination sero-status in a human clinical trial.

FIG. 6 illustrates the seroprotection rates for H5N1 HI antibody titer against H5NI A/Vietnam/1194/2004 at D21 and D42, analysed by pre-vaccination sero-status in a human clinical trial.

FIG. 7A to E illustrate the CMI response against H5N1 vaccine strain A/Vietnam/1194/2004 (Influenza-specific CD4 T-cells) in a human clinical trial.

FIG. 8 illustrates the HI response against A/Vietnam/1194/2004 in C57Bl/6 mice.

FIG. 9 illustrates the neutralizing antibody response against A/Vietnam/1194/2004 in C57Bl/6 mice.

FIG. 10 illustrates the HI response against A/Indonesia/05/2005 in C57Bl/6 mice.

FIG. 11 illustrates the neutralizing antibody response against A/Indonesia/05/2005 in C57Bl/6 mice.

DETAILED DESCRIPTION

It is one object of the present invention to provide for an accelerated primary vaccination schedule with a pandemic (e.g. H5N1) monovalent influenza vaccine. It is another object of the present invention to provide for an accelerated primary vaccination schedule with a seasonal multivalent influenza vaccine, specifically in infants, children or elderlies.

In first aspect of the present invention, there is provided a two-doses primary immunogenic composition comprising an influenza virus or antigenic preparation thereof for primary immunization of an individual or a population against influenza, wherein the two primary doses are administered at an interval of less than 14 days, or at a 0- to 14-day interval, in particular at a 0- to 10-day interval, or at a 0- to 7-day interval, or at a 0- to 3-day interval. The invention further relates to the use of an influenza virus or antigenic preparation thereof in the manufacture of a monovalent or multivalent e.g. bivalent, trivalent or quadrivalent adjuvanted immunogenic composition for a two-dose primary immunisation of a human individual or population against influenza, wherein the two primary doses are administered at an interval of less than 14 days, or at a 0- to 14-day interval, in particular at a 0- to 10-day interval, or at a 0- to 7-day interval, or at a 0- to 3-day interval. A 0-day interval is taken to mean two primary doses administered the same day either at the same time or at two different times on the same day, e.g. morning and afternoon. When the two injections are made at about the same time they will advantageously be made at two different injection sites in the subject.

In a related aspect the invention relates to a method of inducing a immune response, in particular a primary immune response, against influenza virus in a human individual or population, said method comprising the administration of two doses of a monovalent adjuvanted immunogenic composition comprising an influenza virus or antigenic preparation thereof and wherein the two doses are administered at an interval of less than 14 days, or at a 0- to 14-day interval, in particular at a 0- to 10-day interval, or at a 0- to 7-day interval, or at a 0- to 3-day interval.

In one specific embodiment, said two-doses primary immunogenic composition primes i.e. said individual or population against influenza, in other words promotes an immune response in a naïve or immuno-compromised human individual or population.

In a second aspect of the present invention, there is provided a monovalent or multivalent e.g. bivalent, trivalent or quadrivalent two-dose primary immunogenic composition comprising an influenza virus or antigenic preparation thereof as herein defined, for use in the reduction of the severity or the prevention of influenza infections caused by an influenza strain which is a an antigenic variant of the strain present in said primary immunogenic composition. The invention further relates to the use of an influenza virus or antigenic preparation thereof in the manufacture of a monovalent or multivalent two-dose primary immunogenic composition as herein defined, for the reduction of the severity or the prevention of influenza infections caused by an influenza strain which is an antigenic variant of the strain present in said primary immunogenic composition.

In a related aspect, the invention relates to a method of reducing the severity or preventing of influenza infections caused by an influenza strain, wherein the primary composition is a monovalent or multivalent e.g. trivalent or quadrivalent two-dose primary immunogenic composition as herein defined, and wherein the influenza infection is caused by an antigenic variant of the strain present in said primary immunogenic composition. In any one of the three aspects of the invention, said variant influenza virus strain may be a antigenic drift-variant or and antigenic shift-variant.

In a third aspect of the present invention, there is provided an immunogenic composition comprising an influenza virus or antigenic preparation thereof for revaccination of a human individual or population previously immunised or primed with a monovalent or multivalent e.g. bivalent, trivalent or quadrivalent two-dose primary immunogenic composition administered according to the accelerated schedule as defined above. The invention further relates to the use of an influenza virus or antigenic preparation thereof in the manufacture of an immunogenic composition for revaccination of humans previously immunised or primed with a monovalent or multivalent e.g. bivalent, trivalent or quadrivalent two-dose primary immunogenic composition administered according to the accelerated schedule as defined above.

In a related aspect, the invention relates to a method of revaccinating a human individual or population against influenza virus previously immunised or primed with a monovalent or multivalent e.g. bivalent, trivalent or quadrivalent two-dose primary immunogenic composition administered according to the accelerated schedule as defined above, said method comprising administering to said human or population an immunogenic composition comprising an influenza virus or antigenic preparation thereof.

In one embodiment the primary composition for use according to the invention is adjuvanted. In a specific embodiment, the adjuvant is an oil-in-water emulsion-based adjuvant or adjuvant system. In one embodiment the oil-in-water emulsion comprises a metabolisable oil and an emulsifying agent, and optionally a sterol and/or a tocol such as alpha-tocopherol. In a another specific embodiment, said oil-in-water emulsion adjuvant comprises at least one metabolisable oil in an amount of 0.5% to 20% of the total volume, and has oil droplets of which at least 70% by intensity have diameters of less than 1 µm. Suitably said a tocopherol, such as alpha tocopherol, is present in an amount of 1.0% to 20%, in particular in an amount of 1.0% to 5% of the total volume of said immunogenic composition. In a specific embodiment, the adjuvanted immunogenic composition for use in the present invention comprises an influenza virus antigen or antigenic composition and an adjuvant composition comprising or consisting of an oil-in-water emulsion, wherein said oil-in-water emulsion comprises 0.25-1.25% (v/v) squalene, 0.25-1.25% (v/v) tocol and 0.1-0.7% (v/v) emulsifying agent.

In one embodiment, the influenza composition is monovalent, i.e. comprises a single influenza virus strain or antigenic preparation thereof. In another embodiment, the influenza composition is multivalent e.g. trivalent or quadrivalent. In a specific embodiment, each dose of the two-doses primary immunogenic composition, whether monovalent or multivalent, comprises at least one distinct influenza virus strain or antigenic preparation thereof.

In another specific embodiment, said influenza virus antigen or antigenic preparation thereof is from a pandemic influenza virus strain. Suitable strains according to the invention are in particular avian (bird) influenza strains or porcine strains. Suitable pandemic strains are, but not limited to: H5N1 (the highly pathogenic avian H5N1 strain, now endemic in many bird species across the world, is a candidate pandemic strain according to this invention): H5N1, H9N2, H5N8, H5N9, H7N4, H7N7, H2N2, H10N7, H5N2, H5N3, H7N2, H7N1, H7N3. The influenza virus may be produced in embryonated eggs, in plans, in cell culture, or may be recombinantly produced. Suitably the influenza virus antigen is produced in embryonated eggs or in cell culture.

In a further aspect there is provided a method for priming a human population or individual against one pandemic influenza virus strain followed by revaccination of said human or population against an antigenic variant influenza virus strain, said method comprising administering to said human (i) a first two-doses primary immunogenic composition comprising an influenza virus or antigenic preparation thereof from a pandemic influenza virus strain and an oil-in-water emulsion adjuvant, and (ii) a second boosting immunogenic composition comprising a influenza virus strain which is an antigenic variant of said first influenza virus strain. In one embodiment said antigenic variant strain used for revaccination is also a pandemic strain, specifically it is a drift-variant strain such as from a different clade, a different subclade, or a shift-variant strain such as from a different subtype, than that used in the primary vaccination. In another embodiment said antigenic variant strain used for revaccination is a currently circulating (seasonal) strain such as H1N1 or H3N2. In another embodiment said antigenic variant strain used for revaccination is part of a multivalent composition which comprises, in addition to a pandemic influenza virus antigenic variant, at least one circulating (seasonal) influenza virus strain. In particular, said pandemic influenza virus strain is part of a bivalent, or a trivalent, or quadrivalent composition comprising in addition to said pandemic strain at least one, two or three seasonal strains, respectively. In a specific embodiment the two doses primary immunization consists of two doses administered on the same day, or at a 0 to 3 day interval, or at a 0 to 7 day interval, or at a 0 to 10 day interval, or at a 0 to 14 day interval. An adjuvant may or may not be present.

The present invention covers a two-doses accelerated vaccination schedule for primary immunisation against influenza of a naïve or immuno-compromised human individual or population. This accelerated schedule of immunisation is aimed at being capable of achieving rapidly some level of protection against morbidity/mortality caused by an influenza strain to which the target individual or population is naïve, such as a pandemic strain, or by an influenza strain against which the target individual or population has no or weak memory, such as a seasonal strain in children, infants and immuno-compromised adults and elderlies.

In one embodiment, the two-doses primary influenza composition comprises a low amount of a pandemic influenza virus or antigenic preparation thereof, together with an oil-in-water emulsion adjuvant comprising a metabolisable oil and an emulsifying agent, and optionally a sterol and/or a tocol such as alpha-tocopherol.

Suitably the two-doses primary immunogenic composition is capable of inducing at least one of: a humoral immune response, a T-cell immune response such as a CD4 T-cell immune response and a B cell memory response against said virus or antigenic preparation thereof in a human or population as herein defined.

In a specific embodiment said immune response is improved compared to that obtained with the un-adjuvanted composition administered according to the same schedule. Suitably the improvement is at least a 2-fold, at least a 3-fold, at least 10-fold increase of said immune response.

In another embodiment said immune response obtained after the accelerated immunisation schedule is similar to or at least not statistically significantly lower than that obtained after immunisation with the same immunogenic composition administered twice at the usual 0-21 or 0-28 day interval.

In a specific embodiment, said humoral immune response in terms of anti-haemagglutinin antibodies specific for the vaccine-homologous virus, meets at least one, or at least two, or all three of the immunological criteria established for influenza vaccines by the European Committee for Medicinal Products for Human Use (CHMP) or FDA regulatory criteria for influenza vaccine efficacy, as measured 7 days, 14 days or 21 days after the second dose, or after two doses administered the same day, e.g. at two different injection sites in one subject.

It is a specific object of the invention that at least one, suitably two FDA or EU criteria is (are) met after the two doses of vaccine according to the accelerated schedule as herein defined. Efficacy criteria for the composition according to the present invention are further detailed below (see Table 1 and below under "efficacy criteria"). Suitably said composition is administered parenterally, in particular via the intramuscular or the sub-cutaneous route.

The formulations adjuvanted with an oil-in-water emulsion adjuvant as herein defined will advantageously be used to induce anti-influenza CD4 or CD8 T cell response, capable of detection of influenza epitopes presented by MHC class II molecules. The accelerated priming scheme with the adjuvanted formulations as herein defined will advantageously induce a cross-reactive immune response, i.e. detectable immunity (humoral and/or cellular) against an antigenic variant influenza virus strain or against a range of antigenic variant influenza virus strain. The adjuvanted formulations will advantageously be effective to target the humoral and/or the cell-mediated immune system in order to increase responsiveness against homologous and antigenic variant influenza strains such as drift-variant or shift-variant strains (upon vaccination and infection). They will also advantageously be used to induce, after one or two doses, a cross-priming strategy, i.e. induce "primed" immunological memory facilitating response upon revaccination with one dose of a composition comprising an antigenic variant strain. In this case i.e. after a course of prepandemic vaccine (administered in two doses according to the accelerated schedule during the early phases of pandemic virus progression), a recipient would need just one dose of pandemic vaccine including the same influenza virus strain or an antigenic variant thereof, to be fully protected against the actual pandemic strain once the pandemic onset is confirmed.

The accelerated primary immunisation strategy according to the invention have several advantages:
1) An improved immunogenicity compared to that obtained with an un-adjuvanted composition, designed to overcome the potential weak immunogenicity of the antigen in a naïve population, and leading to the immunological priming of that previously naïve population; this improved immunogenicity would be afforded much more quickly than that obtained with the usual schedule 0-21 days.
2) An improved immune response to less immunogenic influenza strains which characterise some pandemic strains;
3) An improved cross-protection profile: increased cross-reactivity, cross-protection against antigenic variant (e.g. drift- or shift-variant) influenza strains allowing the set-up of an accelerated cross-priming strategy where they can be used as pre-pandemic vaccines further allowing only one dose of a pandemic vaccine to be required to enhance the protection against the actual pandemic strain;
4) By reaching any or all of these further advantages with a reduced antigen dosage, they will ensure an increased capacity in case of emergency or for preparedness of a pandemic situation (antigen-sparing in the pandemic situation) and offering a possibility of higher number of vaccine doses available to the population.

According to further aspects of the present invention, the claimed immunization schedule is capable to induce seroprotection and seroconversion to a degree no lower than that provided for by the EU (CHMP) or FDA (CBER) requirements for vaccine influenza strains. This will be further detailed below (see Table 1 and below under "efficacy criteria").

Terms

Unless otherwise explained, all technical and scientific terms used herein have the same meaning as commonly understood by one of ordinary skill in the art to which disclosure belongs. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science LtD., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a", "an", and "the" include plural referents unless context clearly indicates otherwise. Similarly, the word "or" is intended to include "and" unless the context clearly indicates otherwise. Numerical limitations given with respect to concentrations or levels of a substance, suc as an antigen, are intended to be approximate. Thus, where a concentration is indicated to be at least (for example) 200 µg, it is intended that the concentration be understood to be at least approximately "about" or "~" 200 µg.

Although methods and materials similar or equivalent to those describes herein can be used in the practice or testing of this disclosure, suitable methods and materials are described below. The term "comprises" means "includes". Thus, unless the context requires otherwise, the word "comprises", and variations such as "comprise" and "comprising" will be understood to imply the inclusion of a stated compound or composition (e.g. polypeptide or antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example".

The term "primary immunisation" or "primary vaccination" means in its broadest sense first immunization or first vaccination". When the first vaccination takes place in a vaccination regimen comprising a first and a second immunization, the first and the second immunization are spaced by at least one month. In an immunologically naïve human or population, the first immunisation may lead to the priming of the immune system, i.e. said human or human population will become seropositive (to the vaccine influenza virus strain) as a result of the primary vaccination.

For the avoidance of doubt the terms 'comprising', 'comprise' and 'comprises' herein is intended by the inventors to be optionally substitutable with the terms 'consisting of', 'consist of', and 'consists of', respectively, in every instance.

Other terms and explanations are provided in the context of this disclosure.

Influenza Viral Strains and Antigens

Influenza A viruses are continuously evolving and as a consequence, undergo antigenic variation [Johnson N P, Mueller J. Updating the accounts: global mortality of the 1918-1920 "Spanish" influenza pandemic. *Bull. Hist. Med.* 2006; 76:105-115]. During inter-pandemic periods, influenza viruses that circulate are related to those from the preceding epidemic. The viruses spread among people with varying levels of immunity from infections earlier in life. Such circulation, over a period of usually 2-3 years, and a lack of effective proofreading by the viral RNA polymerase, leads to a high rate of transcription errors that can result in amino-acid substitutions in surface glycoproteins and that promotes the selection of new strains that have changed enough to cause an epidemic again among the general population; this process is termed 'antigenic drift'.

The segmented viral genome allows for a second type of antigenic variation. At unpredictable intervals, if two influenza viruses simultaneously infect a host cell, genetic reassortment will result in novel influenza viruses with a key surface antigen, the haemagglutinin, of a totally different subtype from strains circulating the season before. Here, the resulting antigens can vary from 20% to 50% from the corresponding protein of strains that were previously circulating in humans. This phenomenon, called "antigenic shift" may generate a novel virus with new surface or internal proteins which escapes 'herd immunity' and establishes pandemics.

These antigenic changes, both 'drifts' and 'shifts' are unpredictable and may have a dramatic impact from an immunological point of view as they eventually lead to the emergence of new influenza strains and that enable the virus to escape the immune system causing the well known, almost annual, epidemics.

In addition to annual epidemics, newly emerging influenza viruses, with a new haemagglutinin type or subtype in the (naïve) human population capable of efficient human-to-human transmission, have caused pandemics in the past, i.e. sudden, global epidemics in all age groups with higher infectivity and mortality rates. The last century has seen three influenza pandemics, the "Spanish Flu" in 1918-1919, responsible for the deaths of 20 to 50 million people worldwide, the "Asian Flu" in 1957 and the "Hong Kong Flu" in 1968.

Human pandemic influenza viruses emerge when one or more avian influenza virus genes, previously unseen by the majority of humans, are incorporated into a human influenza virus and in addition, acquire the ability to spread efficiently between humans. In other words, an influenza pandemics occurs when a new influenza virus appears against which the human population has no immunity. It is thought that at least the past pandemics have occurred when an influenza virus from a different species, such as an avian or a porcine influenza virus, has crossed the species barrier. If such viruses have the potential to spread from human to human, they may spread worldwide within a few months to a year, resulting in a pandemic.

WHO has defined several phases of pandemic influenza ("WHO global preparedness plan, WHO, Geneva, 2005, whole document and in particular Table 1—available online at http://www.who.int/csdresources/publications/influenza/WHO_CDS_CSR_GIP_2005_5.pd f), from Phases 1 and 2 (interpandemic period) to Phase 3 to 5 (pandemic alert) leading to Phase 6 (pandemic period). Phase 3 is when a new influenza subtype is identified in a human case. In the present disclosure it will be referred to a pandemic influenza virus strain generically as a strain that can cause a pandemic outbreak at any stage of virus progression, from early stages of progression (pre-pandemic or potential pandemic virus strain) such as in Phase 3 to 5 or confirmed pandemic stage (pandemic strain) such as in Phase 6.

The features of a pandemic influenza virus strain are: it contains a new haemagglutinin compared to the haemagglutinin in the currently circulating strains, which may or not be accompanied by a change in neuraminidase subtype; it is capable of being transmitted horizontally in the human population; and it is pathogenic for humans. A new haemagglutinin can be one which has not been evident in the human population for an extended period of time, probably for at least a decade such as H2 which last circulated in 1957, or it may be a haemagglutinin that has never been circulating in the human population before, for example H5, H9, H7 or H6 which are usually found in birds. In these cases, a large proportion (in the case of H2 for example) or the entire (in the case of H5, H7, H6 or H9) population is immunologically naïve to the pandemic influenza virus strain. At present, the influenza A virus that has been identified by the WHO as one that potentially could cause an influenza pandemics in humans is the highly pathogenic H5N1 avian influenza virus. Therefore, the pandemic vaccine for use according to the invention will suitably comprise H5N1 virus. Other suitable strains for inclusion into the claimed composition are H9N2, H7N1, H7N7 or H2N2.

In one embodiment, an influenza virus or antigenic preparation thereof for use according to the present invention may be a split influenza virus or split virus antigenic preparation thereof. In an alternative embodiment the influenza preparation may contain another type of inactivated influenza antigen, such as inactivated whole virus or recombinant and/or purified subunit vaccine, an influenza virosome or a virus-like particle recombinantly produced. In a still further embodiment, the influenza virus may be a live attenuated influenza preparation.

In some embodiments of the invention, it is referred to a variant influenza virus strain. By "variant" strain is meant "heterologous" strain. It may be an antigenic drift-variant such as of a virus strain from a different glade (e.g. clade 1 or 2) or subclade (e.g. subclades of clade 2 such as 2.1, 2.2, 2.3, 2.4 and 2.5), or an antigenic shift-variant such as of a distinct sub-type (e.g. H5, H7 or H9). As the case may be, and this will be clear from the disclosure, it can be a circulating strain heterologous to the vaccine strain (either for primary vaccination or revaccination), or when referring to a prime-boost vaccination concept for example, heterologous to the strain included in the composition for the primary vaccination or revaccination.

A split influenza virus or split virus antigenic preparation thereof for use according to the present invention is suitably an inactivated virus preparation where virus particles are disrupted with detergents or other reagents to solubilise the lipid envelope. Split virus or split virus antigenic preparations thereof are suitably prepared by fragmentation of whole influenza virus, either infectious or inactivated, with solubilising concentrations of organic solvents or detergents and subsequent removal of all or the majority of the solubilising agent and some or most of the viral lipid material. By split virus antigenic preparation thereof is meant a split virus preparation which may have undergone some degree of purification compared to the split virus whilst retaining most of the antigenic properties of the split virus components. For example, when produced in eggs, the split virus may be depleted from egg-contaminating proteins, or when produced in cell culture, the split virus may be depleted from host cell contaminants. A split virus antigenic preparation may comprise split virus antigenic components of more than one viral strain. Vaccines containing split virus (called 'influenza split vaccine') or split virus antigenic preparations generally contain residual matrix protein and nucleoprotein and sometimes lipid, as well as the membrane envelope proteins. Such split virus vaccines will usually contain most or all of the virus structural proteins although not necessarily in the same proportions as they occur in the whole virus.

Alternatively, the influenza virus may be in the form of a whole virus vaccine. This may prove to be advantageous over a split virus vaccine for a pandemic situation as it avoids the uncertainty over whether a split virus vaccine can be successfully produced for a new strain of influenza virus. For some strains the conventional detergents used for producing the split virus can damage the virus and render it unusable. Although there is always the possibility to use different detergents and/or to develop a different process for producing a split vaccine, this would take time, which may not be available in a pandemic situation. In addition, there is also a greater vaccine production capacity for whole virus than for split virus since considerable amounts of antigen are lost during additional purification steps necessary for preparing a suitable split vaccine.

In another embodiment, the influenza virus preparation thereof is in the form of a sub-unit influenza vaccine. Sub-unit influenza vaccines generally contain the two major envelope proteins, HA and NA, optionally with other virus components and may have an additional advantage over whole virion vaccines as they are generally less reactogenic, particularly in young vaccinees. In another embodiment said sub-unit vaccine contains M2 or M2e envelope protein, either alone or in combination with HA, NA or both. Sub-unit vaccines and components thereof can be produced recombinantly or synthetised chemically, or purified from disrupted viral particles.

In another embodiment, the influenza virus preparation is in the form of a virosome. Virosomes are spherical, unilamellar vesicles which retain the functional viral envelope glycoproteins HA and NA in authentic conformation, intercalated in the virosomes' phospholipids bilayer membrane.

In another embodiment the influenza virus preparation may be in the form of a virus-like particle.

Said influenza virus or antigenic preparation thereof may be produced in eggs or cell culture. They may also be produced in other systems such as insect cells, mammalian cells, avian cells, plants, yeast or bacteria or be recombinantly produced.

For example, the influenza virus antigen or antigenic preparations thereof according to the invention may be produced using the conventional embryonated egg method, by growing influenza virus in eggs and purifying the harvested allantoic fluid. Eggs can be accumulated in large numbers at short notice. Alternatively, they may be produced by any of the new generation methods using tissue culture to grow the virus or express recombinant influenza virus surface antigens. Suitable cell substrates for growing the virus include for example dog kidney cells such as MDCK or cells from a clone of MDCK, MDCK-like cells, monkey kidney cells such as AGMK cells including Vero cells, suitable pig cell lines, or any other mammalian cell type suitable for the production of influenza virus for vaccine purposes. Suitable cell substrates also include human cells e.g. MRC-5 or Per-C6 cells. Suitable cell substrates are not limited to cell lines; for example primary cells such as chicken embryo fibroblasts and avian cell lines such as the chicken EB14® or duck EB 24® or EB 66® cell line are also included.

The influenza virus antigen or antigenic preparation thereof may be produced by any of a number of commercially applicable processes, for example the split flu process described in WO 02/097072, incorporated herein by reference.

The influenza preparation may be prepared in the presence of a preservative such as thiomersal. Suitably the preservative, in particular thiomersal, is present at a concentration of around 100 µg/ml. Alternatively, the influenza preparation is prepared in the presence of low level of preservative in particular thiomersal, such as a concentration not exceeding 20 µg/ml or suitably less than 5 µg/ml. In another suitable alternative embodiment, the influenza preparation is made in the absence of thiomersal. Suitably the resulting influenza preparation is stable in the absence of organomercurial preservatives, in particular the preparation contains no residual thiomersal. In particular the influenza virus preparation comprises a haemagglutinin antigen stabilised in the absence of thiomersal, or at low levels of thiomersal (generally 5 µg/ml or less). Specifically the stabilization of B influenza strain is performed by a derivative of alpha tocopherol, such as alpha tocopherol succinate (also known as vitamin E succinate, i.e. VES). Such preparations and methods to prepare them are disclosed in WO 02/097072.

Alternatively, especially for multi-dose containers, thiomersal or any other suitable preservative is present in order to reduce the contamination risks. This is particularly of relevance for pandemic vaccines, designed to vaccinate as many people as possible in the shortest possible time.

In one embodiment the influenza virus or antigenic preparation thereof and the oil-in-water emulsion adjuvant are contained in the same container. It is referred to as 'one container approach'. In one embodiment the container is a pre-filled syringe or a mono-dose vial or a 10-dose multi-dose container or a 12-dose ampoule. In an alternative embodiment, the influenza virus or antigenic preparation thereof and the oil-in-water emulsion adjuvant are contained in separate containers or containers or units and admixed shortly before or upon administration into the subject. It is referred to as 'two container approach'.

The volume of one dose of the reconstituted adjuvanted influenza candidate vaccine can be between about 0.25-1 ml, and usually corresponds to about 0.5 ml for an adult formulation. Suitably a 0.5 ml adult dose corresponds to about 0.25 ml adjuvant plus about 0.25 ml antigen). Each vaccine dose can contain about 15 µg haemagglutinin (HA). In an alternative embodiment, each vaccine dose contains a low amount of HA, such as an amount of less than about 15 µg of HA, suitably less than about 10 µg. Suitable amounts are about 1.9 µg, about 3.8 µg, about 5 µg, about 7.5 µg, or about 10 µg HA or any suitable amount of HA lower than about 15 µg which would have be determined such that the vaccine composition meets at least one of the efficacy criteria as defined herein. Advantageously an HA dose of about 1 µg of HA or even less such as about 0.5 µg of HA that would allow meeting the regulatory criteria defined above may be used. A vaccine dose of about 1 ml (about 0.5 ml adjuvant plus about 0.5 ml antigen preparation) is also suitable. A vaccine dose of about 0.25 ml (e.g. about 0.125 ml adjuvant plus about 0.125 ml antigen preparation) is also suitable, especially for the pediatric population.

According to the present invention, the influenza strain in the monovalent immunogenic composition as herein defined is a pandemic strain. Suitable strains are, but not limited to: H5N1, H9N2, H5N8, H5N9, H7N4, H7N7, H2N2, H10N7, H5N2, H5N3, H7N2, H7N1, H7N3.

While waiting for the optimally matched (and regulatory-approved) H5N1 pandemic vaccine, pre-pandemic strategy of vaccination is carried out with an adjuvanted vaccine produced with an potential pandemic strain e.g. a H5 strain. Although the strain used for the primary vaccination may turn out to be antigenically distinct or of a different clade compared to that of the strain ultimately causing the pandemic, vaccination according to the formulations and methods disclosed herein will prime people before the spread of the pandemic strain and improve their protection at the time of vaccination with the H5N1 pandemic vaccine. Accordingly in one embodiment, the primary vaccination is made with an adjuvanted immunogenic composition as herein defined, monovalent or multivalent, comprising one pandemic strain such as H5N1 or at least two distinct influenza strains, such as from two different clades of H5N1 or H5N1 and another subtype, such as but not limited to: H5N1, H9N2, H5N8, H5N9, H7N4, H7N7, H2N2, H10N7, H5N2, H5N3, H7N2, H7N1, H7N3, administered according to the accelerated immunization schedule as claimed herein. The revaccination follows with an adjuvanted composition comprising a pandemic influenza strain, which is not necessarily identical to the primary vaccination strain (for example, the pandemic strain may be a heterologous strain, such as a drift-variant strain, to that of the primary vaccination), such as for example a H5 strain from a different clade or even a strain from a different subtype such as H9N2 at the next time point (e.g. after 2 months, 4 months, 6 months or even one year). Since it is impossible to predict a) the timing of a potential pandemic and b) the specific pandemic strain, this strategy relying on the claimed accelerated schedule of immunization with a pandemic strain will provide increased insurance for maximizing magnitude and breadth of protective immune responses at the right time. In these strategies the adjuvant is suitably as defined herein.

In another embodiment the primary vaccination is made with an immunogenic composition, adjuvanted or not, comprising one or more seasonal influenza strain, and optionally comprising one or more pandemic strains.

As said above, overall the human population will be substantially seronegative on a popularion basis to a pandemic strain. Furthermore, certain parties are at an increased risk of becoming infected with influenza in a pandemic situation. The elderly, the chronically ill and small children are particularly susceptible as they may have a decreased capacity at mounting an immune response following vaccination but many young adults and apparently healthy people are also at risk. The accelerated schedule of immunisation may also benefit these populations, in addition to the classical naïve population.

Another group of people who are at increased risk are travelers. People travel more today than ever before and the regions where most new viruses emerge, China and South East Asia, have become popular travel destinations in recent years. This change in travel patterns enables new viruses to reach around the globe in a matter of weeks rather than months or years.

Thus for these groups of people there is a particular need for vaccination to protect against influenza in a pandemic situation or a potential pandemic situation. Suitable pandemic strains are, but not limited to: H5N1, H9N2, H5N8, H5N9, H7N4, H7N7, H2N2, H10N7, H5N2, H5N3, H7N2, H7N1, H7N3.

Oil-in-Water Emulsion Adjuvant

The adjuvant composition of the invention contains an oil-in-water emulsion adjuvant, suitably said emulsion comprises a metabolisable oil in an amount of 0.5% to 20% of the total volume, and having oil droplets of which at least 70% by intensity have diameters of less than 1 µm. The size of the oil droplets, i.e. diameter, can be measured by techniques known in the art such as by use of a sizing instrument, suitably by dynamic light scattering such as the Malvern Zetasizer 4000 or suitably the Malvern Zetasizer 3000HS.

In order for any oil in water composition to be suitable for human administration, the oil phase of the emulsion system has to comprise a metabolisable oil. The meaning of the term metabolisable oil is well known in the art. Metabolisable can be defined as 'being capable of being transformed by metabolism' (Dorland's Illustrated Medical Dictionary, W.B. Sanders Company, 25th edition (1974)). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others. A particularly suitable metabolisable oil is squalene. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly suitable oil for use in this invention. Squalene is a metabolisable oil by virtue of the fact that it is enzymatically transformed during the biosynthesis of cholesterol (Merck index, 10th Edition, entry no. 8619).

Oil in water emulsions per se are well known in the art, and have been suggested to be useful as adjuvant compositions (EP 399843; WO 95/17210).

The specific amounts given below for the components of the oil-in-water emulsion adjuvant, when expressed in % (v/v) of the total volume of the immunogenic composition, are understood to be per one dose of the two-dose immunisation regimen.

In one embodiment the metabolisable oil is present in an amount of 0.5% to 20% (final concentration) of the total volume of the immunogenic composition, suitably an amount of 1.0% to 10% of the total volume, suitably in an amount of 2.0% to 6.0% of the total volume. In a specific embodiment the metabolisable oil is present in an amount of about 0.25-1.25% (v/v) of the total volume of the immunogenic composition.

In a specific embodiment, the metabolisable oil is present in a final amount of about 0.25%, about 0.5%, about 1%, about 3.5% or about 5% of the total volume of the immunogenic composition. In another specific embodiment said oil is squalene. In one aspect, the amount of squalene is about 10.7 mg per vaccine dose, suitably from about 10.4 to about 11.0 mg per vaccine dose. In another aspect the amount of squalene is about 5.35 mg per vaccine dose, suitably from about 5.0 to about 6.0 mg per vaccine dose. In another aspect the amount of squalene is about 2.7 mg per vaccine dose, suitably from 2.5 to 3.0 mg per vaccine dose. In another aspect the amount of squalene is about 1.35 mg per vaccine dose, suitably from about 1.1 to about 1.5 mg per vaccine dose.

Suitably the oil-in-water emulsion systems of the present invention have a small oil droplet size in the sub-micron range. Suitably the droplet sizes will be in the range 120 to 750 nm, suitably sizes from 120 to 600 nm in diameter. Typically the oil-in water emulsion contains oil droplets of which at least 70% by intensity are less than 500 nm in diameter, in particular at least 80% by intensity are less than 300 nm in diameter, suitably at least 90% by intensity are in the range of 120 to 200 nm in diameter.

The oil in water emulsion according to the invention advantageously comprises a sterol and/or a tocol such as tocopherol, in particular alpha tocopherol. Sterols are well known in the art, for example cholesterol is well known and is, for example, disclosed in the Merck Index, 11th Edn., page 341, as a naturally occurring sterol found in animal fat. Other suitable sterols include β-sitosterol, stigmasterol, ergosterol and ergocalciferol. Said sterol is suitably present in an amount of about 0.01% to about 20% (w/v) of the total volume of the immunogenic composition, suitably at an amount of about 0.1% to about 5% (w/v). Suitably, when the sterol is cholesterol, it is present in an amount of between about 0.02% and about 0.2% (w/v) of the total volume of the immunogenic composition, typically at an amount of about 0.02% (w/v) in a 0.5 ml vaccine dose volume.

Tocols (e.g. vitamin E) are also often used in oil emulsions adjuvants (EP 0 382 271 B1; U.S. Pat. No. 5,667,784; WO 95/17210). Tocols used in the oil emulsions (optionally oil in water emulsions) of the invention may be formulated as described in EP 0 382 271 B1, in that the tocols may be dispersions of tocol droplets, optionally comprising an emulsifier, of optionally less than 1 micron in diameter. Alternatively, the tocols may be used in combination with another oil, to form the oil phase of an oil emulsion. Examples of oil emulsions which may be used in combination with the tocol are described herein, such as the metabolisable oils described above.

Suitably alpha-tocopherol or a derivative thereof such as alpha-tocopherol succinate is present. Suitably alpha-tocopherol is present in an amount of between about 0.2% and about 5.0% (v/v) of the total volume of the immunogenic composition, suitably at an amount of about 2.5% (v/v) in a 0.5 ml vaccine dose volume, or 0.5% (v/v) in 0.5 ml vaccine dose volume or about 1.7-1.9% (v/v), suitably about 1.8% in 0.7 ml vaccine dose volume. In a specific embodiment the tocol or alpha-tocopherol is present in an amount of about 0.25-1.25% (v/v) of the total volume of the immunogenic composition. In another specific embodiment, the tocol or alpha-tocopherol is present in a final amount of about 0.5%, about 1%, about 3.57% or about 5% of the total volume of the immunogenic composition. By way of clarification, concentrations given in v/v can be converted into concentration in w/v by applying the following conversion factor: a 5% (v/v) alpha-tocopherol concentration is equivalent to a 4.8% (w/v) alpha-tocopherol concentration. In one aspect, the amount of alpha-tocopherol is about 11.9 mg per vaccine dose, suitably from about 11.6 to about 12.2 mg per vaccine dose. In another aspect the amount of alpha-tocopherol is about 5.95 mg per vaccine dose, suitably from about 5.5 to about 6.5 mg per vaccine dose. In another aspect the amount of alpha-tocopherol is about 3.0 mg per vaccine dose, suitably from about 2.8 to about 3.3 mg per vaccine dose. In another aspect the amount of alpha-tocopherol is about 1.5 mg per vaccine dose, suitably from about 1.25 to about 1.75 mg per vaccine dose.

The oil in water emulsion comprises an emulsifying agent. The emulsifying agent may be present at an amount of about 0.01 to about 5.0% by weight of the immunogenic composition (w/w), suitably present at an amount of about 0.1 to about 2.0% by weight (w/w). Suitable concentrations are about 0.5 to about 1.5% by weight (w/w) of the total composition.

The emulsifying agent may suitably be polyoxyethylene sorbitan monooleate (polysorbate 80 or Tween 80). In a specific embodiment, a 0.5 ml vaccine dose volume contains 1% (w/w) Tween 80, and a 0.7 ml vaccine dose volume contains about 0.7% (w/w) Tween 80. In another specific embodiment the concentration of Tween 80 is about 0.1% or about 0.2% (w/w). In one aspect the amount of polysorbate 80 is about 4.9 mg per vaccine dose, suitably from about 4.6 to about 5.2 mg per vaccine dose. In another aspect, the amount of polysorbate 80 is about 2.4 mg per vaccine dose, suitably from about 2.0 to about 2.8 mg per vaccine dose. In another aspect, the amount of polysorbate 80 is about 1.2 mg per vaccine dose, suitably from about 1.0 to about 1.5 mg per vaccine dose. In another aspect, the amount of polysorbate 80 is about 0.6 mg per vaccine dose, suitably from about 0.4-0.8 mg per vaccine dose.

In one embodiment a vaccine dose for use in the present invention comprises:
  alpha-tocopherol in an amount of about 11.9 mg per vaccine dose, squalene in an amount of about 10.7 mg per vaccine dose, and polysorbate 80 in an amount of about 4.9 mg per vaccine dose;
  an adjuvant composition comprising or consisting of an oil in water emulsion, wherein said oil in water emulsion comprises about 0.25-1.25% (v/v) squalene, about 0.25-1.25% (v/v) tocol and about 0.1-0.7% (v/v) emulsifying agent;
  an adjuvant composition comprising or consisting of an oil in water emulsion, wherein said oil in water emulsion comprises about 0.5-1.25% (v/v) squalene, about 0.6-1.25% (v/v) tocol and about 0.25-0.5% (v/v) emulsifying agent.

The oil-in-water emulsion adjuvant may be utilised with other adjuvants or immuno-stimulants and therefore an important embodiment of the invention is an oil in water formulation comprising squalene or another metabolisable oil, a tocopherol, such as alpha tocopherol, and tween 80. The oil in water emulsion may also contain span 85 and/or Lecithin. Typically the oil in water will comprise from about 2 to about 10% squalene of the total volume of the immunogenic composition, from 2 to 10% alpha tocopherol and from about 0.3 to about 3% Tween 80, and may be produced according to the procedure described in WO 95/17210. Suitably the ratio of squalene:alpha tocopherol is equal or less than 1 as this provides a more stable emulsion. Span 85 (polyoxyethylene sorbitan trioleate) may also be present, for example at a level of about 1%.

Vaccination Regimes

Due to the accelerated primary immunisation schedule disclosed herein and to the immunogenic properties of the primary composition for use in the accelerated priming regimen, it may be possible to establish a proactive and more rapid vaccination strategy against the threat of a human influenza pandemic, including the stockpiling of pre-pandemic vaccine in order to better prepare against the onset of a pandemic. It may also be possible to operate a seasonal influenza primary immunisation in children and infants not previously vaccinated, or in immuno-compromised adults or elderlies.

Specifically, the monovalent prepandemic primary immunogenic composition is one that has been produced, for example through the use of reverse genetics, using a strain of H5N1 (avian flu) selected to be similar to those currently circulating in the bird population and predicted to be associated with the potential to give rise (e.g., through genetic mutation or recombination) to a human pandemic. The immunity developed in response to this pre-pandemic vaccine "primes" or "educates" the immune system and thereby facilitates more rapid development of protective immune responses after encountering the actual pandemic virus strain, thereby leading to a decreased susceptibility to a related pandemic strain of the influenza. Once WHO has confirmed the onset of a pandemic and the final pandemic strain identified (be it a drift-variant strain), the prepandemic vaccination ensures a more rapid and effective immune response to the pandemic vaccine when the latter becomes available.

In a specific embodiment, the accelerated primary immunisation scheme may offer the additional benefit of providing better protection against circulating strains which have undergone a minor or major change in the haemagglutinin (antigenic drift or shift) against which currently available vaccines have no efficacy. Suitably, the two dose administration schedule with an adjuvanted monovalent composition as herein described for the primary vaccination will be capable of providing similar sero-protection, as assessed by the correlates of protection for influenza vaccines, following revaccination against influenza, to that obtained with the vaccination according to a classical 0-21 days schedule.

It is an object of the present invention to induce an immune response in a human individual or human population, in particular in a seronegative (naïve) individual or population, by administering two doses of an influenza immunogenic composition according to an immunisation schedule which is accelerated compared to what is routinely done. This seronegativity may be the result of said subject having never faced such virus or antigen (so-called 'naive' subject) such as a subject facing a pandemic strain. Alternatively, this seronegativity may be the result of said subject having failed to respond to said virus or antigen preparation thereof once encountered, including subjects having failed to respond to a seasonal or a previously administered pandemic influenza virus. Suitably said immune response is obtained in an immunocompromised subject such as an elderly, typically at least 50 years of age, typically 65 years of age or above, or an adult below 65 years of age with a high risk medical condition ('high risk' adult), or a child under the age of nine with no influenza vaccination history, suitably under the age of two.

The second dose of said composition (still considered as 'composition for first vaccination') is administered during the on-going primary immune response and is administered in a short time after the first dose, i.e. an interval shorter than the standard immunisation schedule of two doses administered at a three weeks (21 days) or more interval.

Accordingly, in one embodiment of the invention, the administration of the two primary doses is given at an interval between the two doses of a maximum of 2 weeks (14 days) or less. A suitable interval ranges from 0 days (where the two doses are administered on the same day) to less than 14 days. Advantageously the second dose will be administered between 0-10 days, suitably between 0-7 days after the first dose, or suitably between 0- to 3-day. Suitably the two doses are given 0, 7 or less than 14 days apart. An another suitable interval is any one of: 1, 2, 3, 4, 5, 6, 8, 9, 9, 10, 11, 12, 13 days apart. When the two doses are given on the same day (0-day interval) they can be administered in two different limbs such as one dose in each arm.

Vaccination Dosing and Efficacy Criteria

In one embodiment the immunogenic compositions for use according to the present invention are a standard 0.5 ml injectable dose in most cases, and contains less than 15 μg of haemagglutinin antigen component from a pandemic influenza strain, as measured by single radial immunodiffusion (SRD) (J. M. Wood et al.: J. Biol. Stand. 5 (1977) 237-247; J. M. Wood et al., J. Biol. Stand. 9 (1981) 317-330). Suitably the vaccine dose volume will be between 0.25 and 1 ml, suitably between 0.5 ml and 1 ml, in particular a standard 0.5 ml. Slight adaptation of the dose volume will be made routinely depending on the HA concentration in the original bulk sample and depending also on the delivery route with smaller doses being given by the intranasal or intradermal route.

In one embodiment said immunogenic composition contains a classical amount of 15 μg HA per strain. In another embodiment, said immunogenic composition contains a low amount of HA antigen—e.g any of 1, 2, 3, 4, 5, 6, 7, 8, 9, 10, 11, 12, 13, 14 μg of HA per influenza strain or which does not exceed 15 μg of HA per strain. Said low amount of HA amount can be as low as practically feasible provided that it allows to formulate a vaccine which meets at least one of the international criteria, e.g. EU or FDA criteria for efficacy, as detailed below (see Table 1 and the specific parameters as set forth), but can be higher to ensure that more than one, or all of the criteria are satisfied, or to standardize production across strains. A suitable low amount of HA is between about 1 to about 7.5 μg of HA per influenza strain, suitably between about 3.5 to about 5 μg such as about 3.75 or about 3.8 μg of HA per influenza strain, typically about 5 μg of HA per influenza strain. Another suitable amount of HA is between about 0.1 and about 5 μg of HA per influenza strain, suitably between about 1.0 and about 2 μg of HA per influenza strain such as about 1.9 μg of HA per influenza strain.

Advantageously, a vaccine dose according to the invention, in particular a low HA amount vaccine, may be provided in a smaller volume than the conventional injected split flu vaccines, which are generally around about 0.5, about 0.7 or about 1 ml per dose. The low volume doses according to the invention are suitably below about 500 μl, typically below about 300 μl and suitably not more than about 200 μl or less per dose.

Thus, a suitable low volume vaccine dose according to one aspect of the invention is a dose with a low antigen dose in a low volume, e.g. about 15 µg or about 7.5 µg HA or about 3.0 µg HA (per strain) in a volume of about 200 µl.

The influenza medicament of the invention suitably meets certain international criteria for vaccines. Standards are applied internationally to measure the efficacy of influenza vaccines. Serological variables are assessed according to criteria of the European Agency for the Evaluation of Medicinal Products for human use (CHMP/BWP/214/96, Committee for Proprietary Medicinal Products (CPMP). *Note for harmonization of requirements for influenza vaccines*, 1997. CHMP/BWP/214/96 circular N° 96-0666:1-22) for clinical trials related to annual licensing procedures of influenza vaccines (Table 1A). The requirements are different for adult populations (18-60 years) and elderly populations (>60 years) (Table 1A). For interpandemic influenza vaccines, at least one of the assessments (seroconversion factor, seroconversion rate, seroprotection rate) should meet the European requirements, for all strains of influenza included in the vaccine. The proportion of titres equal or greater than 1:40 is regarded most relevant because these titres are expected to be the best currently available correlate of protection [Beyer W et al. 1998. Clin Drug Invest.; 15:1-12].

As specified in the "Guideline on dossier structure and content for pandemic influenza vaccine marketing authorisation application. (CHMP/VEG/4717/03, Apr. 5, 2004, or more recently EMEA/CHMP/VWP/263499/2006 of 24 Jan. 2007 entitled 'Guidelines on flu vaccines prepared from viruses with a potential to cause a pandemic', available on www.emea.eu.int), in the absence of specific criteria for influenza vaccines derived from non circulating strains, it is anticipated that a pandemic candidate vaccine should (at least) be able to elicit sufficient immunological responses to meet suitably all three of the current standards set for existing vaccines in unprimed adults or elderly subjects, after two doses of vaccine. The EMEA Guideline describes the situation that in case of a pandemic the population will be immunologically naive and therefore it is assumed that all three CHMP criteria for seasonal vaccines will be fulfilled by pandemic candidate vaccines. No explicit requirement to prove it in pre(pandemic)vaccination of seronegative subjects is required.

According to one embodiment of the invention, the accelerated primary immunisation of the present invention achieves, for the humoral immune response in terms of anti-haemagglutinin (anti-HA) or haemagglutination inhibition (HI) antibodies, at least one such criteria for the influenza strain included in the composition (that is the homologous strain), suitably at least two, or typically at least all three criteria for protection as set forth in Table 1A. One criteria is enough, at least for interpandemic influenza vaccines, to obtain approval.

TABLE 1A (CHMP criteria)

|  | 18-60 years | >60 years |
|---|---|---|
| Seroconversion rate* | >40% | >30% |
| Seroconversion factor** | >2.5 | >2.0 |
| Seroprotection rate*** | >70% | >60% |

*Seroconversion rate for anti-HA antibody response is defined as the proportion of subjects in each group having a protective post-vaccination titre ≥1:40. The seroconversion rate simply put is the % of subjects who have an HI titre before vaccination of <1:10 and ≥1:40 after vaccination. However, if the initial titre is ≥1:10 then there needs to be at least a fourfold increase in the amount of antibody after vaccination.
**Seroconversion factor is defined as the fold increase in serum anti-HA antibody geometric mean titres (GMTs) post vaccination for the (or each) vaccine strain.
***Seroprotection rate is defined as the proportion of subjects in each group having a protective post-vaccination titre ≥1:40; the ≥1:40 cut-off is normally accepted as indicating protection.

A 70% seroprotection rate is defined by the European health regulatory authority (CHMP—Committee for Medicinal Products for Human Use) is one of three criteria normally required to be met for an annual seasonal influenza vaccine and which CHMP is also expecting a pandemic candidate vaccine to meet.

However, mathematical modelling has indicated that a vaccine that is, at the population level, only 30% efficient against one or more heterologous strain(s) antigenically drifted may also be of benefit in helping to reduce the magnitude of a pandemic and that a pandemic vaccination campaign using a (pre-pandemic) vaccine with 30% efficacy against the pandemic strain (cross-protection of 30%) could effectively reduce the clinical attack rate by 75% and consequently morbidity/mortality within the population (Ferguson et al, Nature 2006). Accordingly, the accelerated primary immunisation of the present invention is a method for achieving early mitigation of a influenza pandemic (Ferguson, Nature 2006) or containment of an emerging influenza strain at the source (Longini, Science 2005)

FDA has published a draft guidance (CBER draft criteria) (available from the Office of Communication, Training and Manufacturers Assistance (HFM-40), 1401 Rockville Pike, Suite 200N, Rockville, Md. 20852-1448, or by calling 1-800-835-4709 or 301-827-1800, or from the Internet at http://www.fda.gov/cber/guidelines.htm) on Clinical Data Needed to Support the Licensure of Pandemic Influenza Vaccines, and the proposed criteria are also based on the CHMP criteria. FDA uses slightly different age cut-off points. Appropriate endpoints similarly include: 1) the percent of subjects achieving an HI antibody titer 1:40, and 2) rates of seroconversion, defined as a four-fold rise in HI antibody titer post-vaccination. The geometric mean titer (GMT) should be included in the results, but the data should include not only the point estimate, but also the lower bound of the 95% confidence interval of the incidence rate of seroconversion, and the day 42 incidence rate of HI titers≥1:40 must meet or exceed the target value. These data and the 95% confidence intervals (CI) of the point estimates of these evaluations should therefore be provided. FDA draft guidance requires that both targets be met. This is summarised in Table 1B.

TABLE 1B (CBER criteria)

|  | 18-64 years | >64 years |
|---|---|---|
| Seroconversion rate * | ≥40% | ≥30% |
| Rate of HI titers ≥1:40 | ≥70% | ≥60% |

* The seroconversion rate is is defined as: a) for subjects with a baseline titer ≥1:10, a 4-fold or greater rise; or b) for subjects with a baseline titer <1:10, a rise to ≥1:40.
These criteria must be met at the lower bound of the 95% CI for the true value.

Accordingly, in one aspect of the invention, it is provided for a composition, method or use as claimed herein wherein said immune response or protection induced by the administration of the contemplated pandemic composition meets all three EU regulatory criteria for influenza vaccine efficacy. Suitably at least one, suitably two, or three of following criteria are met for the influenza strain of the composition:
  a seroconversion rate of >30%, of >40%, of >50% in the seronegative population;
  a seroprotection rate of >60%, of >70%, of >80% in the seronegative population;
  a seroconversion factor of >2.0, of >2.5, of >3.0, of >4.0 in the seronegative population.

As these criteria have been set up for two doses of vaccine administered at a longer (21 days) interval, some reduction in these criteria will be allowed when the two doses are administered at a shorter (less than 14 days) interval. A reduction of 50% or of 30% efficacy may be acceptable as this will still provide a usual means to fight against the spread of the disease. Likewise, in the situation where the circulating virus is a drift-variant of the vaccine strain, the efficacy of the pre-pandemic vaccine against the circulating pandemic strain will likely be less than that of a vaccine matching the circulating strain. It is an object of the present invention to afford some level of protection quickly against the heterologous strain as reduction in the response relative to the prescribed efficacy criteria for the homologous strain will have an impact on the spread of the pandemic. Typically a reduction of 50%, or suitably a reduction of 30% in the efficacy criteria recited above will be allowed, according to this invention. Suitably in these two specific situations, i.e. cross-efficacy of the pre-pandemic vaccine against the drift-variant circulating pandemic strain, or efficacy of the accelerated primary immunisation schedule compared to the standard one, at least one, suitably two, or three of following criteria are met:

a seroconversion rate of >20% in the seronegative population;
a seroprotection rate of >40% in the seronegative population;
a seroconversion factor of >1.5 in the seronegative population.

In a specific embodiment, one or all of the criteria mentioned above are met at least 21, suitably 14 days after the second dose. It is a specific embodiment of the present invention that at least one criteria is met 7 days after the second dose.

Such an efficacy will advantageously be capable of conferring protection or cross-protection so as to lead to a substantial reduction of the overall infection attack rate, by at least 50%, or suitably at least 75%, and consequently morbidity/mortality within the population.

In still another embodiment, the two-doses primary composition is able to induce a humoral response in terms of neutralizing antibodies against a drift-variant strain, as measured by Geometric mean titres (GMT) of the neutralising antibody titres and seroconversion rates (SCR) for neutralising antibody response (defined as the percentage of vaccines without detectable antibody on Day 0 and an increase to a titer$\geq$1:28 or with a 4-fold or greater increase in neutralizing antibody titer at post vaccination). Suitably one or both of these criteria for neutralizing antibodies is (are) met in at least 30% of subjects, at least 40%, suitably at least 50%, or suitably in more than 60% of subjects against a drift-variant strain. Suitably this effect is obtained with a composition which comprises a low amount of HA such as with 7.5 μg HA or even a lower antigen dose such as 3.8 μg or 1.9 μg of HA. Suitably this effect is met at least 21, suitably 14 days after the second dose. It is a specific embodiment of the present invention that at least one criteria is met 7 days after the second dose.

Suitably any or all of such criteria are also met for other populations, such as in children and in any immuno-compromised population.

It is an object of the present invention that the above response(s) is(are) obtained after two doses administered within a short interval of up to 14 days. It is a particular advantage of the invention that the immune response is obtained after two doses of adjuvanted vaccine administered within a 0 to 7-day interval.

Accordingly, there is provided in one aspect of the invention a two-dose monovalent adjuvanted immunogenic composition comprising an influenza virus or antigenic preparation thereof, or a two-dose preparation composed of two distinct influenza virus antigens or antigenic preparations, for primary immunization of a human individual or population against influenza, in particular for promoting an immune response in a human individual or population, wherein the two primary doses are administered at a maximum of 14-day interval. In particular said influenza virus or antigenic preparation thereof is a non-live pandemic influenza virus antigen preparation, a split influenza virus preparation, in the manufacture of a vaccine composition for a two-dose accelerated primary vaccination against influenza, wherein the two-dose vaccination generates an immune response which meets at least one, suitably two or three, international regulatory requirements for influenza vaccines as recited above. In particular, said two-dose primary immunization achieves in seronegative people or population a seroconversion rate for neutralising antibody response of greater than or equal to 30%. Specifically said response is obtained against the homologous influenza strain. It is a specific embodiment that said response is obtained against one, suitable more than one such as two or three, drift-variant influenza strain(s).

In another embodiment, said two-dose primary immunization achieves at least one, at least two, or all three of the following CHMP criteria for influenza vaccines in terms of anti-haemagglutinin (anti-HA) antibodies against the vaccine influenza strain:
(i) a seroconversion rate of >30%, or >40%;
(ii) a seroprotection rate of >60% or >70%; and
(iii) a seroconversion factor of >2.0 or >2.5.

In a specific embodiment, said HI antibody response as measured against a drift-variant pandemic strain (e.g. against the pandemic strain actually causing a pandemic) or as measured compared with that obtained with the standard 2-doses at 21 days interval, meets at least one, suitably two, or three of following—lower—efficacy criteria:

a seroconversion rate of >20% in the seronegative population;
a seroprotection rate of >40% in the seronegative population;
a seroconversion factor of >1.5 in the seronegative population.

In a specific embodiment, said two-dose primary immunization achieves both a seroconversion rate for neutralising antibody response of greater than or equal to 30% against one or more drift-variant strain(s), and additionally at least one, at least two, or all three of the additional following criteria in terms of haemagglutination inhibition (HI) antibodies against the vaccine influenza strain:
(i) a seroconversion rate of greater than or equal to 30%;
(ii) a seroprotection rate of greater than or equal to 60%; and
(iii) a seroconversion factor of greater than or equal to 2.0.

In another particular embodiment said one-dose vaccination also or additionally generates a CD4 T cell immune response and/or a B cell memory response against influenza. In a specific embodiment, said influenza-specific CD4 T cell immune response is polarized toward a Th1 response. In a particular embodiment said immune response is a cross-reactive antibody response or a cross-reactive CD4 T cell response or both. In a specific embodiment the human patient is seronegative or immunologically naïve (i.e. does not have pre-existing immunity) to the vaccine strain. Specifically the vaccine composition contains a low HA antigen amount. Specifically the vaccine composition and the adjuvant are as defined herein. In particular the immunogenic properties of the vaccine composition are as defined herein. Suitably the vaccine is administered intramuscularly.

In another aspect of the present invention, there is provided the use of:
(a) an influenza virus or antigenic preparation thereof, from a first influenza strain, and
(b) an oil-in-water emulsion adjuvant as herein defined
in the manufacture of a two-dose primary immunogenic composition as herein defined, for protection against influenza infections caused by a influenza strain which is a drift variant of said first influenza strain.

Additional Properties of the Immunogenic Composition Used for the First Vaccination of the Present Invention In one embodiment, the adjuvanted composition is capable of inducing humoral antibody responses useful against circulating strains which have undergone a minor (antigenic drift) or major (antigenic shift) change in the haemagglutinin against which currently available vaccines have no efficacy.

In another embodiment, the adjuvanted composition may offer the additional or alternative benefit of promoting T cell responses useful against circulating strains which have undergone a minor (antigenic drift) or major (antigenic shift) change in the haemagglutinin against which currently available vaccines have no efficacy.

Suitably the immunogenic composition administered as claimed herein will be effective in promoting T cell responses in an immunologically unprimed patient, i.e. a patient who is seronegative to said influenza virus or antigen.

In the present invention the two-doses primary influenza immunogenic composition (whether monovalent or multivalent), administered according to the accelerated schedule will advantageously be capable of inducing a T-cell (in particular CD4 T-cell) immune response against the homologous (pandemic) vaccine strain. In a specific embodiment, said T-cell (in particular CD4 T-cell) immune response can also be obtained against a drift-variant strain such as the pandemic influenza strain causing the pandemic. In another specific embodiment, said influenza-specific response will be polarized toward a Th1 response.

Suitably said immunological response induced by an adjuvanted split influenza composition for use in the present invention is not inferior to that induced by the same composition administered according to the classical schedule of two doses given at a longer e.g. a 21-day interval.

The T-cell (in particular CD4 T-cell) immune response may be assessed by measuring the number of cells producing any of the following cytokines:
- cells producing at least two different immune markers (among CD40L, IL-2, IFNγ, TNFα)
- cells producing at least CD40L and another immune markers (among IL-2, TNFα, IFNγ)
- cells producing at least IL-2 and another immune markers (among CD40L, TNFα, IFNγ)
- cells producing at least IFNγ and another immune markers (among IL-2, TNFα, CD40L)
- cells producing at least TNFα and another immune markers (among IL-2, CD40L, IFNγ)

Typically at least one, suitably two or more of the five conditions mentioned herein above will be fulfilled.

In a specific embodiment, the administration of said immunogenic composition alternatively or additionally induces an B-memory cell response, as measured by the frequency of peripheral blood B lymphocytes capable of differentiation into antibody-secreting plasma cells upon antigen encounter as measured by stimulation of in-vitro differentiation (see Example sections, e.g. methods of Elispot B cells memory).

Suitably, the accelerated administration schedule may also be associated with a cross-responsiveness in terms of T cell responses, i.e. an ability to respond against variant influenza strains, crucial in the pandemic preparedness. This qualitatively and/or quantitatively similar response may be beneficial in all populations in the case of pandemic, and especially in a seronegative human population. This response will be of benefit for usage for priming e.g. from stockpiled vaccine containing a drift-variant, before or at onset of pandemic outbreak. This may result in reducing the overall morbidity and mortality rate and preventing emergency admissions to hospital for pneumonia and other influenza-like illness. Furthermore it may allow inducing a CD4 T cell response which is persistent in time, e.g. still present one year after the primary vaccination.

Suitably the CD4 T-cell immune response obtained in an unprimed subject involves the induction of a cross-reactive CD4 T helper response, as measured by the CD4 T-cell targeting shared epitopes between influenza strains. CD4 T-cells that are able to recognize both homologous and antigenic (drift) variant Influenza strains have been named in the present document "cross-reactive". The induction of cross-reactive CD4 T cells provides an additional advantage to the composition of the invention, in that it may provide also cross-protection, in other words protection against heterologous infections, i.e. infections caused by a circulating influenza strain which is a variant (e.g. a drift) of the influenza strain contained in the immunogenic composition. This may be advantageous when the circulating strain is difficult to propagate in eggs or to produce in cell culture, rendering the use of a drift-variant strain a working alternative. This may also be advantageous when the subject received a second vaccination several months or even a year after the two-dose primary immunisation, and the influenza strain in the immunogenic composition used for the revaccination is a drift variant strain of the strain(s) used in the composition used for the primary vaccination. This may prove to be an important advantage in a pandemic situation. For example a monovalent influenza immunogenic composition comprising any influenza strain such as H5, a H2, a H9, H7 or H6 strain(s) or a multivalent immunogenic composition composed of at least two distinct influenza virus antigens or antigenic preparations, administered according to the accelerated schedule as defined herein may provide a higher ability to respond against a pandemic variant, i.e. a drift strain of said pandemic strain(s), either upon subsequent vaccination with or upon infection by said drift strain.

Revaccination and Composition Used for Revaccination

An aspect of the present invention provides the use of an influenza antigen in the manufacture of an influenza immunogenic composition for revaccination of humans previously vaccinated with an influenza composition as claimed herein or with said influenza composition comprising an antigenic variant influenza strain, formulated with an oil-in-water emulsion adjuvant as herein defined.

Typically revaccination is made at least 1 month, suitably at least two months, suitably at least three months, or 4 months after the first primary vaccination course according to the invention, suitably 8 to 14 months after, suitably at around 10 to 12 months after or even longer. Suitably revaccination is made at least 6 months after the first vaccination(s), suitably 8 to 14 months after, suitably at around 10 to 12 months after.

The immunogenic composition for revaccination may contain any type of antigen preparation, either inactivated, recombinant or live attenuated. It may contain the same type of antigen preparation i.e. split influenza virus or split influenza virus antigenic preparation thereof, a whole virion, a sub-unit influenza virus preparation or a virosome, as the immunogenic composition used for the first vaccination. Alternatively the composition for revaccination may contain another type of influenza antigen, i.e. split influenza virus or split influenza virus antigenic preparation thereof, a whole virion, a sub-unit influenza virus preparation or a virosome, than that used for the first vaccination. Suitably a split virus or a whole virion vaccine is used.

Accordingly, in one embodiment, the invention provides for the use of an influenza virus or antigenic preparation thereof in the manufacture of an immunogenic composition for revaccination of humans previously vaccinated with a two-doses primary monovalent or multivalent immunogenic composition, or with a two-doses primary immunogenic composition composed of at least two distinct influenza virus antigens or antigenic preparations as claimed herein.

The composition for revaccination can be adjuvanted or un-adjuvanted. In one embodiment, the composition for revaccination is not adjuvanted and is a classical influenza vaccine, and can be used to revaccinate subjects having received, as a primary vaccination, an adjuvanted pandemic or seasonal influenza composition. This is advantageous as it would allow the use of commercially available unadjuvanted influenza vaccines as booster. Said vaccines for revaccination can contain three inactivated split virion antigens prepared from the WHO recommended strains of the appropriate influenza season, such as Fluvirin™, or Fluarix™/α-Rix®/Influsplit SSW® or FluLaval™/Fluviral™/GripLaval™ given intramuscularly, or such as Soluvia™ given intradermally. Alternatively, the un-adjuvanted composition for revaccination can be the live attenuated cold-adapted FluMist™ vaccine given intra-nasally.

In another embodiment the composition for revaccination is adjuvanted. Suitably the composition for revaccination comprises an oil-in-water emulsion adjuvant, in particular an oil-in-water emulsion adjuvant comprising a metabolisable oil, a sterol and/or a tocol such as tocopherol, in particular alpha tocopherol, and an emulsifying agent. Specifically, said oil-in-water emulsion adjuvant comprises at least one metabolisable oil in an amount of 0.5% to 20% of the total volume, and has oil droplets of which at least 70% by intensity have diameters of less than 1 μm. Alternatively the composition for revaccination comprises an alum adjuvant, either aluminium hydroxide or aluminium phosphate or a mixture of both. The composition for revaccination may optionally contain an additional adjuvant such as TLR-4 ligand such as 3D-MPL or a saponin, or may be another suitable adjuvant such as alum or alum alternatives such as polyphosphazene for example.

The effect of the adjuvant present in the primary immunogenic composition in enhancing the antibody response to revaccination is especially of importance in the seronegative population, such as in the elderly or infant population which is known to have a low response to vaccination or infection by influenza virus, including seasonal influenza virus. In particular, the adjuvanted composition-associated benefit will advantageously be marked in terms of improving the neutralising antibodies and in terms of CD4 T-cell response following revaccination.

The adjuvanted composition for use in the present invention will be capable of inducing a better cross-responsiveness against at least one or several drift-variant strain(s) (for example the influenza strain from the next influenza season, or the next pandemic influenza strain) compared to the protection conferred by a corresponding un-adjuvanted vaccine. Said cross-responsiveness may have the potential to show a higher persistence compared to that obtained with the un-adjuvanted formulation. The effect of the adjuvant in enhancing the cross-responsiveness against drift-variant strain is of importance in a pandemic situation.

In one embodiment, the first vaccination is made with a pandemic influenza composition as herein defined, suitably a split influenza composition, and the revaccination is made as follows.

In a specific embodiment, the immunogenic composition for revaccination contains an influenza virus or antigenic preparation thereof which shares common CD4 T-cell epitopes with the influenza virus or antigenic preparation thereof used for the first vaccination. A common CD4 T cell epitope is intended to mean peptides/sequences/epitopes from different antigens which can be recognised by the same CD4 cell (see examples of described epitopes in: Gelder C et al. 1998, Int Immunol. 10(2):211-22; Gelder C M et al. 1996 J. Virol. 70(7):4787-90; Gelder C M et al. 1995 J. Virol. 1995 69(12):7497-506).

In an embodiment according to the invention, the composition for revaccination is a monovalent influenza composition comprising an influenza strain which is a pandemic strain. Suitable strains are, but not limited to: H5N1, H9N2, H5N8, H5N9, H7N4, H7N7, H2N2, H10N7, H5N2, H5N3, H7N2, H7N1, H7N3. Said strain may be the same as that, or one of those, present in the composition used for the primary vaccination. In an alternative embodiment said strain may be a variant strain, i.e. a drift strain, of the strain present in the composition used for the first vaccination.

In a specific embodiment, the composition for revaccination is a multivalent influenza vaccine. In particular, when the composition for revaccination is a multivalent vaccine such as a bivalent, trivalent or quadrivalent vaccine, at least one strain is a pandemic strain. In a specific embodiment, two or more strains in the composition for revaccination are pandemic strains. In another specific embodiment, the at least one pandemic strain in the composition for revaccination is of the same type as that, or one of those, present in the composition used for the first vaccination. In an alternative embodiment the at least one strain may be a variant strain, i.e. a drift strain, of the at least one pandemic strain present in the composition used for the first vaccination. When the revaccination composition is a multivalent composition, at least two or all three of the criteria will ideally need to be met for all strains. However, under some circumstances two criteria may be sufficient. For example, it may be acceptable for two of the three criteria to be met by all strains while the third criterion is met by some but not all strains (e.g. two out of three strains). In a specific aspect, the primary vaccination is followed by a subsequent vaccination course of adjuvanted vaccine product containing a heterologous influenza strain.

Another suitable composition for revaccination is a trivalent seasonal composition that contains three inactivated split virion antigens prepared from the WHO recommended strains (H3N2, H1N1, B) of the appropriate influenza season, or a quadrivalent composition additionally comprising a pandemic influenza strain or a B strain from a different lineage.

The composition for revaccination may contain the same subtype of influenza antigen(s) than that used for the first vaccination. For example, when the primary vaccination is made at the declaration of a pandemic and revaccination is made later, the revaccination is made with a vaccine comprising an influenza strain (e.g. H5N1 Vietnam) which is of the same subtype as that used for the primary vaccination (e.g. H5N1 Vietnam). Alternatively the composition for revaccination may contain a drift-variant strain (such as a different clade or subclade) of the same subtype of influenza antigen(s) than that used for the primary vaccination, for example H5N1 Indonesia. In another embodiment, said influenza strain used for the revaccination is a shift strain, i.e. is different from that used for the primary vaccination, e.g. it has a different HA or NA subtype, such as H5N2 (same HA subtype as H5N1 but different NA subtype) or H7N1 (different HA subtype from H5N1 but same NA subtype). For example the vaccine composition for the primary immunisation comprises a A/Indonesian strain and the composition for revaccination comprises A/Hong Kong, A/Turkey, A/Vietnam and/or A/Anhui strain(s).

Suitably revaccination induces any, suitably two or all, of the following: (i) an improved CD4 response against the influenza virus or antigenic preparation thereof, or (ii) an improved B cell memory response or (iii) an improved humoral response, compared to the equivalent response induced after a primary vaccination with the un-adjuvanted influenza virus or antigenic preparation thereof. Suitably the immunological responses induced after revaccination with the adjuvanted influenza virus or antigenic preparation thereof as herein defined, are similar or higher than the corresponding response induced after the revaccination with the un-adjuvanted composition.

A suitable pre-pandemic vaccine strategy entails periodic (such as every 1-2 years) immunization with influenza strains with pandemic potential with the goal of maintaining and broadening responses to these viruses over time. Accordingly, in a specific embodiment, the revaccination is carried out periodically, every 1 or 2 or 3 or 4 or 5 years, with a composition comprising at least one influenza strain which is an antigenic variant of the strain used in the primary composition. Successive revaccination can be done with compositions comprising at least one influenza strain that is an antigenic variant of the strain used for the first revaccination course.

In a further embodiment the invention relates to a vaccination regime in which the primary accelerated vaccination is made with an influenza composition, suitably a split influenza composition, adjuvanted with an oil-in-water emulsion adjuvant, and containing a pandemic influenza strain and the revaccination is made with a composition, either monovalent or multivalent, comprising at least one circulating strain, either a pandemic strain causing a pandemic which may be a drift variant strain of that included in the primary composition, or a classical seasonal strain.

Optional Immunostimulants

In a specific embodiment according to the invention, the adjuvant is an oil-in-water emulsion adjuvant comprising a metabolisable oil such as squalene, a surfactant such as polysorbate 80, in the amounts defined above, and optionally a tocol such as alpha-tocopherol and does not contain any additional immunostimulants(s).

In another embodiment, the composition may comprise an additional adjuvant in particular a TLR-4 ligand adjuvant, suitably a non-toxic derivative of lipid A. A suitable TLR-4 ligand is 3 de-O-acylated monophosphoryl lipid A (3D-MPL). Other suitable TLR-4 ligands are lipopolysaccharide (LPS) and derivatives, MDP (muramyl dipeptide) and F protein of RSV.

In one embodiment the composition may additionally include a Toll like receptor (TLR) 4 ligand, such as a non-toxic derivative of lipid A, particularly monophosphoryl lipid A or more particularly 3-Deacylated monophoshoryl lipid A (3D-MPL).

3D-MPL is sold under the trademark MPL® by Corixa corporation now GSK (herein MPL) and primarily promotes CD4+ T cell responses with an IFN-γ (Th1) phenotype. It can be produced according to the methods disclosed in GB 2 220 211 A. Chemically it is a mixture of 3-deacylated monophosphoryl lipid A with 3, 4, 5 or 6 acylated chains. In particular, in the compositions of the present invention small particle 3 D-MPL is used. Small particle 3D-MPL has a particle size such that it may be sterile-filtered through a 0.22 μm filter. Such preparations are described in WO94/21292 and in Example II.

Said lipopolysaccharide, which is preferably 3D-MPL, can be used at amounts between 1 and 50 μg, per human dose of the immunogenic composition. Advantageously 3D-MPL is used at a level of around 25 μg, for example between 20-30 μg, suitably between 21-29 μg or between 22 and 28 μg or between 23 and 27 μg or between 24 and 26 μg, or 25 μg. In another embodiment, the human dose of the immunogenic composition comprises 3D-MPL at a level of around 10 μg, for example between 5 and 15 μg, suitably between 6 and 14 μg, for example between 7 and 13 μg or between 8 and 12 μg or between 9 and 11 μg, or 10 μg. In a further embodiment, the human dose of the immunogenic composition comprises 3D-MPL at a level of around 5 μg, for example between 1 and 9 μg, or between 2 and 8 μg or suitably between 3 and 7 μg or 4 and 6 μg, or 5 μg.

The dose of MPL is suitably able to enhance an immune response to an antigen in a human. In particular a suitable MPL amount is that which improves the immunological potential of the composition compared to the unadjuvanted composition, or compared to the composition adjuvanted with another MPL amount, whilst being acceptable from a reactogenicity profile.

Synthetic derivatives of lipid A are known, some being described as TLR-4 agonists, and include, but are not limited to:

OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)

OM 294 DP (3S,9R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO99/64301 and WO 00/0462)

OM 197 MP-Ac DP (3S-,9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127)

Other suitable TLR-4 ligands are, for example, lipopolysaccharide and its derivatives, muramyl dipeptide (MDP) or F protein of respiratory syncitial virus.

Other TLR4 ligands which may be used are alkyl Glucosaminide phosphates (AGPs) such as those disclosed in WO9850399 or U.S. Pat. No. 6,303,347 (processes for preparation of AGPs are also disclosed), or pharmaceutically acceptable salts of AGPs as disclosed in U.S. Pat. No. 6,764, 840. Some AGPs are TLR4 agonists, and some are TLR4 antagonists. Both are thought to be useful as adjuvants.

Other suitable TLR-4 ligands, capable of causing a signalling response through TLR-4 (Sabroe et al, JI 2003 p 1630-5) are, for example, lipopolysaccharide from gram-negative bacteria and its derivatives, or fragments thereof, in particular a non-toxic derivative of LPS (such as 3D-MPL). Other suitable TLR agonist are: heat shock protein (HSP) 10, 60, 65, 70, 75 or 90; surfactant Protein A, hyaluronan oligosaccharides, heparan sulphate fragments, fibronectin fragments, fibrinogen peptides and b-defensin-2, muramyl dipeptide (MDP) or F protein of respiratory syncitial virus. In one embodiment the TLR agonist is HSP 60, 70 or 90.

Toll-like receptors (TLRs) are type I transmembrane receptors, evolutionarily conserved between insects and humans. Ten TLRs have so far been established (TLRs 1-10) (Sabroe et al, JI 2003 p 1630-5). Members of the TLR family have similar extracellular and intracellular domains; their extracellular domains have been shown to have leucine—rich repeating sequences, and their intracellular domains are similar to the intracellular region of the interleukin-1 receptor (IL-1R). TLR cells are expressed differentially among immune cells and other cells (including vascular epithelial cells, adipocytes, cardiac myocytes and intestinal epithelial cells). The intracellular domain of the TLRs can interact with the adaptor protein Myd88, which also posses the IL-1R domain in its cytoplasmic region, leading to NF-KB activation of cytokines; this Myd88 pathway is one way by which cytokine release is effected by TLR activation. The main expression of TLRs is in cell types such as antigen presenting cells (eg dendritic cells, macrophages etc).

Activation of dendritic cells by stimulation through the TLRs leads to maturation of dendritic cells, and production of inflammatory cytokines such as IL-12. Research carried out so far has found that TLRs recognise different types of agonists, although some agonists are common to several TLRs. TLR agonists are predominantly derived from bacteria or viruses, and include molecules such as flagellin or bacterial lipopolysaccharide (LPS).

By "TLR agonist" it is meant a component which is capable of causing a signalling response through a TLR signalling pathway, either as a direct ligand or indirectly through generation of endogenous or exogenous ligand (Sabroe et al, JI 2003 p 1630-5).

In another embodiment, other natural or synthetic agonists of TLR molecules are used as optional additional immunostimulants. These could include, but are not limited to agonists for TLR2, TLR3, TLR7, TLR8 and TLR9.

In one embodiment of the present invention, a TLR agonist is used that is capable of causing a signalling response through TLR-1 (Sabroe et al, JI 2003 p 1630-5). Suitably, the TLR agonist capable of causing a signalling response through TLR-1 is selected from: Tri-acylated lipopeptides (LPs); phenol-soluble modulin; *Mycobacterium tuberculosis* LP; S-(2,3-bis(palmitoyloxy)-(2-RS)-propyl)-N-palmitoyl-(R)-Cys-(S)-Ser-(S)-Lys(4)-OH, trihydrochloride (Pam₃Cys) LP which mimics the acetylated amino terminus of a bacterial lipoprotein and OspA LP from *Borrelia burgdorfei*.

In an alternative embodiment, a TLR agonist is used that is capable of causing a signalling response through TLR-2 (Sabroe et al, JI 2003 p 1630-5). Suitably, the TLR agonist capable of causing a signalling response through TLR-2 is one or more of a lipoprotein, a peptidoglycan, a bacterial lipopeptide from *M. tuberculosis, B. burgdorferi. T pallidum*; peptidoglycans from species including *Staphylococcus aureus*; lipoteichoic acids, mannuronic acids, *Neisseria* porins, bacterial fimbriae, Yersina virulence factors, CMV virions, measles haemagglutinin, and zymosan from yeast.

In an alternative embodiment, a TLR agonist is used that is capable of causing a signalling response through TLR-3 (Sabroe et al, JI 2003 p 1630-5). Suitably, the TLR agonist capable of causing a signalling response through TLR-3 is double stranded RNA (dsRNA), or polyinosinic-polycytidylic acid (Poly IC), a molecular nucleic acid pattern associated with viral infection.

In an alternative embodiment, a TLR agonist is used that is capable of causing a signalling response through TLR-5 (Sabroe et al, JI 2003 p 1630-5). Suitably, the TLR agonist capable of causing a signalling response through TLR-5 is bacterial flagellin.

In an alternative embodiment, a TLR agonist is used that is capable of causing a signalling response through TLR-6 (Sabroe et al, JI 2003 p 1630-5). Suitably, the TLR agonist capable of causing a signalling response through TLR-6 is mycobacterial lipoprotein, di-acylated LP, and phenol-soluble modulin. Further TLR6 agonists are described in WO2003043572.

In an alternative embodiment, a TLR agonist is used that is capable of causing a signalling response through TLR-7 (Sabroe et al, JI 2003 p 1630-5). Suitably, the TLR agonist capable of causing a signalling response through TLR-7 is a single stranded RNA (ssRNA), loxoribine, a guanosine analogue at positions N7 and C8, or an imidazoquinoline compound, or derivative thereof. In one embodiment, the TLR agonist is imiquimod. Further TLR7 agonists are described in WO02085905.

In an alternative embodiment, a TLR agonist is used that is capable of causing a signalling response through TLR-8 (Sabroe et al, JI 2003 p 1630-5). Suitably, the TLR agonist capable of causing a signalling response through TLR-8 is a single stranded RNA (ssRNA), an imidazoquinoline molecule with anti-viral activity, for example resiquimod (R848); resiquimod is also capable of recognition by TLR-7. Other TLR-8 agonists which may be used include those described in WO2004071459.

In an alternative embodiment, a TLR agonist is used that is capable of causing a signalling response through TLR-9 (Sabroe et al, JI 2003 p 1630-5). In one embodiment, the TLR agonist capable of causing a signalling response through TLR-9 is HSP90. Alternatively, the TLR agonist capable of causing a signalling response through TLR-9 is bacterial or viral DNA, DNA containing unmethylated CpG nucleotides, in particular sequence contexts known as CpG motifs. CpG-containing oligonucleotides induce a predominantly Th1 response. Such oligonucleotides are well known and are described, for example, in WO 96/02555, WO 99/33488 and U.S. Pat. Nos. 6,008,200 and 5,856,462. Suitably, CpG nucleotides are CpG oligonucleotides. Suitable oligonucleotides for use in the immunogenic compositions of the present invention are CpG containing oligonucleotides, optionally containing two or more dinucleotide CpG motifs separated by at least three, suitably at least six or more nucleotides. A CpG motif is a Cytosine nucleotide followed by a Guanine nucleotide. The CpG oligonucleotides of the present invention are typically deoxynucleotides. In a specific embodiment the internucleotide in the oligonucleotide is phosphorodithioate, or suitably a phosphorothioate bond, although phosphodiester and other internucleotide bonds are within the scope of the invention. Also included within the scope of the invention are oligonucleotides with mixed internucleotide linkages. Methods for producing phosphorothioate oligonucleotides or phosphorodithioate are described in U.S. Pat. No. 5,666,153, U.S. Pat. No. 5,278,302 and WO95/26204. Examples of preferred oligonucleotides have the following sequences. The sequences preferably contain phosphorothioate modified internucleotide linkages:

```
OLIGO 1 (SEQ ID NO: 1):
TCC ATG ACG TTC CTG ACG TT (CpG 1826)

OLIGO 2 (SEQ ID NO: 2):
TCT CCC AGC GTG CGC CAT (CpG 1758)

OLIGO 3 (SEQ ID NO: 3):
ACC GAT GAC GTC GCC GGT GAC GGC ACC ACG

OLIGO 4 (SEQ ID NO: 4):
TCG TCG TTT TGT CGT TTT GTC GTT (CpG 2006)

OLIGO 5 (SEQ ID NO: 5):
TCC ATG ACG TTC CTG ATG CT (CpG 1668)

OLIGO 6 (SEQ ID NO: 6):
TCG ACG TTT TCG GCG CGC GCC G (CpG 5456)
```

Alternative CpG oligonucleotides may comprise the specified sequences above in that they have inconsequential deletions or additions thereto. The CpG oligonucleotides utilised in the present invention may be synthesized by any method known in the art (for example see EP 468520). Conveniently, such oligonucleotides may be synthesized utilising an automated synthesizer.

Accordingly, in another embodiment, the adjuvant and immunogenic composition further comprises an additional immunostimulant which is selected from the group consisting of: a TLR-1 agonist, a TLR-2 agonist, TLR-3 agonist, a TLR-4 agonist, TLR-5 agonist, a TLR-6 agonist, TLR-7 agonist, a TLR-8 agonist, TLR-9 agonist, or a combination thereof.

In another embodiment, the adjuvant and immunogenic composition further comprises a saponin adjuvant. A particularly suitable saponin for use in the present invention is Quil A and its derivatives. Quil A is a saponin preparation isolated from the South American tree *Quillaja Saponaria* Molina and was first described by Dalsgaard et al. in 1974 ("Saponin adjuvants", Archiv. für die gesamte Virusforschung, Vol. 44, Springer Verlag, Berlin, p 243-254) to have adjuvant activity. Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of *Quillaja saponaria* Molina, which induces CD8+ cytotoxic T cells (CTLs), Th1 cells and a predominant IgG2a antibody response and is a preferred saponin in the context of the present invention. In a suitable form of the present invention, the saponin adjuvant within the immunogenic composition is a derivative of *saponaria molina* quil A, preferably an immunologically active fraction of Quil A, such as QS-17 or QS-21, suitably QS-21. In one embodiment the compositions of the invention contain the immunologically active saponin fraction in substantially pure form. Preferably the compositions of the invention contain QS21 in substantially pure form, that is to say, the QS21 is at least 90% pure, for example at least 95% pure, or at least 98% pure.

Other useful saponins are derived from the plants *Aesculus hippocastanum* or *Gyophilla struthium*. Other saponins which have been described in the literature include Escin, which has been described in the Merck index (12$^{th}$ ed: entry 3737) as a mixture of saponins occurring in the seed of the horse chestnut tree, Lat: *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190). Fractions of escin have been purified and shown to be biologically active (Yoshikawa M, et al. (Chem Pharm Bull (Tokyo) 1996 August; 44(8):1454-1464)). Sapoalbin from *Gypsophilla struthium* (R. Vochten et al., 1968, J. Pharm. Belg., 42, 213-226) are also an option.

Said immunologically active saponin, which is preferably QS21, can be used amounts 1 and 50 µg, per human dose of the immunogenic composition. Advantageously QS21 is used at a level of around 25 µg, for example between 20-30 µg, suitably between 21-29 µg or between 22 and 28 µg or between 23 and 27 µg or between 24 and 26 µg, or 25 µg. In another embodiment, the human dose of the immunogenic composition comprises QS21 at a level of around 10 µg, for example between 5 and 15 µg, suitably between 6 and 14 µg, for example between 7 and 13 µg or between 8 and 12 µg or between 9 and 11 µg, or 10 µg. In a further embodiment, the human dose of the immunogenic composition comprises QS21 at a level of around 5 µg, for example between 1 and 9 µg, or between 2 and 8 µg or suitably between 3 and 7 µg or 4 and 6 µg, or 5 µg.

The dose of 3D-MPL and/or QS21 is suitably able to enhance an immune response to an antigen in a human. In particular a suitable 3D-MPL and/or QS21 amount is that which improves the immunological potential of the composition compared to the unadjuvanted composition, or compared to the composition adjuvanted with another 3D-MPL or QS21 amount, whilst being acceptable from a reactogenicity profile. Typically for human administration the saponin (e.g. QS21) and/or LPS derivative (e.g. 3D-MPL) will be present in a human dose of immunogenic composition in the range of 1 µg-200 µg, such as 10-50 µg, or 1 µg-25 µg per dose.

In a specific embodiment, the adjuvant and immunogenic compositions according to the invention comprise a saponin (e.g. QS21) and/or an LPS derivative (e.g. 3D-MPL) in an oil emulsion described above, together with a sterol (e.g. cholesterol). These sterols are well known in the art, for example cholesterol is disclosed in the Merck Index, 11th Edn., page 341, as a naturally occurring sterol found in animal fat. Additionally the oil emulsion (in particular the oil-in-water emulsion) may contain Span 85 and/or lecithin and/or tricaprylin. Adjuvants comprising an oil-in-water emulsion, a sterol and a saponin are described in WO 99/12565. Examples of further immunostimulants are described herein and in "Vaccine Design—The Subunit and Adjuvant Approach" 1995, Pharmaceutical Biotechnology, Volume 6, Eds. Powell, M. F., and Newman, M. J., Plenum Press, New York and London, ISBN 0-306-44867-X.

Where squalene and a saponin (optionally QS21) are included, it is of benefit to also include a sterol (optionally cholesterol) to the formulation as this allows a reduction in the total level of oil in the emulsion. This leads to a reduced cost of manufacture, improvement of the overall comfort of the vaccination, and also qualitative and quantitative improvements of the resultant immune responses, such as improved IFN-γ production. Optionally a sterol (e.g. cholesterol) is also included.

Adjuvants wherein an additional immunostimulant is optionally included are particularly suitable for infant and/or elderly vaccine formulations.

Vaccination Means

The composition of the invention may be administered by any suitable delivery route, such as intradermal, mucosal e.g. intranasal, oral, intramuscular or subcutaneous. Other delivery routes are well known in the art.

The intramuscular delivery route is particularly suitable for an adjuvanted influenza composition. The composition according to the invention may be presented in a monodose container, or alternatively, a multidose container, particularly suitable for a pandemic vaccine. In this instance an antimicrobial preservative such a thiomersal is typically present to prevent contamination during use. Thiomersal concentration may be at 25 µg/0.5 ml dose (i.e. 50 µg/mL). A thiomersal concentration of 5 µg/0.5 ml dose (i.e. 10 µg/ml) or 10 µg/0.5 ml dose (i.e. 20 µg/ml) is suitably present. A suitable IM delivery device could be used such as a needle-free liquid jet injection device, for example the Biojector 2000 (Bioject, Portland, Oreg.). Alternatively a pen-injector device, such as is used for at-home delivery of epinephrine, could be used to allow self administration of vaccine. The use of such delivery devices may be particularly amenable to large scale immunization campaigns such as would be required during a pandemic.

Intradermal delivery is another suitable route. Any suitable device may be used for intradermal delivery, for example needle-free or short needle devices such as devices which limit the effective penetration length of a needle into the skin, such as those described in WO99/34850 and EP1092444, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Also suitable are ballistic powder/ particle delivery devices which use compressed gas to accelerate vaccine in powder form through the outer layers of the skin to the dermis. Additionally, conventional syringes may be used in the classical mantoux method of intradermal administration.

Another suitable administration route is the subcutaneous route. Any suitable device may be used for subcutaneous delivery, for example a classical needle or a needle-free jet injector service. Suitably said device is pre-filled with the liquid vaccine formulation.

Alternatively the vaccine is administered intranasally. Typically, the vaccine is administered locally to the nasopharyngeal area, suitably without being inhaled into the lungs. It is desirable to use an intranasal delivery device which delivers the vaccine formulation to the nasopharyngeal area, without or substantially without it entering the lungs.

Suitable devices for intranasal administration of the vaccines according to the invention are spray devices. They are known in the art.

Alternatively, the epidermal or transdermal vaccination route is also contemplated in the present invention.

In one aspect of the present invention, the two-dose primary adjuvanted immunogenic composition for the first administration may be given intramuscularly, and the revaccination composition, either adjuvanted or not, may be administered through a different route, for example intradermal, subcutaneous or intranasal. In a specific embodiment, the composition for the first administration contains a HA amount of less than 15 μg for the pandemic influenza strain, and the boosting composition may contain a standard amount of 15 μg or, suitably a low amount of HA, i.e. below 15 μg, which, depending on the administration route, may be given in a smaller volume.

Populations to Vaccinate

The target population to vaccinate is the entire population, e.g. healthy young adults (e.g. aged 18-60), elderly (typically aged above 60) or infants/children. The target population may in particular be seronegative or immuno-compromised. Immuno-compromised humans generally are less well able to respond to an antigen, in particular to an influenza antigen, in comparison to healthy adults.

In one aspect according to the invention, the target population is a population which is unprimed against influenza, either being naïve (such as vis à vis a pandemic strain), or having failed to respond previously to influenza seasonal infection or vaccination. Suitably the target population is elderly persons suitably aged at least 60, or 65 years and over, younger high-risk adults (i.e. between 18 and 60 years of age) such as people working in health institutions, or those young adults with a risk factor such as cardiovascular and pulmonary disease, or diabetes. Another target population is all children 6 months of age and over, especially children 6-23 months of age who experience a relatively high influenza-related hospitalization rate. Another target population is younger children from birth to 6 months of age. Another target population is children less than 2 years or less than 9 years of age.

The teaching of all references in the present application, including patent applications and granted patents, are herein fully incorporated by reference. Any patent application to which this application claims priority is incorporated by reference herein in its entirety in the manner described herein for publications and references.

The invention will be further described by reference to the following, non-limiting, examples:

Example I describes immunological read-out methods used in mice, ferrets, pigs and human studies.

Example II describes the preparation of the oil in water emulsion adjuvant formulations used in the studies exemplified.

Example III shows a clinical trial setting in an adult population aged 18-60 years immunised according to an accelerated schedule with a primary composition for two doses administration, containing a split influenza antigen preparation and an oil-in-water emulsion adjuvant Example IV shows a clinical study in adults over 60 years of age immunized with a single or double-dose of the pandemic influenza candidate vaccine (split virus formulation adjuvanted with AS03) given following a two-administration schedule (21 days apart)

Example V shows a preclinical evaluation setting of an accelerated priming of naïve C57Bl/6 mice with an adjuvanted split H5N1 vaccines

Example I

Immunological Read-Out Methods

I.1. Assays for Assessing the Immune Response in Humans

I.1.1. Hemagglutination Inhibition Assay

The immune response was determined by measuring HI antibodies using the method described by the WHO Collaborating Centre for influenza, Centres for Disease Control, Atlanta, USA (1991).

Antibody titre measurements were conducted on thawed frozen serum samples with a standardised and comprehensively validated micromethod using 4 hemagglutination-inhibiting units (4 HIU) of the appropriate antigens and a 0.5% fowl (or 0.5% horse for H5N1) erythrocyte suspension. Non-specific serum inhibitors were removed by heat treatment and receptor-destroying enzyme.

The sera obtained were evaluated for HI antibody levels. Starting with an initial dilution of 1:10, a dilution series (by a factor of 2) was prepared up to an end dilution of 1:20480. The titration end-point was taken as the highest dilution step that showed complete inhibition (100%) of hemagglutination. All assays were performed in duplicate.

Adaptation for H5N1

Specific description of HI using Horse erythrocytes:

Glycoproteins (haemaglutinins) are located in the viral envelope, and are able to agglutinate erythrocytes (red blood cells) of many species e.g. chicken.

The haemagglutination inhibition test is carried out in two steps:

1. Antigen-antibody reaction: the Influenza antigen (DTA, dialysis test antigen) reacts with the antibodies of the subject's serum.
2. Agglutination of excessive antigen: excessive antigen reacts with added red blood cells Erythrocytes of horses are used for the H5N1 Pandemic strains.

0.5% (end concentration) horse red blood cell suspension in phosphate buffer containing 0.5% BSA (bovine serum albumin, end concentration).

This suspension is prepared every day by washing red blood cell with the same phosphate buffer and a subsequent centrifugation step (10 min, 600×g). This washing step has to be repeated once.

After the addition of the horse red blood cells to the reaction mix of patient/subject sera and virus suspension the plates are incubated at room temperature (RT, 20° C.+/−2° C.) for two hours due to the low sedimentation rate of the horse red blood cells.

I.1.2. Neuraminidase Inhibition Assay The neuraminidase Inhibition assay was performed in fetuin-coated microtitre plates. A 2-fold dilution series of the antiserum was prepared and mixed with a standardised amount of influenza A H3N2, H1N1 or influenza B virus. The test was based on the biological activity of the neuraminidase which enzymatically releases neuraminic acid from fetuin. After cleavage of the terminal neuraminic acid β-D-glactose-N-acetyl-galactosamin was unmasked. Horseradish peroxidase (HRP)-labelled peanut agglutinin from *Arachis hypogaea*, which binds specifically to the galactose structures, was added to the wells. The amount of bound agglutinin can be detected and quantified in a substrate reaction with tetra-methylbenzidine (TMB) The highest antibody dilution that still inhibits the viral neuraminidase activity by at least 50% was indicated is the NI titre. Alternative protocols can also be used according to the present invention.

I.1.3. Neutralising Antibody Assay

Neutralising antibody measurements are conducted on thawed frozen serum samples. Virus neutralisation by antibodies contained in the serum is determined in a microneutralization assay. The sera are used without further treatment in the assay. Each serum is tested in triplicate. A standardised amount of virus is mixed with serial dilutions of serum and incubated to allow binding of the antibodies to the virus. A cell suspension, containing a defined amount of MDCK cells is then added to the mixture of virus and antiserum and incubated at 33° C. After the incubation period, virus replication is visualised by hemagglutination of chicken red blood cells. The 50% neutralisation titre of a serum is calculated by the method of Reed and Muench (Am. J; Hyg. 1938, 27: 493-497).

I.1.4. Cell-Mediated Immunity was Evaluated by Cytokine Flow Cytometry (CFC)

Peripheral blood antigen-specific CD4 and CD8 T cells can be restimulated in vitro to produce IL-2, CD40L, TNF-alpha and IFN if incubated with their corresponding antigen. Consequently, antigen-specific CD4 and CD8 T cells can be enumerated by flow cytometry following conventional immunofluorescence labelling of cellular phenotype as well as intracellular cytokines production. In the present study, Influenza vaccine antigen are used as antigen to restimulate Influenza-specific T cells. Results are expressed as a frequency of influenza-specific CD4 or CD8 T cell that produce one or several immune markers within the CD4 or CD8 T cell subpopulation.

I.1.5. Memory B Cells by ELISPOT

The ELISPOT technology allows the quantification of memory B cells specific to a given antigen. Memory B-cells can be induced to differentiate into plasma cells in vitro following cultivation with CpG for 5 days. In vitro generated antigen-specific plasma cells can therefore be enumerated using the ELISPOT assay. Briefly, in vitro generated plasma cells are incubated in culture plates coated with antigen. Antigen-specific plasma cells form antibody/antigen spots, which can be detected by conventional immuno-enzymatic procedure. In the present study, influenza vaccine strains or anti-human Immunoglobulins are used to coat culture plates in order to enumerate influenza-specific antibody or IgG secreting plasma cells, respectively. Results are expressed as a frequency of influenza-specific antibody secreting plasma cells within the IgG-producing plasma cells.

I.1.6. Statistical Methods

I.1.6.1. Immunogenicity Endpoints

Vaccine-homologous and drift variant seasonal or pandemic influenza antibody responses, as measured by haemagglutination inhibition (HI)
    Observed variables: influenza HI titers
    Derived variables (see Table 1A for definitions):
        Geometric mean titers (GMTs) of seasonal or pandemic influenza HI antibodies
        Seropositivity rates of seasonal or pandemic influenza HI antibodies
        Seroconversion rates (SCR)
        Seroconversion factors (SCF)
        Seroprotection rates (SPR)

Vaccine-homologous and drift variant H5N1 antibody responses, as measured by neutralising antibodies (NAb) titers
    Observed variables: seasonal or pandemic influenza NAb titers
    Derived variables:
        Geometric mean titers (GMTs) of seasonal or pandemic influenza NAb antibodies
        Seropositivity rates of seasonal or pandemic influenza NAb antibodies
        Seroconversion rates (SCR; defined as the percentage of vaccines with at least a four-fold increase in post-vaccination titer)

Vaccine-homologous and drift variant seasonal or pandemic influenza responses in terms of cell-mediated immunity (CMI)
    Frequency of influenza-specific CD4/CD8 T-cells per $10^6$ producing Th1-specific activation markers (CD40L, IL-2, TNF-α, IFN-γ).
    Frequency of influenza-specific CD4/CD8 T-cells per $10^6$ producing Th2-specific activation markers (IL-4, IL-5, IL-13, CRTH2).
    Frequency of influenza-specific memory B-cells per $10^6$ cells.

Vaccine-homologous and drift variant seasonal or pandemic influenza antibody responses, as measured by neuraminidase inhibition (NI)
    Observed variables: influenza NI titers
    Derived variables:
        Geometric mean titers (GMTs) of seasonal or pandemic influenza NI antibodies I.1.6.2. Safety Endpoints Percentage, intensity and relationship to vaccination of solicited local and general signs and symptoms during a 7 day follow-up period (i.e. day of vaccination and 6 subsequent days) after each vaccination and overall.

Percentage, intensity and relationship to vaccination of unsolicited local and general signs and symptoms during a follow-up period corresponding to 51 days after the first vaccination and overall.

Occurrence of serious adverse events during the entire study.

Number and percentage of subjects with normal or abnormal values for biochemical assessments and for hematological analyses.

I.2. Mice Methods
I.2.1. Anti-H5N1 ELISA.

Quantitation of anti-H5N1 IgG antibody was performed by ELISA using Split H5N1 as coating. Virus and antibody solutions were used at 100 μl per well. Split virus H5N1 was diluted at a final concentration of 1 μg/ml in PBS and was adsorbed overnight at 4° C. to the wells of 96 wells microtiter plates (Maxisorb Immunoplate Nunc 439454). The plates were then incubated for 1 hour at 37° C. with 200 μl per well of PBS containing 1% BSA and 0.1% Tween 20 (saturation buffer). Twelve two-fold dilutions of sera in saturation buffer were added to the H5N1-coated plates and incubated for 1 h30 at 37° C. The plates were washed four times with PBS 0.1% Tween 20. Peroxidase-conjugated anti-mouse IgG (Sigma A5278) diluted 1/1000 in PBS 1% BSA 0.1% Tween 20 was added to each well and incubated for 1 hour at 37° C. After a washing step, plates were incubated 20 min at 22° C. with a solution of o-phenyldiamine (Sigma P4664) 0.04% $H_2O_2$ 0.03% in 0.1 M citrate buffer pH 4.2. The reaction was stopped with $H_2SO_4$ 2N and micoplates were read at 490-630 nm.

I.2.2. Hemagglutination Inhibition (HI) Assay.

The protocol used is adapted from the classical HI assay for determining anti-HA antibodies, and relied on the use of horse RBC.

Test Principle (Classical Procedure)

Anti-Hemagglutinin antibody titers to the three (seasonal) influenza virus strains are determined using the hemagglutination inhibition test (HI). The principle of the HI test is based on the ability of specific anti-Influenza antibodies to inhibit hemagglutination of red blood cells (RBC) by influenza virus hemagglutinin (HA). Heat inactivated sera are treated by Kaolin and RBC to remove non-specific inhibitors. After pretreatment, two-fold dilutions of sera are incubated with 4 hemagglutination units of each influenza strain. Red blood cells are then added and the inhibition of agglutination is scored. The titers are expressed as the reciprocal of the highest dilution of serum that completely inhibited hemagglutination. As the first dilution of sera is 1:20, an undetectable level is scored as a titer equal to 10.

Adaptation for H5N1 (Specific Description of HI Using Horse Erythrocytes)

Erythrocytes of horses are used for the H5N1 Pandemic strains. 0.5% (end concentration) horse red blood cell suspension in phosphate buffer containing 0.5% BSA (bovine serum albumin, end concentration). This suspension is prepared every day by washing red blood cell with the same phosphate buffer and a subsequent centrifugation step (10 min, 2000 rpm). This washing step is repeated once. After the addition of the horse red blood cells to the reaction mix of sera and virus suspension; the plates are incubated at room temperature (RT, 20° C.+/−2° C.) for two hours due to the low sedimentation rate of the horse red blood cells.

Statistical Analysis

Statistical analysis are performed on post vaccination HI titers using UNISTAT. The protocol applied for analysis of variance can be briefly described as follow:

Log transformation of data

Shapiro-Wilk test on each population (group) in order to verify the normality of groups distribution Cochran test in order to verify the homogenicity of variance between the different populations (groups)

Analysis of variance on selected data.

Test for interaction of two-way ANOVA

Tukey-HSD Test for multiple comparisons

I.2.3. Neutralizing Antibody Assay

Neutralizing antibody measurements are conducted on thawed frozen serum samples. Virus neutralization by antibodies contained in the serum is determined in a microneutralization assay. The sera are used without further treatment in the assay. Each serum is tested in triplicate. A standardised amount of virus is mixed with serial dilutions of serum and incubated to allow binding of the antibodies to the virus. A cell suspension, containing a defined amount of MDCK cells is then added to the mixture of virus and antiserum and incubated at 33° C. After the incubation period, virus replication is visualised by hemagglutination of chicken red blood cells. The 50% neutralization titre of a serum is calculated by the method of Reed and Muench (Am. J; Hyg. 1938, 27: 493-497).

I.2.4. Intracellular Cytokine Staining (ICS).

This technique allows a quantification of antigen specific T lymphocytes on the basis of cytokine production: effector T cells and/or effector-memory T cells produce IFN-γ and/or central memory T cells produce IL-2.

Intracellular staining of cytokines of T cells is performed on PBMC 7 days after the immunization. Blood is collected from mice and pooled in heparinized medium RPMI+Add*. For blood, RPMI+Add-diluted PBL suspensions are layered onto a Lympholyte—Mammal gradient according to the recommended protocol (centrifuge 20 minutes at 2500 rpm and R.T.). The mononuclear cells at the interface are removed, washed 2-fold in RPMI+Add and PBMCs suspensions are adjusted to $10^7$ cells/ml in RPMI 5% fetal calf serum.

composition of RMPI+Add

RPMI 1640 without L-glutamine (Gibco 31870-025/041-01870M)

+Additives (for 500 ml RPMI): 5 ml sodium pyruvate 100 mM (Gibco lot 11360-039), 5 ml MEM non essential amino acids ((Gibco lot 11140-035), 5 ml Pen/Strep (Gibco lot 20F9252), 5 ml glutamine (Gibco lot 24Q0803), 500 μl 2-mercaptoethanol 1000× (Gibco ref. 31350-010).

In vitro antigen stimulation of PBMCs is carried out at a final concentration of $10^6$ cells/wells (microplate) with Formalin-inactivated split 1 μg HA/strain and then incubated 2 hours at 37° C. with the addition of anti-CD28 and anti-CD49d (1 μg/ml for the both). The addition of both antibodies increased proliferation and cytokine production by activated T and NK cells and can provide a costimulatory signal for CTL induction.

Following the antigen restimulation step, PBMC are incubated O.N. at 37° C. in presence of Brefeldin (1 μg/ml) at 37° C. to inhibit cytokine secretion. IFN-γ/IL-2/CD4/CD8 staining is performed as follows: cell suspensions were washed, resuspended in 50 μl of PBS 1% FCS containing 2% Fc blocking reagent (1/50; 2.4G2). After 10 minutes incubation at 4° C., 50 μl of a mixture of anti-CD4-PE (2/50) and anti-CD8 perCp (3/50) is added and incubated 30 minutes at 4° C.

After a washing in PBS 1% FCS, cells are permeabilized by resuspending in 200 μl of Cytofix-Cytoperm (Kit BD) and incubated 20 minutes at 4° C. Cells are then washed with Perm Wash (Kit BD) and resuspended with 50 μl of a mix of anti-IFN-γ APC (1/50)+anti-IL-2 FITC (1/50) diluted in Perm Wash. After incubation (minimum 2 hours and maximum overnight) at 4° C., cells are washed with Perm Wash and resuspended in PBS 1% FCS+1% paraformaldehyde. Sample analysis is performed by FACS. Live cells were gated (FSC/SSC) and acquisition is performed on ~50,000 events (lymphocytes) or 15,000 events on CD4+ T cells. The percentages of IFN-γ+ or IL2+ are calculated on CD4+ and CD8+ gated populations.

Example II

Preparation of the Oil in Water Emulsion and Adjuvant Formulations

Unless otherwise stated, the oil/water emulsion used in the subsequent examples is composed an organic phase made of 2 oils (alpha-tocopherol and squalene), and an aqueous phase of PBS containing Tween 80 as emulsifying agent. Unless otherwise stated, the oil in water emulsion adjuvant formulations used in the subsequent examples were made comprising the following oil in water emulsion component (final concentrations given): 2.5% squalene (v/v), 2.5% alpha-tocopherol (v/v), 0.9% polyoxyethylene sorbitan monooleate (v/v) (Tween 80), see WO 95/17210. This emulsion, termed AS03 in the subsequent examples, was prepared as followed as a two-fold concentrate.

II.1. Preparation of Emulsion SB62

This method was used in the studies reported in the clinical and pre-clinical examples sections. The preparation of the SB62 emulsion is made by mixing under strong agitation of an oil phase composed of hydrophobic components (DL-α-tocopherol and squalene) and an aqueous phase containing the water soluble components (the anionic detergent Tween 80 and PBS mod (modified), pH 6.8). While stirring, the oil phase (1/10 total volume) is transferred to the aqueous phase (9/10 total volume), and the mixture is stirred for 15 minutes at room temperature. The resulting mixture then subjected to shear, impact and cavitation forces in the interaction chamber of a microfluidizer (15000 PSI-8 cycles, or 3 cycles in the adjuvant used in the clinical trial reported in Example III) to produce submicron droplets (distribution between 100 and 200 nm). The resulting pH is between 6.8±0.1. The SB62 emulsion is then sterilised by filtration through a 0.22 μm membrane and the sterile bulk emulsion is stored refrigerated in Cupac containers at 2 to 8° C. Sterile inert gas (nitrogen or argon) is flushed into the dead volume of the SB62 emulsion final bulk container for at least 15 seconds.

The final composition of the SB62 emulsion is as follows: Tween 80:1.8% (v/v) 19.4 mg/ml; Squalene: 5% (v/v) 42.8 mg/ml; α-tocopherol: 5% (v/v) 47.5 mg/ml; PBS-mod: NaCl 121 mM, KCl 2.38 mM, Na2HPO4 7.14 mM, KH2PO4 1.3 mM; pH 6.8±0.1.

Example III

Clinical Trial in an Adult Population Aged 18-60 Years with a Monovalent Influenza Vaccine Containing a H5N1 Split Influenza Antigen Preparation and AS03 Adjuvant Administered According to an Accelerated Two-Dose Primary Immunisation Schedule III.1. Study Design
III.1.1. Subject: Phase IIb, open-label, randomized study enrolling 312 adults (in order to reach at least 280 evaluable subjects) aged 18-60 years to assess the immunogenicity of accelerated primary vaccination with a pandemic (H5N1) monovalent adjuvanted influenza vaccine.
III.1.2. Design
Four groups of subjects each primed/administered with two primary doses of influenza vaccine comprising a low amount of A/Indonesia/5/2005 (H5N1) strain and adjuvanted with AS03 at either 21 (Group 1), 14 (Group 2), 7 (Group 3) or 0 (Group 4) day intervals.
Treatment Groups (Table 2)
Group 1: two 3.8 μg doses of the vaccine formulated with the A/Indonesia/5/2005 strain adjuvanted with AS03 and administered at a 21-day interval.
Group 2: two 3.8 μg doses of the vaccine formulated with the A/Indonesia/5/2005 strain adjuvanted with AS03 and administered at a 14-day interval.
Group 3: two 3.8 μg doses of the vaccine formulated with the A/Indonesia/5/2005 strain adjuvanted with AS03 and administered at a 7-day interval.
Group 4: two 3.8 μg doses of the vaccine formulated with the A/Indonesia/5/2005 strain adjuvanted with AS03 and administered the same day (one 3.8 μg dose/arm).
Vaccination Schedule(s): Summarised in Table 2

TABLE 2

| Timepoint | Formulation | Groups |
| --- | --- | --- |
| Day 0 priming administration | Split virus A/Indonesia/5/2005 (3.8 μg) + AS03 (1 dose at Day 0) | Groups 1, 2 and 3 |
| Day 0 priming administration | Split virus A/Indonesia/5/2005 (3.8 μg) + AS03 (2 doses at Day 0 - one dose per arm) | Group 4 |
| Day 7 priming administration | Split virus A/Indonesia/5/2005 (3.8 μg) + AS03 (1 dose at Day 7) | Group 3 |
| Day 14 priming administration | Split virus A/Indonesia/5/2005 (3.8 μg) + AS03 (1 dose at Day 14) | Group 2 |
| Day 21 priming administration | Split virus A/Indonesia/5/2005 (3.8 μg) + AS03 (1 dose at Day 21) | Group 1 |

AS03 = oil-in-water emulsion containing DL-α-tocopherol and squalene in an aqueous phase with the non-ionic detergent Tween 80.

III.2. Objectives and Endpoints
Primary Objective:
Demonstrate that H5N1 antigen in association with AS03 administered in accelerated immunization schedules elicits, at day 14 after the second dose, an immune response measured by post-immunization vaccine-homologous virus hemagglutination inhibition (HI) titers that meets or exceeds CBER guidance targets for seroconversion rate and also provides a potentially useful rate of attainment (=50% of subjects) of reciprocal HI titers of ≥40.
Criteria for Evaluation:
H5N1 seroconversion rates (SCR) against A/Indonesia/5/05 virus 14 days after the second dose of H5N1 vaccine. If the lower limit of the 98.75% confidence interval (CI) for SCR is ≥40% in any of the treatment groups, then it is concluded that H5N1 antigen in association with AS03 in the given treatment group elicits an immune response, measured by post-immunization vaccine-homologous virus HI titers, that meets or exceeds CBER guidance targets for SCR.
and
Proportion of subjects with reciprocal HI titers≥40 against A/Indonesia/5/05 virus 14 days after the second dose of H5N1 vaccine (abbreviated SPR for potential "seroprotection rate"). If the lower limit of the 98.75% CI for SPR is ≥50% in any of the treatment groups, then it is concluded that H5N1 antigen in association with AS03 in the given treatment group elicits an immune response, measured by post-immunization vaccine-homologous virus HI titers, that may provide useful population protection within 2 weeks if that accelerated vaccine schedule is applied.
Secondary Objectives:
To demonstrate that H5N1 antigen in association with AS03 administered in accelerated immunization schedules elicits, at Day 14 after the second dose, an immune response measured by post-immunization vaccine-homologous virus HI titers that meets or exceeds Committee for Medicinal Products for Human Use (CHMP) guidance targets for seroconversion rate, incidence rate of post-immunization reciprocal HI titers≥40 and geometric mean fold-rise (CHMP/VWP/263499/2006, CPMP/BWP/214/96).

To demonstrate that H5N1 antigen in association with AS03 administered in accelerated immunization schedules elicits, at Day 21 after the second dose, an immune response measured by post-immunization vaccine-homologous virus HI titers that meets or exceeds CBER guidance targets for seroconversion rate and also provides a potentially useful rate of attainment (=50% of subjects) of reciprocal HI titers of ≥40.

To demonstrate that H5N1 antigen in association with AS03 administered in accelerated immunization schedules elicits, at Day 21 after the second dose, an immune response measured by post-immunization vaccine-homologous virus HI titers that meets or exceeds CHMP guidance targets for seroconversion rate, incidence rate of post-immunization reciprocal HI titers≥40 and geometric mean fold-rise (CHMP/VWP/263499/2006, CPMP/BWP/214/96).

To describe the immunogenicity of the vaccine in the different administration schedules in terms of HI antibodies specific for one or more drift-variant virus strains. This will be evaluated at 7, 14, and 21 days after the second vaccination.

To describe the immunogenicity of the vaccine in the different administration schedules in terms of microneutralization titers specific for one or more drift-variant virus strains. This will be evaluated at 7, 14, and 21 days after the second vaccination.

To further describe the kinetics of the humoral immune response in terms of HI antibodies specific for the vaccine-homologous virus and for one or more drift-variant virus strains, between first and second vaccinations and up to 6 months after the first dose of vaccine.

To further describe the kinetics of the humoral immune response induced by the respective primary vaccination schedules in terms of microneutralization titers specific for one or more drift-variant virus strains. This will be evaluated at Day 42 and 6 months after the first dose of vaccine.

To describe the safety/reactogenicity of the respective vaccination schedules in terms of solicited local and general reactogenicity events, unsolicited adverse events (AEs), medically attended events, and serious adverse events.

Primary and Secondary Endpoints:

The primary immunogenicity endpoint is based on vaccine-homologous virus antibody response in subjects receiving 2 doses of study vaccine, as demonstrated by the HI antibody titer at 14 days after the second dose of H5N1 vaccine.

Observed variable: serum HI antibody titers against vaccine-homologous strains.

Derived variables:
Seroconversion rates.
Proportion of subjects with HI titers≥1:40 against A/Indonesia/5/05 (=seroprotection rates, SPR)

Vaccine-homologous virus and drift variant H5N1 virus antibody responses, as measured by HI antibody response and microneutralization titers (only drift-variant H5N1 virus) at 7, 14, and 21 days after the second dose of H5N1 vaccine. The genetically most-distant variant virus currently available is a Clade 1 virus (A/Vietnam/1194/04); if available, responses to other recent H5N1 isolates may also be tested.

III.3. Vaccine Composition (Table 3)

The preparation of adjuvanted influenza vaccine is essentially made based on the protocol previously described (see US patent application published under US20070141078A1 and incorporated herein by reference). Briefly the study vaccines are formulated and administered as below:

TABLE 3

AS03 adjuvanted pandemic influenza candidate vaccine

| Component | Quantity per dose |
|---|---|
| Active Ingredients | |
| Inactivated split virions A/Indonesia/5/2005 (H5N1) | 3.8 µg HA |
| AS03 Adjuvant | |
| SB62 emulsion | |
| squalene | 10.68 mg |
| DL-α-tocopherol | 11.86 mg |
| Polysorbate 80 (Tween 80) | 4.85 mg |
| Excipients | |
| Polysorbate 80 (Tween 80) | 12.26 µg/µg HA |
| Octoxynol 10 (Triton X-100) | 1.16 µg/µg HA |
| Thiomersal | 5 µg |
| Sodium chloride | 7.5 mg |
| Disodium hydrogen phosphate | 1 mg |
| Potassium dihydrogen phosphate | 0.36 mg |
| Potassium chloride | 0.19 mg |
| Magnesium chloride | 23.27 µg |

The clinical candidate AS03-adjuvanted split virus vaccine is a 2-component vaccine consisting of antigens and adjuvant. At the time of injection, the adjuvant and the antigens (3.8 µg HA) are combined. The volume injected is 0.5 ml. The vaccines are administered in the deltoid region of the non-dominant arm. The vaccine contains the following residuals from the manufacturing process of the drug substance: formaldehyde, ovalbumin, sucrose, thiomersal and sodium deoxycholate.

The virus strain used to manufacture the clinical lots is the H5N1 vaccine strain A/Indonesia/5/2005 recombinant H5N1 prototype vaccine strain, derived from the highly pathogenic A/Indonesia/5/2005 belonging to clade 2 and is made by reverse genetics. The split virus monovalent bulks used to produce vaccine are manufactured following the same procedure as used for GSK Biologicals licensed interpandemic influenza vaccine Fluarix™/α-Rix®.

One dose of reconstituted AS03-adjuvanted pandemic influenza vaccine corresponds to 1 ml. The composition is given in Table 3. One dose contains 3.8 µg HA. The vaccine contains the following residuals from the manufacturing process of the drug substance: formaldehyde, ovalbumin, sucrose, thiomersal and sodium deoxycholate.

Example IV

Phase II Clinical Study to Evaluate the Immunogenicity and Safety of a Single or Double-Dose of the Pandemic Influenza Candidate Vaccine (Split Virus Formulation Adjuvanted with AS03) Given Following a Two-Administration Schedule (21 Days Apart) in Adults Over 60 Years of Age IV.1. Study Design
IV.1.1 Subject:

Phase II, randomized, open study designed to evaluate the immunogenicity and safety of a single (3.8 µg) or double dose (twice 3.8 µg given concomitantly in two different arms, referred to 2×3.8 µg herein below) of the adjuvanted H5N1 vaccine adult dose previously identified in a dose-ranging, phase I trial (Study H5N1-007 conducted in healthy adults aged 18 to 60 years). The candidate vaccine was administered following a two-administration schedule (21 days apart) in adults over 60 years of age. Single and double dose of H5N1 vaccine non adjuvanted have been used as comparator.

IV.1.2. Design 480 subjects aged 61 years old or above, have been allocated in four groups.

H5N1/AS03/3.8 µg HA (also referred to as 3.8/AS group): 180 subjects receiving a single dose (3.8 µg) of the pandemic influenza vaccine (H5N1+AS03) at Day 0 and Day 21.

H5N1/3.8 µg HA (also referred to as 3.8/NoAS group): 60 subjects receiving a single dose (3.8 µg) of the pandemic influenza vaccine non adjuvanted at Day 0 and Day 21.

H5N1/AS03/2×3.8 µg HA (also referred to as 7.5/AS group): 180 subjects receiving a double dose (3.8 µg given twice) of the pandemic influenza vaccine (H5N1+AS03) at Day 0 and Day 21.

H5N1/2×3.8 µg HA (also referred to as 7.5/NoAS group): 60 subjects receiving a double dose (3.8 µg given twice) of the pandemic influenza vaccine non adjuvanted at Day 0 and Day 21.

Subjects in each group have been stratified by age: 61-65 years, 66-70 years and >70 years with the allocation ratio 1:1:1.

All subjects not vaccinated with an influenza vaccine for the 2006-2007 season have received Fluarix™ NH2006/2007 (i.e. interpandemic GSK's influenza vaccine) at least 3 weeks before administration of the first dose of H5N1 vaccine.

IV.1.3. Objectives and Endpoints

Primary Objective:

To evaluate the immunogenicity of the H5N1 vaccine administered as a single or double dose in terms of humoral immune response 21 days after the first and second vaccination (for HI antibody response) and 21 days after the second vaccination (for neutralizing antibody response).

Secondary Objectives:

To evaluate the safety/reactogenicity of the H5N1 vaccine administered as a single or double-dose in terms of:

Percentage, intensity and relationship to vaccination of solicited local and general signs and symptoms during a 7-Day follow-up period (i.e. Day of vaccination and 6 subsequent days) after each dose of vaccine and overall.

Percentage, intensity and relationship to vaccination of unsolicited local and general signs and symptoms during 21 days following the first H5N1 vaccination (i.e. Day of first vaccination and 20 subsequent days) and during 30 days following the second vaccination (i.e. Day of second vaccination and 29 subsequent days).

Occurrence of serious adverse events (SAEs) during the entire study period.

To evaluate the safety of the H5N1 vaccine administered as a single or double-dose based on haematological and biochemical parameters.

To evaluate at days 0, 21 and 42 for all subjects the cell-mediated immune response in terms of Th1-specific activation marker expression (CD40L, IL-2, TNF-α and IFN-γ) after in vitro restimulation of influenza-specific CD4/CD8 T-cells.

Primary Endpoint:

For the humoral immune response in terms of H5N1 HI antibodies, the following parameters (with 95% confidence intervals [CIs]) were calculated for each group:

Geometric mean titres (GMTs) of H5N1 antibody titres at days 0, 21 and 42 for all subjects.

Seroconversion rates (SCR) at days 21 and 42 for all subjects.

Seroconversion factors (SCF) at days 21 and 42 for all subjects.

Seroprotection rates (SPR) at days 0, 21 and 42 for all subjects.

In addition, the humoral immune response in terms of neutralizing antibodies was evaluated in a subset of subjects in the adjuvanted groups (3.8/AS and 7.5/AS groups) using the following parameters (with 95% CIs):

Geometric mean titres (GMTs) of H5N1 antibody titres at days 0 and 42.

Seroconversion rates (SCR) at day 42.

Secondary Endpoints

For the Safety/Reactogenicity Evaluation:

Percentage, intensity and relationship to vaccination of solicited local and general signs and symptoms during a 7-Day follow-up period (i.e. Day of vaccination and 6 subsequent days) after each dose of the H5N1 vaccine and overall.

Percentage, intensity and relationship to vaccination of unsolicited local and general signs and symptoms during 21 days following the first vaccination with the H5N1 vaccine (i.e. Day of first vaccination and 20 subsequent days) and during 30 days following the second vaccination (i.e. Day of second vaccination and 29 subsequent days).

Occurrence of SAEs during the entire study period.

Number and percentage of subjects with normal or abnormal values at each scheduled timepoint (Day 0, Day 2, Day 21, Day 23), for biochemical assessments and for hematological analysis.

For the Cell-Mediated Immunity Response Evaluation:

The following parameters (with 95% CIs) were calculated at days 0, 21, and 42 for all subjects:

Frequency of influenza-specific CD4/CD8 T-cells per $10^6$ in tests producing at least two out of four different Th1-specific activation markers (CD40L, IL-2, TNF-α, IFN-γ)

Frequency of influenza-specific CD4/CD8 T-cells per $10^6$ in tests producing at least CD40L and another immune marker (IL-2, IFN-γ, TNF-α)

Frequency of influenza-specific CD4/CD8 T-cells per $10^6$ in tests producing at least IL-2 and another immune marker (CD40L, IFN-γ, TNF-α)

Frequency of influenza-specific CD4/CD8 T-cells per $10^6$ in tests producing at least TNF-α and another immune marker (IL-2, IFN-γ, CD40L)

Frequency of influenza-specific CD4/CD8 T-cells per 106 in tests producing at least IFN-γ and another immune marker (CD40L, IL-2, TNF-α)

IV.2. Vaccine Administered

Monovalent, split virus, influenza pandemic candidate vaccine formulated from the A/Vietnam/1194/2004 (H5N1) strain, adjuvanted with AS03. The total injected volume was 0.5 ml, and administered intramuscularly. The vaccine is a 2-component vaccine consisting of concentrated inactivated split virion (H5N1) antigens presented in a type I glass vial and of the AS03 adjuvant contained in a pre-filled type I glass syringe. Non adjuvanted H5N1 vaccine has been used as comparator.

The manufacturing process for the monovalent bulks of split, inactivated influenza H5N1 strain is identical to the manufacturing process for the monovalent bulks of GSK Biologicals licensed interpandemic influenza vaccine Fluarix™/α-Rix® (WO02/097072 and WO2008/009309). For the purpose of this clinical trial the virus strains used to manufacture the clinical lots is the H5N1 vaccine strain A/Vietnam/1194/04 NIBRG-14 recombinant H5N1 prototype vaccine strain derived from the A/Vietnam/1194/04 strain (VT strain). The strain has been developed by NIBSC using reverse genetics (a suitable reference is Nicolson et al. 2005, Vaccine, 23, 2943-2952)). The reassortant strain combines the H5 and N1 segments to the A/PR/8/34 strain backbone, and the H5 was engineered to eliminate the polybasic stretch of amino-acids at the HA cleavage site that is responsible for high virulence of the original strains. The active substance of the pandemic influenza vaccine candidates is a formaldehyde inactivated split virus antigen.

The AS03 adjuvanted inactivated split virus influenza vaccines are 2 component vaccines consisting of concentrated inactivated split virion (H5N1) antigens presented in a type I glass vial and of the AS03 adjuvant contained in a pre-filled type I glass syringe. One adult dose of reconstituted AS03-adjuvanted vaccine corresponds to 0.5 ml. Their composition is given in Table 4.

TABLE 4

Composition of the reconstituted AS03 adjuvanted influenza candidate vaccines

| Component | Quantity per dose |
|---|---|
| ACTIVE INGREDIENTS | |
| Inactivated split virions A/VietNam/1194/2004 NIBRG-14 (H5N1) | 3.8 µg HA |
| AS03 ADJUVANT | |
| SB62 emulsion | |
| squalene | 10.68 mg |
| DL-α-tocopherol | 11.86 mg |
| Polysorbate 80 (Tween 80) | 4.85 mg |
| Polysorbate 80 (Tween 80) | 7.67 µg/µg HA |
| Octoxynol 10 (Triton X-100) | 1.16 µg/µg HA |

TABLE 4-continued

Composition of the reconstituted AS03 adjuvanted influenza candidate vaccines

| Component | Quantity per dose |
|---|---|
| EXCIPIENTS | |
| Thiomersal | 5 µg |
| Sodium chloride | 3.7 mg |
| Disodium hydrogen phosphate | 485 µg |
| Potassium dihydrogen phosphate | 175 µg |
| Potassium chloride | 94 µg |
| Magnesium chloride hexahydrate | 11.7 µg |

For this study, 0.25 ml each of the content of the prefilled syringe containing the adjuvant and 0.25 ml each of the content of the vial containing monovalent split influenza virus antigen was used. After extemporaneous mixing of the contents, a 0.5 ml dose was withdrawn into the syringe and injected intramuscularly. At the time of injection, the content of the prefilled syringe containing the adjuvant was injected into the vial that contains the concentrated inactivated split virion antigens. One dose of the reconstituted the AS03-adjuvanted influenza candidate vaccine corresponds to 0.5 ml, containing 3.8 µg haemagglutinin (HA). If necessary, the formulation process was adapted to ensure that the same amounts of antigen and adjuvants are present in the final vaccine. Thiomersal is added as a preservative at a concentration of 10 µg/ml (5 µg per dose).

IV.3. Immunogenicity Results
IV.3.1. HI Antibody Response
IV.3.1.1. Geometric Mean Titers The results are shown in Table 5 (anti-Vietnam (VT) response) and in Table 6 (anti-Indonesia (IN) response) and in FIG. 1 (response against both strains).

TABLE 5

Seropositivity rates and GMTs of H5N1 HI antibodies against the vaccine strain A/Vietnam/1194/2004 (H5N1) (ATP cohort for immunogenicity)

| Antibodies against | Group | Timing | N | n | % | >=10 (1:dil) 95% CI LL | UL | GMT value | 95% CI LL | UL | Min | Max |
|---|---|---|---|---|---|---|---|---|---|---|---|---|
| A/Vietnam | 7.5/NoAS | PRE | 44 | 16 | 36.4 | 22.4 | 52.2 | 8.8 | 6.6 | 11.8 | <10.0 | 640.0 |
| | | PI(D21) | 44 | 26 | 59.1 | 43.2 | 73.7 | 20.8 | 13.0 | 33.3 | <10.0 | 1280.0 |
| | | PII(D42) | 44 | 32 | 72.7 | 57.2 | 85.0 | 25.3 | 16.0 | 40.1 | <10.0 | 640.0 |
| | 3.8/NoAS | PRE | 54 | 21 | 38.9 | 25.9 | 53.1 | 9.7 | 7.3 | 13.0 | <10.0 | 453.0 |
| | | PI(D21) | 54 | 32 | 59.3 | 45.0 | 72.4 | 16.8 | 11.7 | 24.0 | <10.0 | 640.0 |
| | | PII(D42) | 54 | 36 | 66.7 | 52.5 | 78.9 | 22.7 | 15.1 | 34.1 | <10.0 | 1280.0 |
| | 7.5/AS | PRE | 145 | 52 | 35.9 | 28.1 | 44.2 | 10.2 | 8.4 | 12.5 | <10.0 | 1280.0 |
| | | PI(D21) | 145 | 130 | 89.7 | 83.5 | 94.1 | 69.4 | 52.1 | 92.3 | <10.0 | 5120.0 |
| | | PII(D42) | 145 | 142 | 97.9 | 94.1 | 99.6 | 237.3 | 191.9 | 293.6 | <10.0 | 14480.0 |
| | 3.8/AS | PRE | 152 | 62 | 40.8 | 32.9 | 49.0 | 11.3 | 9.2 | 13.9 | <10.0 | 5120.0 |
| | | PI(D21) | 152 | 122 | 80.3 | 73.0 | 86.3 | 50.0 | 38.1 | 65.6 | <10.0 | 3620.0 |
| | | PII(D42) | 152 | 142 | 93.4 | 88.2 | 96.8 | 126.8 | 99.4 | 161.7 | <10.0 | 5120.0 |

7.5/NoAS = H5N1/[2 × 3.8 µg HA];
3.8/NoAS = H5N1/[1 × 3.8 µg HA];
7.5/AS = H5N1/[2 × 3.8 µg HA/AS03];
3.8/AS = H5N1/[1 × 3.8 µg HA/AS03];
N = number of subjects with available results;
95% CI = 95% confidence interval;
LL = Lower Limit;
UL = Upper Limit;
MIN/MAX = Minimum/Maximum;
PRE = Pre-vaccination at Day 0;
PI (D21) = Post-vaccination at Day 21;
PII (D42) = Post-vaccination at Day 42

Intermediate Conclusions for the Anti-VT Response:

Whether assessed 21 days after the first vaccination, or 21 days after the second vaccination, the GMTs were significantly higher in the groups of subjects vaccinated with an adjuvanted vaccine as compared to subjects vaccinated with an unadjuvanted vaccine (50-69.4 compared to 16.8-20.8 at PI (D21); 126.8-237.3 compared to 22.7-25.3 at PII (D42)). The GMTs were also comparable with either 3.8 or 2×3.8 formulations, when the vaccine was unadjuvanted, at both assessment times.

When assessed 21 days after the first vaccination, the GMTs obtained in the unadjuvanted groups were comparable with either 3.8 or 2×3.8 formulations. However when assessed at 21 days after the second vaccination, the GMTs obtained in the adjuvanted groups were higher with the 2×3.8 formulation (237.3), as compared with the 3.8 formulation (126.8).

IV.3.1.2. Seroconversion Rates

The results are shown in Table 7 and in FIG. 2 (response against both strains).

TABLE 7

Seroconversion rates for H5N1 HI antibodies against A/Vietnam/1194/2004 and A/Indonesia/5/2005 at Day 21 and Day 42 post-vaccination (ATP cohort for immunogenicity)

| Antibodies against | Group | Timing | N | n | SCR % | 95% CI LL | 95% CI UL |
|---|---|---|---|---|---|---|---|
| A/Vietnam | 7.5/NoAS | PI(D21) | 44 | 8 | 18.2 | 8.2 | 32.7 |
| | | PII(D42) | 44 | 10 | 22.7 | 11.5 | 37.8 |
| | 3.8/NoAS | PI(D21) | 54 | 8 | 14.8 | 6.6 | 27.1 |
| | | PII(D42) | 54 | 12 | 22.2 | 12.0 | 35.6 |

TABLE 6

Seropositivity rates and GMTs of H5N1 HI antibodies against the A/Indonesia/5/2005 strain (ATP cohort for immunogenicity)

| Antibodies against | Group | Timing | N | n | >=10 (1:dil) % | 95% CI LL | 95% CI UL | GMT value | 95% CI LL | 95% CI UL | Min | Max |
|---|---|---|---|---|---|---|---|---|---|---|---|---|
| A/Indonesia | 7.5/NoAS | PRE | 44 | 0 | 0.0 | 0.0 | 8.0 | 5.0 | 5.0 | 5.0 | <10.0 | <10.0 |
| | | PI(D21) | 44 | 5 | 11.4 | 3.8 | 24.6 | 5.6 | 5.0 | 6.3 | <10.0 | 40.0 |
| | | PII(D42) | 44 | 8 | 18.2 | 8.2 | 32.7 | 6.3 | 5.2 | 7.6 | <10.0 | 113.0 |
| | 3.8/NoAS | PRE | 54 | 2 | 3.7 | 0.5 | 12.7 | 5.2 | 4.9 | 5.5 | <10.0 | 20.0 |
| | | PI(D21) | 54 | 2 | 3.7 | 0.5 | 12.7 | 5.3 | 4.8 | 5.9 | <10.0 | 80.0 |
| | | PII(D42) | 54 | 7 | 13.0 | 5.4 | 24.9 | 6.1 | 5.1 | 7.4 | <10.0 | 226.0 |
| | 7.5/AS | PRE | 145 | 4 | 2.8 | 0.8 | 6.9 | 5.1 | 5.0 | 5.2 | <10.0 | 14.0 |
| | | PI(D21) | 145 | 48 | 33.1 | 25.5 | 41.4 | 8.6 | 7.3 | 10.1 | <10.0 | 1810.0 |
| | | PII(D42) | 145 | 108 | 74.5 | 66.6 | 81.4 | 24.4 | 19.9 | 30.0 | <10.0 | 1280.0 |
| | 3.8/AS | PRE | 152 | 2 | 1.3 | 0.2 | 4.7 | 5.1 | 5.0 | 5.1 | <10.0 | 14.0 |
| | | PI(D21) | 152 | 36 | 23.7 | 17.2 | 31.3 | 6.9 | 6.2 | 7.7 | <10.0 | 160.0 |
| | | PII(D42) | 152 | 83 | 54.6 | 46.3 | 62.7 | 13.7 | 11.3 | 16.4 | <10.0 | 320.0 |

7.5/NoAS = H5N1 [2 × 3.8 μg HA];
3.8/NoAS = H5N1 [1 × 3.8 μg HA];
7.5/AS = H5N1 [2 × 3.8 μg HA/AS03];
3.8/AS = H5N1 [1 × 3.8 μg HA/AS03];
N = number of subjects with available results;
95% CI = 95% confidence interval;
LL = Lower Limit;
UL = Upper Limit;
MIN/MAX = Minimum/Maximum;
PRE = Pre-vaccination at Day 0;
PI (D21) = Post-vaccination at Day 21;
PII (D42) = Post-vaccination at Day 42

Intermediate Conclusions for the Anti-IN Response:

Whether assessed 21 days after the first vaccination, or 21 days after the second vaccination, the GMTs were significantly higher in the groups of subjects vaccinated with an adjuvanted vaccine compared to subjects vaccinated with an unadjuvanted vaccine (6.9-8.6 compared to 5.3-5.6 at PI (D21); 13.7-24.4 compared to 6.1-6.3 at PII (D42)). The GMTs were also comparable with either 3.8 or 2×3.8 formulations, when the vaccine was unadjuvanted, at both assessment times.

When assessed 21 days after the first vaccination, the GMTs obtained in the unadjuvanted groups were comparable with either 3.8 or 2×3.8 formulations. However when assessed at 21 days after the second vaccination, the GMTs obtained in the adjuvanted groups were higher with the 2×3.8 formulation (237.3), as compared with the 3.8 formulation (126.8).

TABLE 7-continued

Seroconversion rates for H5N1 HI antibodies against A/Vietnam/1194/2004 and A/Indonesia/5/2005 at Day 21 and Day 42 post-vaccination (ATP cohort for immunogenicity)

| Antibodies against | Group | Timing | N | n | SCR % | 95% CI LL | 95% CI UL |
|---|---|---|---|---|---|---|---|
| | 7.5/AS | PI(D21) | 145 | 76 | 52.4 | 44.0 | 60.8 |
| | | PII(D42) | 145 | 128 | 88.3 | 81.9 | 93.0 |
| | 3.8/AS | PI(D21) | 152 | 69 | 45.4 | 37.3 | 53.7 |
| | | PII(D42) | 152 | 110 | 72.4 | 64.5 | 79.3 |
| A/Indonesia | 7.5/NoAS | PI(D21) | 44 | 1 | 2.3 | 0.1 | 12.0 |
| | | PII(D42) | 44 | 2 | 4.5 | 0.6 | 15.5 |
| | 3.8/NoAS | PI(D21) | 54 | 1 | 1.9 | 0.0 | 9.9 |
| | | PII(D42) | 54 | 2 | 3.7 | 0.5 | 12.7 |

TABLE 7-continued

Seroconversion rates for H5N1 HI antibodies against A/Vietnam/1194/2004 and A/Indonesia/5/2005 at Day 21 and Day 42 post-vaccination (ATP cohort for immunogenicity)

| Antibodies against | Group | Timing | N | n | % | SCR 95% CI LL | UL |
|---|---|---|---|---|---|---|---|
|  | 7.5/AS | PI(D21) | 145 | 13 | 9.0 | 4.9 | 14.8 |
|  |  | PII(D42) | 145 | 58 | 40.0 | 32.0 | 48.5 |
|  | 3.8/AS | PI(D21) | 152 | 5 | 3.3 | 1.1 | 7.5 |
|  |  | PII(D42) | 152 | 35 | 23.0 | 16.6 | 30.5 |

7.5/NoAS = H5N1 [2 × 3.8 µg HA];
3.8/NoAS = H5N1 [1 × 3.8 µg HA];
7.5/AS = H5N1 [2 × 3.8 µg HA/AS03];
3.8/AS = H5N1 [1 × 3.8 µg HA/AS03];
N = number of subjects with available results;
PI(D21) = Post vaccination at 21 days;
PII(D42) = Post vaccination at 42 days;
marital/% = number/percentage of subjects with either a pre-vaccination titre <1:10 and post-vaccination titre ≥1:40 ora pre-vaccination titre ≥1:10 and a minimum 4-fold increase in pot-vaccination titre;
95% confidence interval,
LL = Lower Limit,
UL = Upper Limit Intermediate Conclusion for Seroconversion Rates for the Anti-VT Response In subjects from the adjuvanted groups, the >30% SCR threshold required by the CHMP for adults aged >60 years was exceeded 21 days after the first vaccination and SCR increased significantly 21 days after the second vaccination. By contrast none of the unadjuvanted groups reached the >30% SCR threshold, whether assessed 21 days after the first or 21 days after the second vaccination. When assessed 21 days after the second vaccination, a higher SCR was obtained in the adjuvanted groups with the 2×3.8 formulation (88.3%), as compared with the 3.8 formulation (72.4%).

Intermediate Conclusion for Seroconversion Rates for the Anti-IN Response

The >30% SCR threshold required by the CHMP for adults aged >60 years was met 21 days after the second vaccination in subjects vaccinated with the adjuvanted 2×3.8 µg formulation. When assessed 21 days after the second vaccination, a higher SCR was obtained in the adjuvanted groups with the 2×3.8 formulation (40%), as compared with the 3.8 formulation (23%).

IV.3.1.3. Seroprotection Rates

The results are shown in Table 8 and in FIG. 3 (response against both strains).

TABLE 8

Seroprotection rates for H5N1 HI antibodies against A/Vietnam/1194/2004 and A/Indonesia/5/2005 (ATP cohort for immunogenicity)

| Antibodies against | Group | Timing | N | n | % | SCR 95% CI LL | UL |
|---|---|---|---|---|---|---|---|
| A/Vietnam | 7.5/NoAS | PRE | 44 | 2 | 4.5 | 0.6 | 15.5 |
|  |  | PI(D21) | 44 | 15 | 34.1 | 20.5 | 49.9 |
|  |  | PII(D42) | 44 | 17 | 38.6 | 24.4 | 54.5 |
|  | 3.8/NoAS | PRE | 54 | 7 | 13.0 | 5.4 | 24.9 |
|  |  | PI(D21) | 54 | 15 | 27.8 | 16.5 | 41.6 |
|  |  | PII(D42) | 54 | 19 | 35.2 | 22.7 | 49.4 |
|  | 7.5/AS | PRE | 145 | 23 | 15.9 | 10.3 | 22.8 |
|  |  | PI(D21) | 145 | 90 | 62.1 | 53.6 | 70.0 |
|  |  | PII(D42) | 145 | 139 | 95.9 | 91.2 | 98.5 |
|  | 3.8/AS | PRE | 152 | 28 | 18.4 | 12.6 | 25.5 |
|  |  | PI(D21) | 152 | 93 | 61.2 | 53.0 | 69.0 |
|  |  | PII(D42) | 152 | 127 | 83.6 | 76.7 | 89.1 |
| A/Indonesia | 7.5/NoAS | PRE | 44 | 0 | 0.0 | 0.0 | 8.0 |
|  |  | PI(D21) | 44 | 1 | 2.3 | 0.1 | 12.0 |
|  |  | PII(D42) | 44 | 2 | 4.5 | 0.6 | 15.5 |
|  | 3.8/NoAS | PRE | 54 | 0 | 0.0 | 0.0 | 6.6 |
|  |  | PI(D21) | 54 | 1 | 1.9 | 0.0 | 9.9 |
|  |  | PII(D42) | 54 | 2 | 3.7 | 0.5 | 12.7 |
|  | 7.5/AS | PRE | 145 | 0 | 0.0 | 0.0 | 2.5 |
|  |  | PI(D21) | 145 | 13 | 9.0 | 4.9 | 14.8 |
|  |  | PII(D42) | 145 | 59 | 40.7 | 32.6 | 49.2 |
|  | 3.8/AS | PRE | 152 | 0 | 0.0 | 0.0 | 2.4 |
|  |  | PI(D21) | 152 | 5 | 3.3 | 1.1 | 7.5 |
|  |  | PII(D42) | 152 | 35 | 23.0 | 16.6 | 30.5 |

7.5/NoAS = H5N1 [2 × 3.8 µg HA];
3.8/NoAS = H5N1 [1 × 3.8 µg HA];
7.5/AS = H5N1 [2 × 3.8 µg HA/AS03];
3.8/AS = H5N1 [1 × 3.8 µg HA/AS03];
N = number of subjects with available results;
n/% = number/percentage of subjects with titre within the specified range;
PRE = Pre-vaccination;
PI(D21) = Post vaccination at day 21;
PII(D42) = Post vaccination at day 42

Intermediate Conclusion for Seroprotection Rates for the Anti-VT Response

In subjects from the adjuvanted groups, the >60% SPR threshold required by the CHMP for adults aged >60 years was exceeded 21 days after the first vaccination and increased significantly 21 days after the second vaccination. By contrast none of the unadjuvanted groups reached the ≥60% SCR threshold, either 21 days after the first or 21 days after the second vaccination. When assessed 21 days after the second vaccination, a higher SPR was obtained in the adjuvanted groups with the 2×3.8 formulation (95.9%), as compared with the 3.8 formulation (83.6%).

Intermediate Conclusion for Seroprotection Rates for the Anti-IN Response

None of the groups reached the >60% SCR threshold required by the European Committee for Medicinal Products for Human Use (CHMP) for adults aged >60 years, either 21 days after the first or 21 days after the second vaccination. When assessed 21 days after the second vaccination, a higher SPR was obtained in the adjuvanted groups with the 2×3.8 formulation (40.7%), as compared with the 3.8 formulation (23%).

IV.3.1.4. Seroconversion Factors

The results are shown in Table 9 and in FIG. 4 (response against both strains).

TABLE 9

Seroconversion factor for H5N1 HI antibodies against A/Vietnam/1194/2004 and A/Indonesia/5/2005 (ATP cohort for immunogenicity)

| Antibodies against | Group | Timing | N | SCF Value | 95% CI LL | 95% CI UL |
|---|---|---|---|---|---|---|
| A/Vietnam/04 AB | 7.5/NoAS | PI(D21) | 44 | 2.4 | 1.7 | 3.4 |
| | | PII(D42) | 44 | 2.9 | 2.0 | 4.1 |
| | 3.8/NoAS | PI(D21) | 54 | 1.7 | 1.3 | 2.3 |
| | | PII(D42) | 54 | 2.3 | 1.6 | 3.3 |
| | 7.5/AS | PI(D21) | 145 | 6.8 | 5.3 | 8.6 |
| | | PII(D42) | 145 | 23.2 | 18.5 | 29.0 |
| | 3.8/AS | PI(D21) | 152 | 4.4 | 3.5 | 5.5 |
| | | PII(D42) | 152 | 11.2 | 8.9 | 14.1 |
| A/Indonesia/5/05 | 7.5/NoAS | PI(D21) | 44 | 1.1 | 1.0 | 1.3 |
| | | PII(D42) | 44 | 1.3 | 1.0 | 1.5 |
| | 3.8/NoAS | PI(D21) | 54 | 1.0 | 0.9 | 1.1 |
| | | PII(D42) | 54 | 1.2 | 1.0 | 1.4 |
| | 7.5/AS | PI(D21) | 145 | 1.7 | 1.4 | 2.0 |
| | | PII(D42) | 145 | 4.8 | 3.9 | 5.9 |
| | 3.8/AS | PI(D21) | 152 | 1.4 | 1.2 | 1.5 |
| | | PII(D42) | 152 | 2.7 | 2.2 | 3.2 |

7.5/NoAS = H5N1 [2 × 3.8 µg HA];
3.8/NoAS = H5N1 [1 × 3.8 µg HA];
7.5/AS = H5N1 [2 × 3.8 µg HA/AS03];
3.8/AS = H5N1 [1 × 3.8 µg HA/AS03];
N = number of subjects with available results n/% = number/percentage of subjects with titre within the specified range;
PRE = Pre-vaccination;
PI(D21) = Post vaccination at day 21;
PII(D42) = Post vaccination at day 42

Intermediate Conclusion for Seroconversion Factors for the Anti-VT Response

In subjects from the adjuvanted groups, the >2.0 SCF threshold required by the CHMP for adults aged >60 years was exceeded 21 days after the first vaccination and increased significantly 21 days after the second vaccination.

In subjects from the unadjuvanted groups, the >2.0 SCF threshold was exceeded in subjects vaccinated with the 2×3.8 formulation 21 days after the first vaccination and did not show significant increase 21 days after the second vaccination. The ≥2.0 SCF threshold was exceeded in subjects vaccinated with the 3.75 formulation only 21 days after the second vaccination. When assessed 21 days after the second vaccination, a higher SCF was obtained in the adjuvanted groups with the 2×3.8 formulation (23.2), as compared with the 3.8 formulation (11.2).

Intermediate Conclusion for Seroconversion Factors for the Anti-IN Response

In subjects from the adjuvanted groups, the >2.0 SCF threshold required by the CHMP for adults aged >60 years was met 21 days after the second vaccination. When assessed 21 days after the second vaccination, a higher SCF was obtained in the adjuvanted groups with the 2×3.8 formulation (4.8), as compared with the 3.8 formulation (2.7).

IV.3.2. HI Antibody Response, Stratified by Baseline Sero-Status (Anti-Vietnam Response)

IV.3.2.1. Seroconversion Rates

The results are shown in Table 10 (subjects seronegative to A/Vietnam/1194/2004 before vaccination), in Table 11 (subjects seropositive to A/Vietnam/1194/2004 before vaccination) and in FIG. 5.

TABLE 10

Seroconversion rate (SCR) for H5N1 HI antibodies against A/Vietnam/1294/2004 at post-vaccination time-point Day 21 and Day 42 (Initially seronegative cohort)

| Antibodies against | Group | Timing | N | n | SCR % | 95% CI LL | 95% CI UL |
|---|---|---|---|---|---|---|---|
| A/Vietnam | 7.5/NoAS | PI(D21) | 28 | 4 | 14.3 | 4.0 | 32.7 |
| | | PII(D42) | 28 | 5 | 17.9 | 6.1 | 36.9 |
| | 3.8/NoAS | PI(D21) | 33 | 6 | 18.2 | 7.0 | 35.5 |
| | | PII(D42) | 33 | 7 | 21.2 | 9.0 | 38.9 |
| | 7.5/AS | PI(D21) | 93 | 47 | 50.5 | 40.0 | 61.1 |
| | | PII(D42) | 93 | 88 | 94.6 | 87.9 | 98.2 |
| | 3.8/AS | PI(D21) | 90 | 40 | 44.4 | 34.0 | 55.3 |
| | | PII(D42) | 90 | 66 | 73.3 | 63.0 | 82.1 |

7.5/NoAS = H5N1 [2 × 3.8 µg HA];
3.8/NoAS = H5N1 [1 × 3.8 µg HA];
7.5/AS = H5N1 [2 × 3.8 µg HA/AS03];
3.8/AS = H5N1 [1 × 3.8 µg HA/AS03];
Seroconversion defined as: For initially seronegative subjects, antibody titre >=40 after vaccination, For initially seropositive subjects, antibody titre after vaccination >=4 fold the pre-vaccination antibody titre;
N = Number of subjects with pre- and post-vaccination results available;
n/% = Number/percentage of seroconverted subjects;
95% CI = 95% confidence interval,
LL = Lower Limit;
UL = Upper Limit;
PI(D21) = Post-vaccination at Day 21;
PII(D42) = Post-vaccination at Day 42

Intermediate Conclusion for Seroconversion Rates for the Anti-VT Response in Subjects Initially Seronegative to A/Vietnam/1194/2004

In subjects from the adjuvanted groups, the >30% SCR threshold required by the CHMP for adults aged >60 years was exceeded 21 days after the first vaccination and SCR increased significantly 21 days after the second vaccination. By contrast none of the unadjuvanted groups reached the >30% SCR threshold, whether assessed 21 days after the first or 21 days after the second vaccination. When assessed 21 days after the second vaccination, a higher SCR was obtained in the adjuvanted groups with the 2×3.8 formulation (94.6%), as compared with the 3.8 formulation (73.3%).

TABLE 11

Seroconversion rate (SCR) for H5N1 HI antibodies against A/Vietnam/1294/2004 at post-vaccination time-points Day 21 and Day 42 (Initially seropositive cohort)

| Antibodies against | Group | Timing | N | n | SCR % | 95% CI LL | 95% CI UL |
|---|---|---|---|---|---|---|---|
| A/Vietnam | 7.5/NoAS | PI(D21) | 16 | 4 | 25.0 | 7.3 | 52.4 |
| | | PII(D42) | 16 | 5 | 31.3 | 11.0 | 58.7 |
| | 3.8/NoAS | PI(D21) | 21 | 2 | 9.5 | 1.2 | 30.4 |
| | | PII(D42) | 21 | 5 | 23.8 | 8.2 | 47.2 |
| | 7.5/AS | PI(D21) | 52 | 29 | 55.8 | 41.3 | 69.5 |
| | | PII(D42) | 52 | 40 | 76.9 | 63.2 | 87.5 |

TABLE 11-continued

Seroconversion rate (SCR) for H5N1 HI antibodies against A/Vietnam/1294/2004 at post-vaccination time-points Day 21 and Day 42 (Initially seropositive cohort)

| Antibodies against | Group | Timing | N | n | SCR % | 95% CI LL | 95% CI UL |
|---|---|---|---|---|---|---|---|
| | 3.8/AS | PI(D21) | 62 | 29 | 46.8 | 34.0 | 59.9 |
| | | PII(D42) | 62 | 44 | 71.0 | 58.1 | 81.8 |

7.5/NoAS = H5N1 [2 × 3.8 µg HA];
3.8/NoAS = H5N1 [1 × 3.8 µg HA];
7.5/AS = H5N1 [2 × 3.8 µg HA/AS03];
3.8/AS = H5N1 [1 × 3.8 µg HA/AS03];
Seroconversion defined as: For initially seronegative subjects, antibody titre >=40 after vaccination, For initially seropositive subjects, antibody titre after vaccination >=4 fold the pre-vaccination antibody titre;
N = Number of subjects with pre- and post-vaccination results available;
n/% = Number/percentage of seroconverted subjects;
95% CI = 95% confidence interval,
LL = Lower Limit,
UL = Upper Limit;
PI(D21) = Post-vaccination at Day 21;
PII(D42) = Post-vaccination at Day 42

Intermediate Conclusion for Seroconversion Rates for the Anti-VT Response in Subjects Initially Seropositive to A/Vietnam/1194/2004

In subjects from the adjuvanted groups, the >30% SCR threshold required by the CHMP for adults aged >60 years was exceeded 21 days after the first vaccination, although no further significant increase was observed 21 days after the second vaccination. Within non-adjvuanted groups, only the 2×3.8 formulation reached the >30% SCR threshold, 21 days after the second vaccination. No significant difference was observed in the adjuvanted groups, between the 2×3.8 formulation and the 3.8 formulation, when assessed 21 days after the first and 21 days after the second vaccination.

IV.3.2.2. Seroprotection Rates

The results are shown in Table 12 (subjects seronegative to A/Vietnam/1194/2004 before vaccination), in Table 13 (subjects seropositive to A/Vietnam/1194/2004 before vaccination) and in FIG. 6.

TABLE 12

Seroprotection rates (SPR) for H5N1 HI antibodies against A/vietnam/1294/2004 at Day 0, Day 21 and Day 42 (Initially seronegative cohort)

| Antibodies against | Group | Timing | N | n | SPR % | 95% CI LL | 95% CI UL |
|---|---|---|---|---|---|---|---|
| A/Vietnam | 7.5/NoAS | PRE | 28 | 0 | 0.0 | 0.0 | 12.3 |
| | | PI(D21) | 28 | 4 | 14.3 | 4.0 | 32.7 |
| | | PII(D42) | 28 | 5 | 17.9 | 6.1 | 36.9 |
| | 3.8/NoAS | PRE | 33 | 0 | 0.0 | 0.0 | 10.6 |
| | | PI(D21) | 33 | 6 | 18.2 | 7.0 | 35.5 |
| | | PII(D42) | 33 | 7 | 21.2 | 9.0 | 38.9 |
| | 7.5/AS | PRE | 93 | 0 | 0.0 | 0.0 | 3.9 |
| | | PI(D21) | 93 | 47 | 50.5 | 40.0 | 61.1 |
| | | PII(D42) | 93 | 88 | 94.6 | 87.9 | 98.2 |
| | 3.8/AS | PRE | 90 | 0 | 0.0 | 0.0 | 4.0 |
| | | PI(D21) | 90 | 40 | 44.4 | 34.0 | 55.3 |
| | | PII(D42) | 90 | 66 | 73.3 | 63.0 | 82.1 |

7.5/NoAS = H5N1 [2 × 3.8 µg HA];
3.8/NoAS = H5N1 [1 × 3.8 µg HA];
7.5/AS = H5N1 [2 × 3.8 µg HA/AS03];
3.8/AS = H5N1 [1 × 3.8 µg HA/AS03];
N = Number of subjects with available results;
n/% = Number/percentage of seroprotected subjects (HI titre >= 40);
95% CI = 95% confidence interval,
LL = Lower Limit,
UL = Upper Limit;
PRE = Pre-vaccination;
PI(D21) = Post-vaccination at Day 21;
PII(D42) = Post-vaccination at Day 42

Intermediate Conclusion for Seroprotection Rates for the Anti-VT Response in Subjects Initially Seronegative to A/Vietnam/1194/2004

In subjects from the adjuvanted groups, the >60% SPR threshold required by the CHMP for adults aged >60 years was exceeded 21 days after the second vaccination and there was a significant increase in SPR from 21 days after the first vaccination to 21 days after the second vaccination. None of the unadjuvanted groups reached the >60% SPR threshold, whether assessed 21 days after the first or 21 days after the second vaccination. When assessed 21 days after the second vaccination, a higher SPR was obtained in the adjuvanted groups with the 2×3.8 formulation (94.6%), as compared with the 3.8 formulation (73.3%).

TABLE 13

Seroprotection rates (SPR) for H5N1 HI antibodies against A/Vietnam/1294/2004 at D0, D21 and D42 (Initially seropositive cohort)

| Antibodies against | Group | Timing | N | n | SPR % | 95% CI LL | 95% CI UL |
|---|---|---|---|---|---|---|---|
| A/Vietnam | 7.5/NoAS | PRE | 16 | 2 | 12.5 | 1.6 | 38.3 |
| | | PI(D21) | 16 | 11 | 68.8 | 41.3 | 89.0 |
| | | PII(D42) | 16 | 12 | 75.0 | 47.6 | 92.7 |
| | 3.8/NoAS | PRE | 21 | 7 | 33.3 | 14.6 | 57.0 |
| | | PI(D21) | 21 | 9 | 42.9 | 21.8 | 66.0 |
| | | PII(D42) | 21 | 12 | 57.1 | 34.0 | 78.2 |
| | 7.5/AS | PRE | 52 | 23 | 44.2 | 30.5 | 58.7 |
| | | PI(D21) | 52 | 43 | 82.7 | 69.7 | 91.8 |
| | | PII(D42) | 52 | 51 | 98.1 | 89.7 | 100 |

TABLE 13-continued

Seroprotection rates (SPR) for H5N1 HI antibodies against
A/Vietnam/1294/2004 at D0, D21 and D42 (Initially seropositive cohort)

| Antibodies against | Group | Timing | N | n | % | SPR 95% CI LL | UL |
|---|---|---|---|---|---|---|---|
| | 3.8/AS | PRE | 62 | 28 | 45.2 | 32.5 | 58.3 |
| | | PI(D21) | 62 | 53 | 85.5 | 74.2 | 93.1 |
| | | PII(D42) | 62 | 61 | 98.4 | 91.3 | 100 |

7.5/NoAS = H5N1 [2 × 3.8 µg HA];
3.8/NoAS = H5N1 [1 × 3.8 µg HA];
7.5/AS = H5N1 [2 × 3.8 µg HA/AS03];
3.8/AS = H5N1 [1 × 3.8 µg HA/AS03];
N = Number of subjects with available results;
n/% = Number/percentage of seroprotected subjects (HI titre >= 40);
95% CI = 95% confidence interval,
LL = Lower Limit,
UL = Upper Limit;
PRE = Pre-vaccination;
PI(D21) = Post vaccination at Day 21;
PII(D42) = post-vaccination at Day 42

Intermediate Conclusion for Seroprotection Rates for the Anti-VT Response in Subjects Initially Seropositive to A/Vietnam/1194/2004

In subjects from the adjuvanted groups, the >60% SPR threshold required by the CHMP for adults aged >60 years was exceeded 21 days after the first vaccination, although no further significant increase was observed 21 days after the second vaccination. Within non-adjuvanted groups, only the 2×3.8 formulation reached the >60% SCR threshold, 21 days after the second vaccination. No significant difference was observed in the adjuvanted groups, between the 2×3.8 formulation and the 3.8 formulation, when assessed 21 days after the first and 21 days after the second vaccination.

IV.3.2.3. Seroconversion Factors

The results are shown in Table 14 (subjects seronegative to A/Vietnam/1194/2004 before vaccination) and in Table 15 (subjects seropositive to A/Vietnam/1194/2004 before vaccination).

TABLE 14

Seroconversion factor (SCF) for H5N1 HI antibodies against
A/Vietnam/1294/2004 strain at D21 and D42 post-vaccination (Initially
seronegative cohort, ATP cohort for immunogenicity)

| Antibodies against | Group | Timing | N | Value | SCF 95% CI LL | UL |
|---|---|---|---|---|---|---|
| A/Vietnam | 7.5/NoAS | PI(D21) | 28 | 2.1 | 1.3 | 3.4 |
| | | PII(D42) | 28 | 2.6 | 1.6 | 4.3 |
| | 3.8/NoAS | PI(D21) | 33 | 1.9 | 1.3 | 2.9 |
| | | PII(D42) | 33 | 2.7 | 1.6 | 4.5 |
| | 7.5/AS | PI(D21) | 93 | 8.0 | 5.9 | 11.0 |
| | | PII(D42) | 93 | 39.7 | 31.5 | 50.0 |
| | 3.8/AS | PI(D21) | 90 | 5.1 | 3.7 | 6.9 |
| | | PII(D42) | 90 | 16.0 | 11.7 | 22.0 |

7.5/NoAS = H5N1 [2 × 3.8 µg HA];
3.8/NoAS = H5N1 [1 × 3.8 µg HA];
7.5/AS = H5N1 [2 × 3.8 µg HA/AS03];
3.8/AS = H5N1 [1 × 3.8 µg HA/AS03];
N = Number of subjects with pre- and post-vaccination results available;
SCF = Seroconversion Factor or geometric mean ratio (mean[log10(POST/PRE)]);
95% CI = 95% confidence interval,
LL = Lower Limit,
UL = Upper Limit;
PI(D21) = Post-vaccination at Day 21;
PII(D42) = Post-vaccination at Day 42

Intermediate Conclusion for Seroconversion Factors for the Anti-VT Response in Subjects Initially Seronegative to A/Vietnam/1194/2004

The >2.0 SCF threshold was reached by all groups as after 21 days after the first vaccination, except in the non-adjuvanted group with the 3.8 formulation (1.9). 21 days after the second vaccination, all groups reached the threshold. A significant increase from 21 days after the first vaccination to 21 days after the second vaccination was observed in the adjuvanted groups, yet such significant increase was not observed in the non-adjuvanted groups.

TABLE 15

Seroconversion factor (SCF) for H5N1 HI antibodies against
A/Vietnam/1294/2004 strain at D21 and D42 post-vaccination (Initially
seropositive cohort, ATP cohort for immunogenicity)

| Antibodies against | Group | Timing | N | Value | SCF 95% CI LL | UL |
|---|---|---|---|---|---|---|
| A/Vietnam | 7.5/NoAS | PI(D21) | 16 | 2.9 | 1.6 | 5.2 |
| | | PII(D42) | 16 | 3.4 | 1.9 | 6.2 |
| | 3.8/NoAS | PI(D21) | 21 | 1.4 | 1.1 | 2.0 |
| | | PII(D42) | 21 | 1.9 | 1.2 | 2.9 |
| | 7.5/AS | PI(D21) | 52 | 5.0 | 3.5 | 7.2 |
| | | PII(D42) | 52 | 8.9 | 6.3 | 12.5 |
| | 3.8/AS | PI(D21) | 62 | 3.6 | 2.7 | 4.8 |
| | | PII(D42) | 62 | 6.7 | 4.9 | 9.1 |

7.5/NoAS = H5N1 [2 × 3.8 µg HA];
3.8/NoAS = H5N1 [1 × 3.8 µg HA];
7.5/AS = H5N1 [2 × 3.8 µg HA/AS03];
3.8/AS = H5N1 [1 × 3.8 µg HA/AS03];
N = Number of subjects with pre- and post-vaccination results available;
SCF = Seroconversion Factor or geometric mean ratio (mean[log10(POST/PRE)]);
95% CI = 95% confidence interval,
LL = Lower Limit,
UL = Upper Limit;
PI(D21) = Post-vaccination at Day 21;
PII(D42) = post-vaccination at Day 42

Intermediate Conclusion for Seroconversion Factors for the Anti-VT Response in Subjects Initially Seropositive to A/Vietnam/1194/2004

The >2.0 SCF threshold was reached by all groups 21 days after the first and the second vaccination, except in the non-adjuvanted group with the 3.8 formulation (1.4 at D21 and 1.9 at D42). 21 A significant increase from 21 days after the first vaccination to 21 days after the second vaccination was only observed in the adjuvanted groups, with the 3.8 formulation.

IV.3.3. Neutralizing Antibody Response (Anti-Indonesia Responses in a Subset of Subjects of the Adjuvanted Groups)
IV.3.3.1. Geometric Mean Titers
The results are shown in Table 16.

TABLE 16

Seropositivity rates and geometric means titres (GMTs) of neutralising antibody titres against A/Indonesia/5/2005 strain at Days 0 and 42 (ATP cohort for immunogenicity)

| Antibody against | Group | Timing | N | n | % | ≥28 (1:dil) 95% CI LL | ≥28 (1:dil) 95% CI UL | GMT value | GMT 95% CI LL | GMT 95% CI UL | Min | Max |
|---|---|---|---|---|---|---|---|---|---|---|---|---|
| A/Indonesia | 7.5/AS | PRE | 82 | 48 | 58.5 | 47.1 | 69.3 | 39.7 | 32.0 | 49.3 | <28.0 | 360.0 |
|  |  | PII(D42) | 82 | 82 | 100 | 95.6 | 100 | 169.6 | 144.7 | 198.9 | 28.0 | 2840.0 |
|  | 3.8/AS | PRE | 87 | 57 | 65.5 | 54.6 | 75.4 | 44.2 | 36.0 | 54.1 | <28.0 | 226.0 |
|  |  | PII(D42) | 87 | 82 | 94.3 | 87.1 | 98.1 | 107.5 | 88.9 | 130.0 | <28.0 | 2260.0 |

7.5/AS = H5N1 [2 × 3.8 μg HA/AS03];
3.8/AS = H5N1 [1 × 3.8 μg HA/AS03];
GMT = Geometric Mean antibody Titre;
N = Number of subjects with available results;
n/% = number/percentage of seropositive subjects (HI titre >= 1:10);
95% CI = 95% confidence interval,
LL = Lower Limit,
UL = Upper Limit;
MIN/MAX = Minimum/Maximum;
PRE = Pre-vaccination at Day 0;
PII(D42) = Post-vaccination two at Day 42

Intermediate conclusion for geometric mean titers for the Anti-IN response

Prior to vaccination GMTs were similar in both adjuvanted groups (44.2 in the 3.8/AS group and 39.7 in the 7.5/AS group). After the second administration(s), the GMTs had increased significantly in each group (107.5 in the 3.8/AS group and 169.6 in the 7.5/AS group).

IV.3.3.2. Seroconversion Rates
The results are shown in Table 17.

TABLE 17

Seroconversion rate (SCR) for neutralising antibody response against A/Indonesia/5/2005 strain at Day 42 (ATP cohort for immunogenicity)

| Antibodies against | Group | Timing | N | n | % | SCR 95% CI LL | SCR 95% CI UL |
|---|---|---|---|---|---|---|---|
| A/Indonesia | 7.5/AS | PII(D42) | 82 | 40 | 48.8 | 37.6 | 60.1 |
|  | 3.8/AS | PII(D42) | 87 | 25 | 28.7 | 19.5 | 39.4 |

7.5/AS = H5N1 [2 × 3.8 μg HA/AS03];
3.8/AS = H5N1 [1 × 3.8 μg HA/AS03];
Seroconversion defined as: For initially seronegative subjects, antibody titre >=56 after vaccination; For initially seropositive subjects, antibody titre after vaccination >=4 fold the pre-vaccination antibody titre;
N = Number of subjects with pre-and post-vaccination results available;
n/% = Number/percentage of seroconverted subjects;
95% CI = 95% confidence interval,
LL = Lower Limit,
UL = Upper Limit;
PII(D42) = Post-vaccination two at Day 42

Intermediate Conclusion for Seroconversion Rates for the Anti-IN Response

After the second administration, there was a trend for a higher SCR in the 7.5/AS group (48.8%) compared to the 3.8/AS group (28.7%). Notably, the percentage of subjects reaching a neutralising antibody titre of 1:40 and 1:80 was higher in the 7.5/AS group, compared to the 3.8/AS group.

IV.3.4. Cell-Mediated Immune Response Against A/Vietnam/1194/2004 (Influenza-Specific CD4 T-cells)
The results are shown in Table 18 and in FIG. 7.

TABLE 18

Descriptive Statistics on the frequency cytokine-positive T-cells (per million T-cells) for CD4.CD40L, CD4.ALL DOUBLES, CD4.IL-2, CD4.TNFa, CD4.INFg stimulated by Split H5N1 A/Vietnam (ATP cohort for immunogenicity)

| Test description | Group | Timing | N | Nmiss | GM | Mean | SD |
|---|---|---|---|---|---|---|---|
| CD4.ALL DOUBLES | 7.5/NoAS | PRE | 40 | 4 | 545.37 | 785.98 | 820.30 |
| | | PI(D21) | 34 | 10 | 1284.19 | 1620.26 | 1058.55 |
| | | PII(D42) | 30 | 14 | 1316.80 | 1596.33 | 1060.97 |
| | 3.8/NoAS | PRE | 44 | 10 | 494.27 | 662.07 | 518.93 |
| | | PI(D21) | 42 | 12 | 943.54 | 1252.02 | 1034.54 |
| | | PII(D42) | 43 | 11 | 920.90 | 1208.16 | 745.36 |
| | 7.5/AS | PRE | 122 | 23 | 495.77 | 670.50 | 606.84 |
| | | PI(D21) | 110 | 35 | 1793.92 | 2315.24 | 1867.92 |
| | | PII(D42) | 118 | 27 | 3049.03 | 4171.24 | 4208.17 |
| | 3.8/AS | PRE | 129 | 23 | 393.71 | 620.14 | 590.66 |
| | | PI(D21) | 112 | 40 | 1407.29 | 1845.30 | 1354.44 |
| | | PII(D42) | 120 | 32 | 2260.19 | 3034.88 | 2242.14 |
| CD4.CD40L | 7.5/NoAS | PRE | 40 | 4 | 540.73 | 761.80 | 771.32 |
| | | PI(D21) | 34 | 10 | 1230.48 | 1547.94 | 989.52 |
| | | PII(D42) | 30 | 14 | 1254.99 | 1510.43 | 974.20 |
| | 3.8/NoAS | PRE | 44 | 10 | 461.29 | 644.09 | 513.70 |
| | | PI(D21) | 42 | 12 | 944.17 | 1226.12 | 1015.89 |
| | | PII(D42) | 43 | 11 | 944.59 | 1172.72 | 728.39 |
| | 7.5/AS | PRE | 122 | 23 | 485.71 | 655.20 | 594.88 |
| | | PI(D21) | 110 | 35 | 1731.58 | 2247.71 | 1828.74 |
| | | PII(D42) | 118 | 27 | 2971.34 | 4056.64 | 4076.52 |
| | 3.8/AS | PRE | 129 | 23 | 388.69 | 604.88 | 571.91 |
| | | PI(D21) | 112 | 40 | 1374.26 | 1782.67 | 1304.02 |
| | | PII(D42) | 120 | 32 | 2198.66 | 2943.00 | 2165.46 |
| CD4.IL-2 | 7.5/NoAS | PRE | 40 | 4 | 510.47 | 710.15 | 700.70 |
| | | PI(D21) | 34 | 10 | 1178.95 | 1490.62 | 1001.08 |
| | | PII(D42) | 30 | 14 | 1242.26 | 1485.70 | 976.18 |
| | 3.8/NoAS | PRE | 44 | 10 | 448.43 | 610.68 | 500.03 |
| | | PI(D21) | 42 | 12 | 868.24 | 1149.02 | 967.47 |
| | | PII(D42) | 43 | 11 | 854.90 | 1127.19 | 727.62 |
| | 7.5/AS | PRE | 122 | 23 | 461.23 | 609.22 | 552.91 |
| | | PI(D21) | 110 | 35 | 1651.88 | 2146.25 | 1776.72 |
| | | PII(D42) | 118 | 27 | 2762.65 | 3778.94 | 3720.42 |
| | 3.8/AS | PRE | 129 | 23 | 376.03 | 571.24 | 545.75 |
| | | PI(D21) | 112 | 40 | 1318.03 | 1716.82 | 1250.79 |
| | | PII(D42) | 120 | 32 | 2086.84 | 2813.43 | 2086.66 |
| CD4.INFg | 7.5/NoAS | PRE | 40 | 4 | 371.67 | 595.68 | 695.33 |
| | | PI(D21) | 34 | 10 | 852.75 | 1137.03 | 823.22 |
| | | PII(D42) | 30 | 14 | 828.99 | 1044.83 | 732.58 |
| | 3.8/NoAS | PRE | 44 | 10 | 322.17 | 460.80 | 349.01 |
| | | PI(D21) | 42 | 12 | 579.45 | 876.48 | 828.17 |
| | | PII(D42) | 43 | 11 | 671.86 | 821.67 | 552.02 |
| | 7.5/AS | PRE | 122 | 23 | 343.35 | 505.50 | 549.24 |
| | | PI(D21) | 110 | 35 | 997.15 | 1291.85 | 1023.96 |
| | | PII(D42) | 118 | 27 | 1535.37 | 2293.17 | 2864.48 |
| | 3.8/AS | PRE | 129 | 23 | 270.99 | 459.03 | 500.13 |
| | | PI(D21) | 112 | 40 | 685.44 | 1026.93 | 884.75 |
| | | PII(D42) | 120 | 32 | 1123.16 | 1626.48 | 1356.18 |
| CD4.TNFa | 7.5/NoAS | PRE | 40 | 4 | 382.79 | 563.75 | 641.28 |
| | | PI(D21) | 34 | 10 | 910.69 | 1203.59 | 861.04 |
| | | PII(D42) | 30 | 14 | 918.50 | 1161.33 | 822.20 |
| | 3.8/NoAS | PRE | 44 | 10 | 369.54 | 496.30 | 427.12 |
| | | PI(D21) | 42 | 12 | 708.15 | 980.36 | 915.15 |
| | | PII(D42) | 43 | 11 | 701.35 | 896.12 | 691.26 |
| | 7.5/AS | PRE | 122 | 23 | 358.27 | 518.70 | 538.07 |
| | | PI(D21) | 110 | 35 | 1207.95 | 1641.36 | 1527.86 |
| | | PII(D42) | 118 | 27 | 2170.46 | 3100.96 | 3380.48 |
| | 3.8/AS | PRE | 129 | 23 | 310.91 | 464.85 | 486.27 |
| | | PI(D21) | 112 | 40 | 932.64 | 1239.38 | 974.72 |
| | | PII(D42) | 120 | 32 | 1595.64 | 2227.27 | 1798.95 |

7.5/NoAS = H5N1 [2 × 3.8 μg HA];
3.8/NoAS = H5N1 [1 × 3.8 μg HA];
7.5/AS = H5N1 [2 × 3.8 μg HA/AS03];
3.8/AS = H5N1 [1 × 3.8 μg HA/AS03];
N = number of subjects with available results;
Nmiss = number of subjects with missing results;
GM = Geometric Mean;
SD = Standard Deviation;
Q1, Q3 = First and third quartiles;
Min/Max = Minimum/Maximum Intermediate Conclusion for the Cell-Mediated Immune Response Against A/Vietnam/1194/2004 (Influenza-Specific CD4 T-Cells)

Antigen-specific Th1 CD4 T-cell responses were elicited in all study groups. These were however of low amplitude in the two non-adjuvanted groups. In the adjuvanted study groups these were of higher amplitude. In these latter groups, the value markedly increased after the second administration(s), whereas the increase was less marked in the 3.8/NoAS group, and even tended to decrease in the 7.5/NoAS group.

IV.4. Conclusions

All adjuvanted groups fulfilled all 3 CHMP criteria against A/Vietnam/1194/2004 after the second vaccination dose.

All 3 CHMP criteria were also met against A/Vietnam/1194/2004 after the first vaccination in subjects of the adjuvanted groups who were already seropositive to A/Vietnam/1194/2004 before vaccination. In other words, in this sub-population, a single [=1×3.8 μg+AS] or double [=2×3.8 μg+AS] dose of vaccine was sufficient to mount an homologous H5N1 HI response that fulfils the established licensing CHMP criteria, as rapidly as 21 days after the first vaccination.

Subjects of the adjuvanted groups who were seronegative to A/Vietnam/1194/2004 before vaccination however needed two doses of vaccine to elicit an H5N1 HI response that met the 3 CHMP criteria.

Better heterologous (anti-IN) responses were observed in the adjuvanted groups, with some of the CHMP criteria being reached after two doses of vaccination (SCR for the 7.5/AS group and SCF for the 3.8/AS and 7.5/AS groups).

Better cell-mediated immune, influenza-specific Th1 CD4 T-cell responses, were observed in the adjuvanted groups, with a further appreciable increase after the second vaccine administration in these groups.

Example V

Preclinical Evaluation of an Accelerated Priming of Naïve C57Bl/6 Mice with an Adjuvanted Split H5N1 Vaccines V.1. Experimental Design and Objective Two experiments in H5N1-naive mice were performed in order to evaluate the impact of vaccination schedule or timing between two administrations of H5N1 split vaccines (A/Vietnam/1194/04 or A/Indonesia/5/05) adjuvanted with AS03 in terms of intensity and kinetics of the humoral response. The H5N1 split vaccines adjuvanted with AS03 were administered at 0, 7, 14 or 21 day intervals. In addition, an homologous boost was performed 84 days after the second immunization. The kinetics of the humoral immune response were evaluated after 7, 14, 21, 42 and 84 days after the second immunization. In addition, the magnitude of the response were measured 21 days after the boost.

V.1.1. Treatment/Group (Table 19A and 19B)

Groups of 20 adult female naive C57Bl/6 mice received one or two intramuscular administrations on day 0, or two administrations at 7, 14 or 21 days apart of pandemic H5N1 candidate vaccine in a total volume of 50 μl. In addition, a booster immunization was performed 84 days after the last immunization in groups 1 to 5.

Mice were immunized with formulations containing split antigens adjuvanted with AS03. The strains used for the immunizations included H5N1 A/Vietnam/1194/04 or H5N1 A/Indonesia/5/05 viral antigen (0.38 μg/strain corresponding to $1/10^{th}$ of the human dose).

TABLE 19A

| Groups | Antigen/Formulations | Interval of injection |
| --- | --- | --- |
| 1 | A/Vietnam AS03 (0.38 μg) | 1 administration, Day 0 |
| 2 | A/Vietnam AS03 (0.38 μg) | 2 administrations, Day 0 (different arms) |
| 3 | A/Vietnam AS03 (0.38 μg) | 2 administrations, Days 0 and 7 |
| 4 | A/Vietnam AS03 (0.38 μg) | 2 administrations, Days 0 and 14 |
| 5 | A/Vietnam AS03 (0.38 μg) | 2 administrations, Days 0 and 21 |
| 6 | PBS | 2 administrations, Days 0 and 21 |

TABLE 19B

| Groups | Antigen/Formulations | Interval of injection |
| --- | --- | --- |
| 1 | A/Indonesia AS03 (0.38 μg) | 1 administration, Day 0 |
| 2 | A/Indonesia AS03 (0.38 μg) | 2 administrations, Day 0 (different arms) |
| 3 | A/Indonesia AS03 (0.38 μg) | 2 administrations, Days 0 and 7 |
| 4 | A/Indonesia AS03 (0.38 μg) | 2 administrations, Days 0 and 14 |
| 5 | A/Indonesia AS03 (0.38 μg) | 2 administrations, Days 0 and 21 |
| 6 | PBS | 2 administrations, Days 0 and 21 |

V.1.2. Read-Outs (Table 20)

The humoral immune response was measured 7, 14, 21, 42 and about 3 months after the second immunization (20 mice/group pooled in 10 pools of 2 mice) by hemagglutination inhibition assay and neutralization assay.

TABLE 20

| Read-out | Timepoint | Sample type | Analysis method |
| --- | --- | --- | --- |
| Humoral responses | Days 0, 7, 14, 21, 42 and 84 after the second immunization and at 21 days after the booster (day 105) | Sera (on pooled sera for Day 0 and on individual sera for others timepoints) | HI and neutralzing titers |

V.2. Results

V.2.1. A/Vietnam/1194/04 Vaccine: Table 19A and FIGS. 8 and 9

Mice immunized with two doses of A/Vietnam/1194/04 adjuvanted with AS03 administrated with 7, 14 or 21 day intervals showed higher HI and neutralizing antibody responses 7, 14 and 21 days after the second immunization compared to mice immunized with one or two concomitant doses of A/Vietnam/1194/04 vaccine adjuvanted with AS03 administered at Day 0.

Mice immunized with two doses of A/Vietnam/1194/04 vaccine adjuvanted with AS03 and administered with a 14 or 21 day interval had higher HI and neutralizing antibody titers at 7, 14 and 21 days after the second immunization compared to mice immunized with two doses of A/Vietnam/1194/04 vaccine adjuvanted with AS03 at a 7 day interval.

Whatever the interval between two doses of A/Vietnam/1194/04 vaccine adjuvanted with AS03 (7, 14 or 21 days interval) similar persistent immune responses (HI and neutralizing antibody titers) were observed at 42 or 84 days after the second immunization.

Moreover, the boost with A/Vietnam/1194/04 vaccine adjuvanted with AS03 at 84 days resulted in similar HI titers in all mice immunized with one or two doses of A/Vietnam/1194/04 adjuvanted with AS03 administrated with 0, 7, 14 or 21 day intervals.

V.2.1. A/Indonesia: Table 19B and FIGS. 10 and 11

Mice immunized with two doses of A/Indonesia/5/05 adjuvanted with AS03 and administrated with 7, 14 or 21 days interval showed higher HI and neutralizing antibody responses 7, 14, 21, 42 and 84 days after the second immunization compared to mice immunized with one or two doses of A/Indonesia/5/05 vaccine adjuvanted with AS03 and administered on Day 0.

Mice immunized with two doses of A/Indonesia/5/05 vaccine adjuvanted with AS03 and administered with a 14 or 21 day interval had higher HI and neutralizing antibody titers at 7, 14, 21, 42 and 84 days after the second immunization compared to mice immunized with two doses of A/Indonesia/5/05 vaccine adjuvanted with AS03 at a 7 day interval.

The boost with A/Indonesia/5/05 vaccine adjuvanted with AS03 at 84 days after immunization with the same vaccine resulted in similar HI titers in all mice immunized with one or two doses of A/Indonesia/5/05 adjuvanted with AS03 and administrated with 0, 7, 14 or 21 day intervals.

V.2.2. Conclusions.

For both H5N1 vaccines (A/Vietnam/1194/04 or A/Indonesia/5/05) adjuvanted with AS03, mice immunized with two doses at 7, 14 or 21 days interval showed higher humoral immune responses compared to mice immunized with one or two doses of the same vaccine administered on Day 0.

In addition, higher humoral immune responses were obtained in mice immunized with two doses of the H5N1 vaccines (A/Vietnam/1194/04 or A/Indonesia/5/05) adjuvanted with AS03 at 14 or 21 days interval compared to mice immunized with two doses at 7 days interval.

Finally, whatever the schedule of administration of 1 or 2 dose adjuvanted vaccine, the boost with a similar vaccine adjuvanted with AS03 induced similar humoral immune responses in all mice. In addition the data demonstrate the potential for similar immune priming independent of the schedule or the number of doses.

The invention claimed is:

1. A method of inducing a primary immune response against influenza virus in a human individual or a human population, the method comprising administering by a parenteral route an immunogenic composition comprising a non-live influenza virus or antigenic preparation thereof and an adjuvant comprising an oil-in-water emulsion comprising a squalene and an emulsifying agent, wherein two primary doses of said immunogenic composition are administered at an interval between 7 and 10 days.

2. The method of claim 1, wherein the two primary doses are administered at an interval of 7 days.

3. The method of claim 1, wherein the adjuvant is an oil-in-water emulsion comprising squalene, an emulsifying agent and a sterol or a tocol.

4. The method of according to claim 3, wherein the tocol is a tocopherol.

5. The method of claim 3, wherein the tocopherol is alpha tocopherol.

6. The method of claim 3, wherein squalene is present in an amount of about 0.125% (v/v) to about 5% (v/v) of the total volume of said immunogenic composition.

7. The method of claim 3, wherein the ratio of squalene: tocopherol is equal to or less than 1.

8. The method of claim 3, wherein the emulsifying agent is polysorbate 80 or polyoxyethylene sorbitan monooleate (Tween 80™).

9. The method of claim 3, wherein the emulsifying agent is present at an amount of about 0.1% (v/v) to about 2.0% (v/v) of the total volume of the immunogenic composition.

10. The method of claim 1, wherein said non-live influenza virus or antigenic preparation thereof comprises an amount of HA antigen that does not exceed 15 μg per dose per influenza virus strain.

11. The method of claim 10, wherein the amount of HA antigen is between 1-7.5 μg per dose per influenza virus strain.

12. The method of claim 1, wherein the immunogenic composition is monovalent or multivalent.

13. The method of claim 12, wherein the composition for primary vaccination comprises at least one pandemic influenza virus, or at least one seasonal strain, or both.

14. The method of claim 13, wherein the pandemic influenza virus strain is selected from the group consisting of: H5N1, H9N2, H5N8, H5N9, H7N4, H7N7, H2N2, H10N7, H5N2, H5N3, H7N2, H7N1, and H7N3.

15. The method of claim 1, wherein the non-live influenza virus or antigenic preparation thereof is in the form of: a purified whole influenza virus, a sub-unit component of influenza virus, a virosome or a virus-like particle.

16. The method of claim 1, wherein the non-live influenza virus or antigenic composition thereof is produced in cell culture or in embryonated eggs.

17. The method of claim 1, wherein administering the immunogenic composition achieves at least one of the following Committee for Medicinal Products for Human Use criteria for influenza vaccines in terms of anti-haemagglutinin (anti-HA) antibodies:
 (i) a seroconversion rate of greater than or equal to 30%;
 (ii) a seroprotection rate of greater than or equal to 60%; and
 (iii) a conversion factor of greater than or equal to 2.0.

18. The method of claim 1, wherein administering the immunogenic composition achieves both a seroconversion rate against a drift-variant influenza strain, for neutralising antibody response of greater than or equal to 30, and additionally at least one of the additional following criteria in terms of anti-haemagglutinin (anti-HA) antibodies, against the vaccine strain:
 (i) a seroconversion rate of greater than or equal to 30%;
 (ii) a seroprotection rate of greater than or equal to 60%; and
 (iii) a conversion factor of greater than or equal to 2.0.

19. The method of claim 17, wherein two of any of said criteria are achieved against the homologous (immunogenic composition) influenza strain, or against an antigenic variant influenza strain, or against both the homologous and the antigenic variant virus strains.

20. The method of claim 1, wherein administering the immunogenic composition reduces the severity or prevents influenza infections caused by an influenza strain, wherein the influenza infection is caused by a drift-variant of the strain present in the immunogenic composition.

21. The method of claim 1, further comprising revaccinating the human individual or the human population by administering an immunogenic composition comprising an inactivated, recombinant or live attenuated influenza virus or antigenic preparation thereof.

22. The method of claim 21, wherein the composition used for the revaccination is not adjuvanted or contains an adjuvant.

23. The method of claim 21, wherein the composition for revaccination is monovalent or multivalent.

24. The method of claim 22 wherein the adjuvant is an oil-in-water emulsion adjuvant.

25. The method of claim 21, wherein the immunogenic composition for revaccination contains an influenza virus or antigenic preparation thereof from at least one pandemic or at least one seasonal strain or both.

26. The method of claim 25, wherein the pandemic strain, when present, is selected from the group consisting of: H5N1, H9N2, H5N8, H5N9, H7N4, H7N7, H2N2, H10N7, H5N2, H5N3, H7N2, H7N1, and H7N3.

27. The method of claim 21, wherein the revaccination is made with an immunogenic influenza composition containing an inactivated, recombinant or live attenuated influenza virus strain or antigenic preparation thereof which is an antigenic variant of that included in the composition for primary vaccination.

28. The method of claim 1, wherein the non-live influenza virus or antigenic preparation thereof is a split virus or split virus antigenic preparation.

* * * * *

```
                        SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic CpG sequence

<400> SEQUENCE: 1
tccatgacgt tcctgacgtt                                              20

<210> SEQ ID NO 2
<211> LENGTH: 18
<212> TYPE: DNA
<213> ORGANISM: Artificial Sequence
<220> FEATURE:
<223> OTHER INFORMATION: Synthetic CpG sequence

<400> SEQUENCE: 2
tctcccagcg tgcgccat                                                18

<210> SEQ ID NO 3
<211> LENGTH: 30
<212> TYPE: DNA
<213> ORGANISM: Artificial Sequence
<220> FEATURE:
<223> OTHER INFORMATION: Synthetic CpG sequence

<400> SEQUENCE: 3
accgatgacg tcgccggtga cggcaccacg                                   30

<210> SEQ ID NO 4
<211> LENGTH: 24
<212> TYPE: DNA
<213> ORGANISM: Artificial Sequence
<220> FEATURE:
<223> OTHER INFORMATION: Synthetic CpG sequence

<400> SEQUENCE: 4
tcgtcgtttt gtcgttttgt cgtt                                         24

<210> SEQ ID NO 5
<211> LENGTH: 20
<212> TYPE: DNA
<213> ORGANISM: Artificial Sequence
```

```
<220> FEATURE:
<223> OTHER INFORMATION: Synthetic CpG sequence

<400> SEQUENCE: 5
tccatgacgt tcctgatgct                                              20

<210> SEQ ID NO 6
<211> LENGTH: 22
<212> TYPE: DNA
<213> ORGANISM: Artificial Sequence
<220> FEATURE:
<223> OTHER INFORMATION: Synthetic CpG sequence

<400> SEQUENCE: 6
tcgacgtttt cggcgcgcgc cg                                           22
```